(12) United States Patent
Hatefi et al.

(10) Patent No.: US 11,702,462 B2
(45) Date of Patent: Jul. 18, 2023

(54) GENE TRANSFER SYSTEMS FOR STEM CELL ENGINEERING

(71) Applicant: Rutgers, The State University of New Jersey, New Brunswick, NJ (US)

(72) Inventors: Arash Hatefi, Metuchen, NJ (US); Xuguang Chen, Somerset, NJ (US); Alireza Nomani, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 605 days.

(21) Appl. No.: 16/631,309

(22) PCT Filed: Jul. 19, 2018

(86) PCT No.: PCT/US2018/042909
§ 371 (c)(1),
(2) Date: Jan. 15, 2020

(87) PCT Pub. No.: WO2019/018660
PCT Pub. Date: Jan. 24, 2019

(65) Prior Publication Data
US 2020/0207834 A1    Jul. 2, 2020

Related U.S. Application Data

(60) Provisional application No. 62/534,300, filed on Jul. 19, 2017.

(51) Int. Cl.
| | | |
|---|---|---|
| C07K 14/81 | (2006.01) | |
| A61K 47/62 | (2017.01) | |
| C07K 14/00 | (2006.01) | |
| C12P 21/02 | (2006.01) | |
| C07K 14/71 | (2006.01) | |
| C07K 14/435 | (2006.01) | |
| C12N 5/0775 | (2010.01) | |
| C12N 9/24 | (2006.01) | |
| C12N 15/85 | (2006.01) | |
| C07K 7/04 | (2006.01) | |
| C12N 15/63 | (2006.01) | |
| C12N 15/11 | (2006.01) | |

(52) U.S. Cl.
CPC ............... *C07K 14/71* (2013.01); *C07K 7/04* (2013.01); *C07K 14/001* (2013.01); *C07K 14/435* (2013.01); *C12N 5/0667* (2013.01); *C12N 9/2497* (2013.01); *C12N 15/63* (2013.01); *C12N 15/85* (2013.01); *C07K 2319/00* (2013.01); *C07K 2319/01* (2013.01); *C07K 2319/06* (2013.01); *C07K 2319/74* (2013.01); *C07K 2319/80* (2013.01); *C12N 15/11* (2013.01); *C12N 2500/25* (2013.01); *C12N 2510/00* (2013.01)

(58) Field of Classification Search
None
See application file for complete search history.

(56) References Cited

U.S. PATENT DOCUMENTS

| | | |
|---|---|---|
| 7,465,784 B2 | 12/2008 | Wang |
| 2004/0266694 A1 | 12/2004 | Tchistiakova et al. |
| 2007/0098702 A1 | 5/2007 | Megeed et al. |
| 2008/0207502 A1 | 8/2008 | Rastelli et al. |
| 2011/0076342 A1 | 3/2011 | Malkas et al. |
| 2011/0082074 A1 | 4/2011 | Nishimura et al. |
| 2011/0268660 A1 | 11/2011 | Danikas et al. |
| 2013/0101628 A1 | 4/2013 | Webber et al. |

FOREIGN PATENT DOCUMENTS

WO    WO 2013/132094 A1    9/2013

OTHER PUBLICATIONS

Anna Arís et al (Modular protein engineering for non-viral gene therapy (Trends in Biotechnology vol. 22, Issue 7, Jul. 2004, pp. 371-377) (Year: 2004).*
Jeffery D. Fritz et al (Gene Transfer into Mammalian Cells Using Histone-Condensed Plasmid DNA. Human Gene Therapy vol. 7 Issue 12: Mar. 20, 2008 (Year: 2008).*
Wagstaff et al Nucleocytoplasmic transport of DNA: enhancing non-viral gene transfer. Biochem J, 2007, 406: 185-202 (Year: 2007).*
Danuta Balick et al Structure and function correlation in histone H2A peptide-mediated gene transfer PNAS May 28, 2002 vol. 99 No. 11 7467-7471 (Year: 2002).*
International Search Report and Written Opinion in corresponding PCT Application No. PCT/US2018/042909, dated Nov. 8, 2018.
Wang et al. "Incorporation of histone derived recombinant protein for enhanced disassembly of core-membrane structured liposomal nanoparticles for efficient siRNA delivery," J Control Release, Aug. 23, 2013 (Aug. 23, 2013), vol. 172, pp. 179-189. entire document.
Ferreira et al. "Optimization of a gene electrotransfer method for mesenchymal stem cell transfection," Gene Ther, Feb. 7, 2008 (Feb. 7, 2008), vol. 15, pp. 537-544. entire document.
Canine et al. "Biosynthesis and characterization of a novel genetically engineered polymer for targeted gene transfer to cancer cells," J Control Release, Apr. 18, 2009 (Apr. 18, 2009), vol. 138, pp. 188-196. entire document.
Wang et al, "A designer biomimetic vector with a chimeric architecture for targeted gene transfer," J Control Release, Mar. 18, 2009 (Mar. 18, 2009), vol. 137, pp. 46-53. entire document.
Wang et al. "329. A Genetically Engineered Multifunctional Vector for HER2 Targeted Cancer Suicide Gene Therapy," Molecular Therapy, May 1, 2010 (May 1, 2010), vol. 18, Supp. 1, p. 5127, Abstract only. entire document.

\* cited by examiner

*Primary Examiner* — Kagnew H Gebreyesus
(74) *Attorney, Agent, or Firm* — Leason Ellis LLP

(57) ABSTRACT

The present disclosure provides for non-viral compositions and methods for delivering nucleic acids into eukaryotic cells (e.g., stem cells) with high efficiency and low genotoxicity.

17 Claims, 26 Drawing Sheets
Specification includes a Sequence Listing.

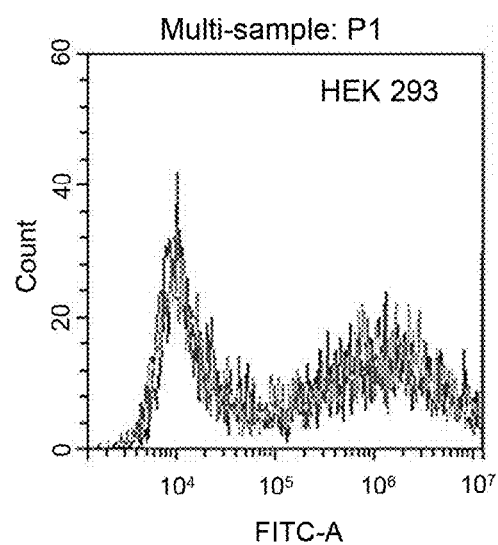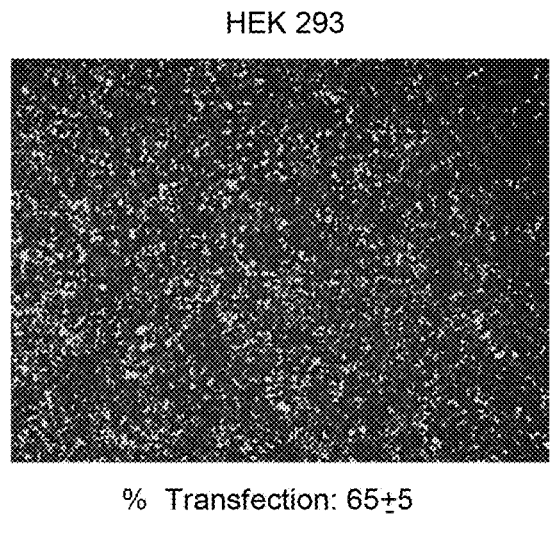
Figure 10A  Figure 10B
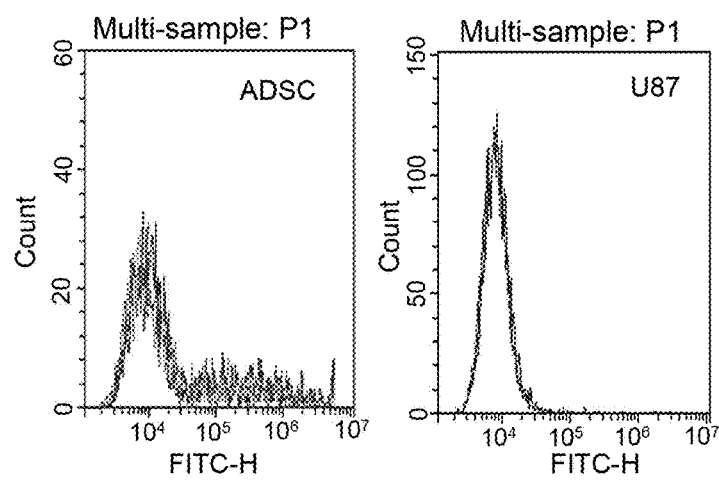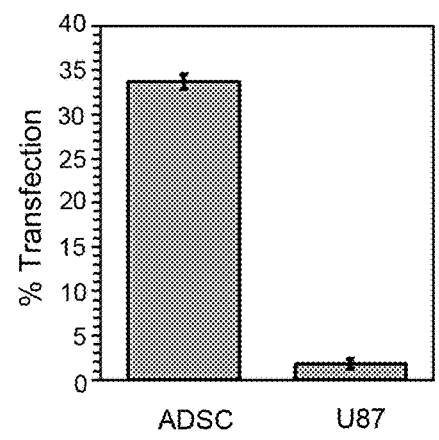
Figure 11A  Figure 11B  Figure 11C

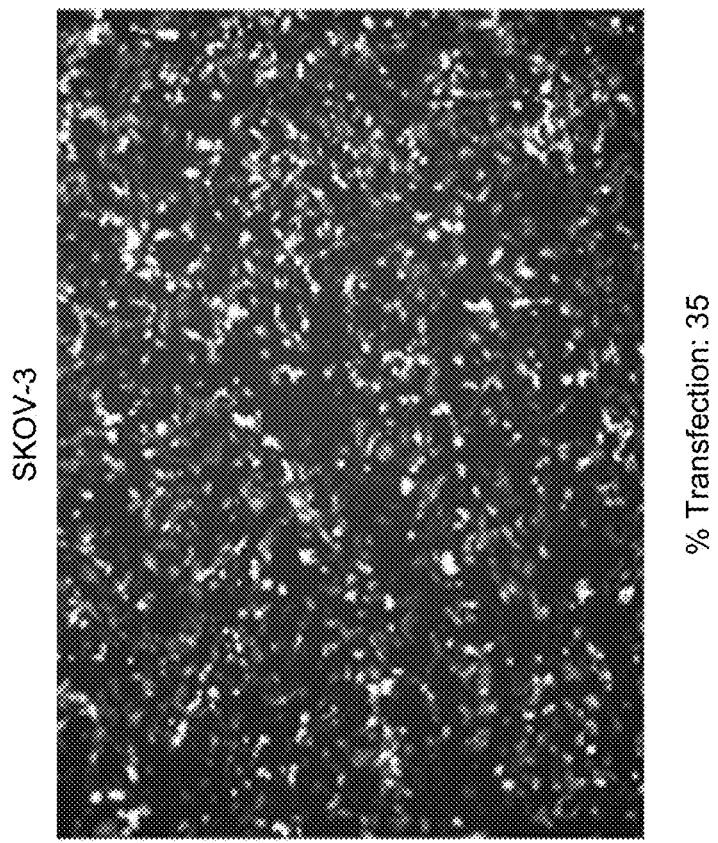
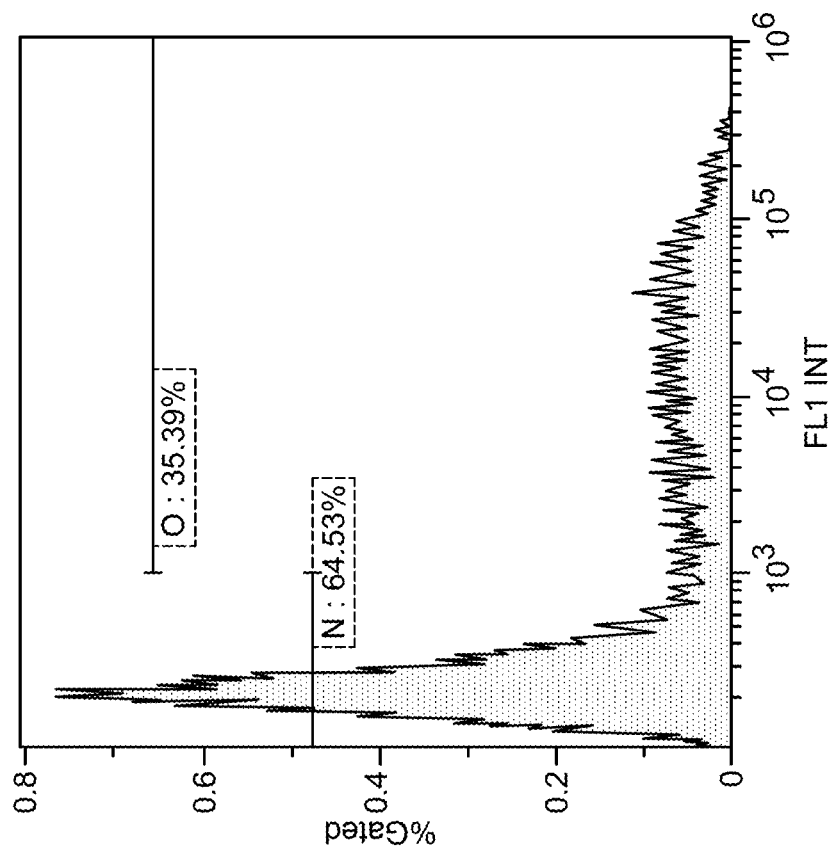
Figure 12B
Figure 12A

```
                            SEQUENCE LISTING

<160> NUMBER OF SEQ ID NOS: 269

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Leu Thr Trp Gln Glu Leu Tyr Gln Leu Lys Tyr Lys Gly Ile
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asn Gly Tyr Glu Ile Glu Trp Tyr Ser Trp Val Thr His Gly Met Tyr
1               5                   10                  15

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 5
<211> LENGTH: 144
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 5

```
Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Ser Gly Arg Gly Lys Gln Gly Gly Lys Ala Arg Ala
        35                  40                  45

Lys Ala Lys Thr Arg Ser Ser Arg Ala Gly Leu Gln Phe Pro Val Gly
    50                  55                  60

Arg Val His Arg Leu Leu Arg Lys Ser Gly Arg Gly Lys Gln Gly Gly
65                  70                  75                  80

Lys Ala Arg Ala Lys Ala Lys Thr Arg Ser Ser Arg Ala Gly Leu Gln
                85                  90                  95

Phe Pro Val Gly Arg Val His Arg Leu Leu Arg Lys Ser Gly Arg Gly
            100                 105                 110

Lys Gln Gly Gly Lys Ala Arg Ala Lys Ala Lys Thr Arg Ser Ser Arg
        115                 120                 125

Ala Gly Leu Gln Phe Pro Val Gly Arg Val His Arg Leu Leu Arg Lys
    130                 135                 140
```

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30
```

<210> SEQ ID NO 7
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Ser Gly Arg Gly Lys Gln Gly Gly Lys Ala Arg Ala
        35                  40                  45

Lys Ala Lys Thr Arg Ser Ser Arg Ala Gly Leu Gln Phe Pro Val Gly
    50                  55                  60

Arg Val His Arg Leu Leu Arg Lys Gly Ser Arg Gly Lys Gln Gly Gly
65                  70                  75                  80

Lys Ala Arg Ala Lys Ala Lys Thr Arg Ser Ser Arg Ala Gly Leu Gln
                85                  90                  95
```

```
Phe Pro Val Gly Arg Val His Arg Leu Leu Arg Lys Ser Gly Arg Gly
            100                 105                 110

Lys Gln Gly Gly Lys Ala Arg Ala Lys Ala Lys Thr Arg Ser Ser Arg
        115                 120                 125

Ala Gly Leu Gln Phe Pro Val Gly Arg Val His Arg Leu Leu Arg Lys
    130                 135                 140

Gly Gly Gly Trp Glu Ala Ala Leu Ala Glu Ala Leu Ala Glu Ala Leu
145                 150                 155                 160

Ala Glu His Leu Ala Glu Ala Leu Ala Glu Ala Leu Glu Ala Leu Ala
                165                 170                 175

Ala
```

<210> SEQ ID NO 8
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val Ser Gly Arg Gly Lys
            20                  25                  30

Gln Gly Gly Lys Ala Arg Ala Lys Ala Lys Thr Arg Ser Ser Arg Ala
        35                  40                  45

Gly Leu Gln Phe Pro Val Gly Arg Val His Arg Leu Leu Arg Lys Ser
    50                  55                  60

Gly Arg Gly Lys Gln Gly Gly Lys Ala Arg Ala Lys Ala Lys Thr Arg
65                  70                  75                  80

Ser Ser Arg Ala Gly Leu Gln Phe Pro Val Gly Arg Val His Arg Leu
                85                  90                  95

Leu Arg Lys Gly Ser Arg Gly Lys Gln Gly Gly Lys Ala Arg Ala Lys
            100                 105                 110

Ala Lys Thr Arg Ser Ser Arg Ala Gly Leu Gln Phe Pro Val Gly Arg
        115                 120                 125

Val His Arg Leu Leu Arg Lys Ser Gly Arg Gly Lys Gln Gly Gly Lys
    130                 135                 140

Ala Arg Ala Lys Ala Lys Thr Arg Ser Ser Arg Ala Gly Leu Gln Phe
145                 150                 155                 160

Pro Val Gly Arg Val His Arg Leu Leu Arg Lys Gly Gly Gly Trp Glu
                165                 170                 175

Ala Ala Leu Ala Glu Ala Leu Ala Glu Ala Leu Ala Glu His Leu Ala
            180                 185                 190

Glu Ala Leu Ala Glu Ala Leu Glu Ala Leu Ala Ala
        195                 200
```

<210> SEQ ID NO 9
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Lys Glu Thr Trp Trp Glu Thr Trp Trp Thr Glu Trp Ser Gln Pro Lys
1               5                   10                  15

Lys Lys Arg Lys Val Ser Gly Arg Gly Lys Gln Gly Gly Lys Ala Arg
            20                  25                  30

Ala Lys Ala Lys Thr Arg Ser Ser Arg Ala Gly Leu Gln Phe Pro Val
        35                  40                  45

Gly Arg Val His Arg Leu Leu Arg Lys Ser Gly Arg Gly Lys Gln Gly
    50                  55                  60

Gly Lys Ala Arg Ala Lys Ala Lys Thr Arg Ser Ser Arg Ala Gly Leu
65                  70                  75                  80

Gln Phe Pro Val Gly Arg Val His Arg Leu Leu Arg Lys Gly Ser Arg
                85                  90                  95

Gly Lys Gln Gly Gly Lys Ala Arg Ala Lys Ala Lys Thr Arg Ser Ser
            100                 105                 110

Arg Ala Gly Leu Gln Phe Pro Val Gly Arg Val His Arg Leu Leu Arg
            115                 120                 125

Lys Ser Gly Arg Gly Lys Gln Gly Gly Lys Ala Arg Ala Lys Ala Lys
        130                 135                 140

Thr Arg Ser Ser Arg Ala Gly Leu Gln Phe Pro Val Gly Arg Val His
145                 150                 155                 160

Arg Leu Leu Arg Lys Gly Gly Trp Glu Ala Ala Leu Ala Glu Ala
                165                 170                 175

Leu Ala Glu Ala Leu Ala Glu His Leu Ala Glu Ala Leu Ala Glu Ala
            180                 185                 190

Leu Glu Ala Leu Ala Ala
        195
```

<210> SEQ ID NO 10
<211> LENGTH: 203
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 10

```
Lys Leu Thr Trp Gln Glu Leu Tyr Gln Leu Lys Tyr Lys Gly Ile Gly
1               5                   10                  15

Gly Gly Ser Gly Gly Gly Ser Gly Gly Gly Ser Gly Arg Gly Lys Gln
            20                  25                  30

Gly Gly Lys Ala Arg Ala Lys Ala Lys Thr Arg Ser Ser Arg Ala Gly
        35                  40                  45

Leu Gln Phe Pro Val Gly Arg Val His Arg Leu Leu Arg Lys Ser Gly
    50                  55                  60

Arg Gly Lys Gln Gly Gly Lys Ala Arg Ala Lys Ala Lys Thr Arg Ser
65                  70                  75                  80

Ser Arg Ala Gly Leu Gln Phe Pro Val Gly Arg Val His Arg Leu Leu
                85                  90                  95

Arg Lys Gly Ser Arg Gly Lys Gln Gly Gly Lys Ala Arg Ala Lys Ala
            100                 105                 110

Lys Thr Arg Ser Ser Arg Ala Gly Leu Gln Phe Pro Val Gly Arg Val
            115                 120                 125

His Arg Leu Leu Arg Lys Ser Gly Arg Gly Lys Gln Gly Gly Lys Ala
        130                 135                 140

Arg Ala Lys Ala Lys Thr Arg Ser Ser Arg Ala Gly Leu Gln Phe Pro
145                 150                 155                 160
```

Val Gly Arg Val His Arg Leu Leu Arg Lys Gly Gly Trp Glu Ala
            165                 170                 175

Ala Leu Ala Glu Ala Leu Ala Glu Ala Leu Ala Glu His Leu Ala Glu
        180                 185                 190

Ala Leu Ala Glu Ala Leu Glu Ala Leu Ala Ala
        195                 200

<210> SEQ ID NO 11
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asn Gly Tyr Glu Ile Glu Trp Tyr Ser Trp Val Thr His Gly Met Tyr
1               5                   10                  15

Gly Gly Gly Ser Gly Gly Gly Ser Gly Gly Ser Gly Arg Gly Lys
            20                  25                  30

Gln Gly Gly Lys Ala Arg Ala Lys Ala Lys Thr Arg Ser Ser Arg Ala
        35                  40                  45

Gly Leu Gln Phe Pro Val Gly Arg Val His Arg Leu Leu Arg Lys Ser
    50                  55                  60

Gly Arg Gly Lys Gln Gly Gly Lys Ala Arg Ala Lys Ala Lys Thr Arg
65                  70                  75                  80

Ser Ser Arg Ala Gly Leu Gln Phe Pro Val Gly Arg Val His Arg Leu
                85                  90                  95

Leu Arg Lys Gly Ser Arg Gly Lys Gln Gly Gly Lys Ala Arg Ala Lys
            100                 105                 110

Ala Lys Thr Arg Ser Ser Arg Ala Gly Leu Gln Phe Pro Val Gly Arg
        115                 120                 125

Val His Arg Leu Leu Arg Lys Ser Gly Arg Gly Lys Gln Gly Gly Lys
    130                 135                 140

Ala Arg Ala Lys Ala Lys Thr Arg Ser Ser Arg Ala Gly Leu Gln Phe
145                 150                 155                 160

Pro Val Gly Arg Val His Arg Leu Leu Arg Lys Gly Gly Gly Trp Glu
                165                 170                 175

Ala Ala Leu Ala Glu Ala Leu Ala Glu Ala Leu Ala Glu His Leu Ala
            180                 185                 190

Glu Ala Leu Ala Glu Ala Leu Glu Ala Leu Ala Ala
        195                 200

<210> SEQ ID NO 12
<211> LENGTH: 23
<212> TYPE: PRT
<213> ORGANISM: Influenza virus

<400> SEQUENCE: 12

Gly Leu Phe Glu Ala Ile Glu Gly Phe Ile Glu Asn Gly Trp Glu Gly
1               5                   10                  15

Met Ile Asp Gly Trp Tyr Gly
            20

<210> SEQ ID NO 13
<211> LENGTH: 30
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 13

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Trp Glu Ala Arg Leu Ala Arg Ala Leu Ala Arg Ala Leu Ala Arg His
1               5                   10                  15

Leu Ala Arg Ala Leu Ala Arg Ala Leu Arg Ala Gly Glu Ala
            20                  25                  30

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Leu Phe His Ala Ile Ala His Phe Ile His Gly Gly Trp His Gly
1               5                   10                  15

Leu Ile His Gly Trp Tyr Gly
            20

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Trp Glu Ala Ala Leu Ala Glu Ala Glu Ala Leu Ala Leu Ala Glu Lys
1               5                   10                  15

Glu Ala Leu Ala Leu Ala Glu Ala Glu Leu Ala Leu Ala Ala
            20                  25                  30

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30
```

Pro Arg Thr Glu Ser
        35

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Gln Leu Pro Leu Ala Thr
1               5

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr His Trp Tyr Gly Tyr Thr Pro Gln Asn Val Ile
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Pro Leu Pro Pro Pro Ser Arg Pro Phe Phe Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Gly Asp Ser Pro Ala Ser Ser Lys Pro
1               5                   10

<210> SEQ ID NO 22
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser Gly Gly Gly Ser Gly Gly Gly Ser Gly Gly Gly
        35                  40                  45

```
Ser Gly Arg Gly Lys Gln Gly Gly Lys Ala Arg Ala Lys Ala Lys Thr
    50                  55                  60

Arg Ser Ser Arg Ala Gly Leu Gln Phe Pro Val Gly Arg Val His Arg
65                  70                  75                  80

Leu Leu Arg Lys Ser Gly Arg Gly Lys Gln Gly Gly Lys Ala Arg Ala
                85                  90                  95

Lys Ala Lys Thr Arg Ser Ser Arg Ala Gly Leu Gln Phe Pro Val Gly
            100                 105                 110

Arg Val His Arg Leu Leu Arg Lys Ser Gly Arg Gly Lys Gln Gly Gly
            115                 120                 125

Lys Ala Arg Ala Lys Ala Lys Thr Arg Ser Ser Arg Ala Gly Leu Gln
        130                 135                 140

Phe Pro Val Gly Arg Val His Arg Leu Leu Arg Lys Ser Gly Arg Gly
145                 150                 155                 160

Lys Gln Gly Gly Lys Ala Arg Ala Lys Ala Lys Thr Arg Ser Ser Arg
                165                 170                 175

Ala Gly Leu Gln Phe Pro Val Gly Arg Val His Arg Leu Leu Arg Lys
            180                 185                 190

Gly Gly Gly Trp Glu Ala Ala Leu Ala Glu Ala Leu Ala Glu Ala Leu
            195                 200                 205

Ala Glu His Leu Ala Glu Ala Leu Ala Glu Ala Leu Glu Ala Leu Ala
            210                 215                 220

Ala
225

<210> SEQ ID NO 23
<211> LENGTH: 195
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Gln Leu Pro Leu Ala Thr Gly Gly Ser Gly Gly Gly Ser Gly
1               5                   10                  15

Gly Gly Ser Gly Arg Gly Lys Gln Gly Gly Lys Ala Arg Ala Lys Ala
                20                  25                  30

Lys Thr Arg Ser Ser Arg Ala Gly Leu Gln Phe Pro Val Gly Arg Val
            35                  40                  45

His Arg Leu Leu Arg Lys Ser Gly Arg Gly Lys Gln Gly Gly Lys Ala
    50                  55                  60

Arg Ala Lys Ala Lys Thr Arg Ser Ser Arg Ala Gly Leu Gln Phe Pro
65                  70                  75                  80

Val Gly Arg Val His Arg Leu Leu Arg Lys Ser Gly Arg Gly Lys Gln
                85                  90                  95

Gly Gly Lys Ala Arg Ala Lys Ala Lys Thr Arg Ser Ser Arg Ala Gly
            100                 105                 110

Leu Gln Phe Pro Val Gly Arg Val His Arg Leu Leu Arg Lys Ser Gly
            115                 120                 125

Arg Gly Lys Gln Gly Gly Lys Ala Arg Ala Lys Ala Lys Thr Arg Ser
        130                 135                 140

Ser Arg Ala Gly Leu Gln Phe Pro Val Gly Arg Val His Arg Leu Leu
145                 150                 155                 160

Arg Lys Gly Gly Gly Trp Glu Ala Ala Leu Ala Glu Ala Leu Ala Glu
```

```
                    165                 170                 175

Ala Leu Ala Glu His Leu Ala Glu Ala Leu Ala Glu Ala Leu Glu Ala
                180                 185                 190

Leu Ala Ala
        195

<210> SEQ ID NO 24
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Tyr His Trp Tyr Gly Tyr Thr Pro Gln Asn Val Ile Gly Gly Gly Ser
1               5                   10                  15

Gly Gly Gly Ser Gly Gly Gly Ser Gly Arg Gly Lys Gln Gly Gly Lys
                20                  25                  30

Ala Arg Ala Lys Ala Lys Thr Arg Ser Ser Arg Ala Gly Leu Gln Phe
            35                  40                  45

Pro Val Gly Arg Val His Arg Leu Leu Arg Lys Ser Gly Arg Gly Lys
        50                  55                  60

Gln Gly Gly Lys Ala Arg Ala Lys Ala Lys Thr Arg Ser Ser Arg Ala
65                  70                  75                  80

Gly Leu Gln Phe Pro Val Gly Arg Val His Arg Leu Leu Arg Lys Gly
                85                  90                  95

Ser Arg Gly Lys Gln Gly Gly Lys Ala Arg Ala Lys Ala Lys Thr Arg
                100                 105                 110

Ser Ser Arg Ala Gly Leu Gln Phe Pro Val Gly Arg Val His Arg Leu
            115                 120                 125

Leu Arg Lys Ser Gly Arg Gly Lys Gln Gly Gly Lys Ala Arg Ala Lys
        130                 135                 140

Ala Lys Thr Arg Ser Ser Arg Ala Gly Leu Gln Phe Pro Val Gly Arg
145                 150                 155                 160

Val His Arg Leu Leu Arg Lys Gly Gly Gly Trp Glu Ala Ala Leu Ala
                165                 170                 175

Glu Ala Leu Ala Glu Ala Leu Glu His Leu Ala Glu Ala Leu Glu Ala
                180                 185                 190

Glu Ala Leu Glu Ala Leu Ala Ala
            195                 200

<210> SEQ ID NO 25
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ile Pro Leu Pro Pro Ser Arg Pro Phe Phe Lys Gly Gly Gly Gly Ser
1               5                   10                  15

Gly Gly Gly Ser Gly Gly Gly Ser Gly Arg Gly Lys Gln Gly Gly Lys
                20                  25                  30

Ala Arg Ala Lys Ala Lys Thr Arg Ser Ser Arg Ala Gly Leu Gln Phe
            35                  40                  45

Pro Val Gly Arg Val His Arg Leu Leu Arg Lys Ser Gly Arg Gly Lys
```

```
                50                  55                  60
Gln Gly Gly Lys Ala Arg Ala Lys Ala Lys Thr Arg Ser Ser Arg Ala
 65                  70                  75                  80

Gly Leu Gln Phe Pro Val Gly Arg Val His Arg Leu Leu Arg Lys Gly
                 85                  90                  95

Ser Arg Gly Lys Gln Gly Gly Lys Ala Arg Ala Lys Ala Lys Thr Arg
                100                 105                 110

Ser Ser Arg Ala Gly Leu Gln Phe Pro Val Gly Arg Val His Arg Leu
                115                 120                 125

Leu Arg Lys Ser Gly Arg Gly Lys Gln Gly Gly Lys Ala Arg Ala Lys
            130                 135                 140

Ala Lys Thr Arg Ser Ser Arg Ala Gly Leu Gln Phe Pro Val Gly Arg
145                 150                 155                 160

Val His Arg Leu Leu Arg Lys Gly Gly Trp Glu Ala Ala Leu Ala
                165                 170                 175

Glu Ala Leu Ala Glu Ala Leu Ala Glu His Leu Ala Glu Ala Leu Ala
                180                 185                 190

Glu Ala Leu Glu Ala Leu Ala Ala
            195                 200

<210> SEQ ID NO 26
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Arg Gly Asp Ser Pro Ala Ser Ser Lys Pro Gly Gly Gly Ser Gly Gly
  1               5                  10                  15

Gly Ser Gly Gly Gly Ser Gly Arg Gly Lys Gln Gly Gly Lys Ala Arg
                 20                  25                  30

Ala Lys Ala Lys Thr Arg Ser Ser Arg Ala Gly Leu Gln Phe Pro Val
             35                  40                  45

Gly Arg Val His Arg Leu Leu Arg Lys Ser Gly Arg Gly Lys Gln Gly
         50                  55                  60

Gly Lys Ala Arg Ala Lys Ala Lys Thr Arg Ser Ser Arg Ala Gly Leu
 65                  70                  75                  80

Gln Phe Pro Val Gly Arg Val His Arg Leu Leu Arg Lys Gly Ser Arg
                 85                  90                  95

Gly Lys Gln Gly Gly Lys Ala Arg Ala Lys Ala Lys Thr Arg Ser Ser
                100                 105                 110

Arg Ala Gly Leu Gln Phe Pro Val Gly Arg Val His Arg Leu Leu Arg
                115                 120                 125

Lys Ser Gly Arg Gly Lys Gln Gly Gly Lys Ala Arg Ala Lys Ala Lys
            130                 135                 140

Thr Arg Ser Ser Arg Ala Gly Leu Gln Phe Pro Val Gly Arg Val His
145                 150                 155                 160

Arg Leu Leu Arg Lys Gly Gly Trp Glu Ala Ala Leu Ala Glu Ala
                165                 170                 175

Leu Ala Glu Ala Leu Ala Glu His Leu Ala Glu Ala Leu Ala Glu Ala
            180                 185                 190

Leu Glu Ala Leu Ala Ala
            195
```

```
<210> SEQ ID NO 27
<211> LENGTH: 16
<212> TYPE: PRT
<213> ORGANISM: Homo sapiens

<400> SEQUENCE: 27

Arg Lys Lys Arg Arg Arg Glu Ser Arg Lys Arg Arg Glu Ser
1               5                   10                  15

<210> SEQ ID NO 28
<211> LENGTH: 17
<212> TYPE: PRT
<213> ORGANISM: Homo sapiens

<400> SEQUENCE: 28

Gly Arg Pro Arg Glu Ser Gly Lys Lys Arg Lys Arg Lys Arg Leu Lys
1               5                   10                  15

Pro

<210> SEQ ID NO 29
<211> LENGTH: 15
<212> TYPE: PRT
<213> ORGANISM: Homo sapiens

<400> SEQUENCE: 29

Gly Lys Arg Lys Lys Lys Gly Lys Leu Gly Lys Lys Arg Asp Pro
1               5                   10                  15

<210> SEQ ID NO 30
<211> LENGTH: 17
<212> TYPE: PRT
<213> ORGANISM: Homo sapiens

<400> SEQUENCE: 30

Gly Lys Arg Lys Lys Lys Gly Lys Leu Gly Lys Lys Arg Pro Arg Ser
1               5                   10                  15

Arg

<210> SEQ ID NO 31
<211> LENGTH: 18
<212> TYPE: PRT
<213> ORGANISM: Homo sapiens

<400> SEQUENCE: 31

Arg Lys Lys Arg Arg Arg Glu Ser Arg Arg Ala Arg Arg Ser Pro Arg
1               5                   10                  15

His Leu

<210> SEQ ID NO 32
<211> LENGTH: 19
<212> TYPE: PRT
<213> ORGANISM: Homo sapiens

<400> SEQUENCE: 32

Ser Arg Arg Ala Arg Arg Ser Pro Arg Glu Ser Gly Lys Lys Arg Lys
1               5                   10                  15

Arg Lys Arg

<210> SEQ ID NO 33
<211> LENGTH: 19
<212> TYPE: PRT
<213> ORGANISM: Homo sapiens
```

<400> SEQUENCE: 33

Val Lys Arg Gly Leu Lys Leu Arg His Val Arg Pro Arg Val Thr Arg
1               5                   10                  15

Met Asp Val

<210> SEQ ID NO 34
<211> LENGTH: 14
<212> TYPE: PRT
<213> ORGANISM: Homo sapiens

<400> SEQUENCE: 34

Ser Arg Arg Ala Arg Arg Ser Pro Arg His Leu Gly Ser Gly
1               5                   10

<210> SEQ ID NO 35
<211> LENGTH: 16
<212> TYPE: PRT
<213> ORGANISM: Homo sapiens

<400> SEQUENCE: 35

Leu Arg Arg Glu Arg Gln Ser Arg Leu Arg Arg Glu Arg Gln Ser Arg
1               5                   10                  15

<210> SEQ ID NO 36
<211> LENGTH: 22
<212> TYPE: PRT
<213> ORGANISM: Homo sapiens

<400> SEQUENCE: 36

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 37
<211> LENGTH: 9
<212> TYPE: PRT
<213> ORGANISM: Human immunodeficiency virus 1

<400> SEQUENCE: 37

Arg Lys Lys Arg Arg Gln Arg Arg Arg
1               5

<210> SEQ ID NO 38
<211> LENGTH: 15
<212> TYPE: PRT
<213> ORGANISM: Flock House virus

<400> SEQUENCE: 38

Arg Arg Arg Arg Asn Arg Thr Arg Arg Asn Arg Arg Arg Val Arg
1               5                   10                  15

<210> SEQ ID NO 39
<211> LENGTH: 17
<212> TYPE: PRT
<213> ORGANISM: Human immunodeficiency virus 1

<400> SEQUENCE: 39

Thr Arg Gln Ala Arg Arg Asn Arg Arg Arg Arg Trp Arg Glu Arg Gln
1               5                   10                  15

Arg

```
<210> SEQ ID NO 40
<211> LENGTH: 13
<212> TYPE: PRT
<213> ORGANISM: Unknown
<220> FEATURE:
<223> OTHER INFORMATION: Description of Unknown:
      Human T-cell leukemia virus II sequence

<400> SEQUENCE: 40

Thr Arg Arg Gln Arg Thr Arg Arg Ala Arg Arg Asn Arg
1               5                   10

<210> SEQ ID NO 41
<211> LENGTH: 19
<212> TYPE: PRT
<213> ORGANISM: Brome Mosaic virus

<400> SEQUENCE: 41

Lys Met Thr Arg Ala Gln Arg Arg Ala Ala Ala Arg Arg Asn Arg Trp
1               5                   10                  15

Thr Ala Arg

<210> SEQ ID NO 42
<211> LENGTH: 17
<212> TYPE: PRT
<213> ORGANISM: Unknown
<220> FEATURE:
<223> OTHER INFORMATION: Description of Unknown:
      P22 N baceriophage sequence

<400> SEQUENCE: 42

Asn Ala Lys Thr Arg Arg His Glu Arg Arg Arg Lys Leu Ala Ile Glu
1               5                   10                  15

Arg

<210> SEQ ID NO 43
<211> LENGTH: 22
<212> TYPE: PRT
<213> ORGANISM: Unknown
<220> FEATURE:
<223> OTHER INFORMATION: Description of Unknown:
      lamda N(1-22) baceriophage sequence

<400> SEQUENCE: 43

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 44
<211> LENGTH: 18
<212> TYPE: PRT
<213> ORGANISM: Unknown
<220> FEATURE:
<223> OTHER INFORMATION: Description of Unknown:
      phi 21N(12-29) baceriophage sequence

<400> SEQUENCE: 44

Thr Ala Lys Thr Arg Tyr Lys Ala Arg Arg Ala Glu Leu Ile Ala Glu
1               5                   10                  15

Arg Arg

<210> SEQ ID NO 45
<211> LENGTH: 16
```

```
<212> TYPE: PRT
<213> ORGANISM: Saccharomyces sp.

<400> SEQUENCE: 45

Thr Arg Arg Asn Lys Arg Asn Arg Ile Gln Glu Gln Leu Asn Arg Lys
1               5                   10                  15

<210> SEQ ID NO 46
<211> LENGTH: 32
<212> TYPE: PRT
<213> ORGANISM: Homo sapiens

<400> SEQUENCE: 46

Pro Arg Arg Arg Arg Ser Ser Ser Arg Pro Val Arg Arg Arg Arg Arg
1               5                   10                  15

Pro Arg Val Ser Arg Arg Arg Arg Arg Gly Gly Arg Arg Arg Arg
            20                  25                  30

<210> SEQ ID NO 47
<211> LENGTH: 28
<212> TYPE: PRT
<213> ORGANISM: Homo sapiens

<400> SEQUENCE: 47

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg
            20                  25

<210> SEQ ID NO 48
<211> LENGTH: 26
<212> TYPE: PRT
<213> ORGANISM: Homo sapiens

<400> SEQUENCE: 48

Lys Arg Arg Ile Arg Arg Glu Arg Asn Lys Met Ala Ala Ala Lys Ser
1               5                   10                  15

Arg Asn Arg Arg Arg Glu Leu Thr Asp Thr
            20                  25

<210> SEQ ID NO 49
<211> LENGTH: 22
<212> TYPE: PRT
<213> ORGANISM: Saccharomyces sp.

<400> SEQUENCE: 49

Lys Arg Ala Arg Asn Thr Glu Ala Ala Arg Arg Ser Arg Ala Arg Lys
1               5                   10                  15

Leu Gln Arg Met Lys Gln
            20

<210> SEQ ID NO 50
<211> LENGTH: 16
<212> TYPE: PRT
<213> ORGANISM: Drosophila sp.

<400> SEQUENCE: 50

Arg Gln Ile Lys Ile Trp Phe Gln Asn Arg Arg Met Lys Trp Lys Lys
1               5                   10                  15

<210> SEQ ID NO 51
<211> LENGTH: 16
<212> TYPE: PRT
```

-continued

<213> ORGANISM: Homo sapiens

<400> SEQUENCE: 51

Arg Val Ile Arg Val Trp Phe Gln Asn Lys Arg Cys Lys Asp Lys Lys
1               5                   10                  15

<210> SEQ ID NO 52
<211> LENGTH: 60
<212> TYPE: PRT
<213> ORGANISM: Drosophila sp.

<400> SEQUENCE: 52

Ser Lys Arg Thr Arg Gln Thr Tyr Thr Arg Tyr Gln Thr Leu Glu Leu
1               5                   10                  15

Glu Lys Glu Phe His Phe Asn Arg Tyr Ile Thr Arg Arg Arg Ile
            20                  25                  30

Asp Ile Ala Asn Ala Leu Ser Leu Ser Glu Arg Gln Ile Lys Ile Trp
        35                  40                  45

Phe Gln Asn Arg Arg Met Lys Ser Lys Lys Asp Arg
    50                  55                  60

<210> SEQ ID NO 53
<211> LENGTH: 16
<212> TYPE: PRT
<213> ORGANISM: Homo sapiens

<400> SEQUENCE: 53

Ser Gln Ile Lys Ile Trp Phe Gln Asn Lys Arg Ala Lys Ile Lys Lys
1               5                   10                  15

<210> SEQ ID NO 54
<211> LENGTH: 16
<212> TYPE: PRT
<213> ORGANISM: Homo sapiens

<400> SEQUENCE: 54

Arg Gln Val Thr Ile Trp Phe Gln Asn Arg Arg Val Lys Glu Lys Lys
1               5                   10                  15

<210> SEQ ID NO 55
<211> LENGTH: 16
<212> TYPE: PRT
<213> ORGANISM: Homo sapiens

<400> SEQUENCE: 55

Lys Gln Ile Asn Asn Trp Phe Ile Asn Gln Arg Lys Arg His Trp Lys
1               5                   10                  15

<210> SEQ ID NO 56
<211> LENGTH: 16
<212> TYPE: PRT
<213> ORGANISM: Homo sapiens

<400> SEQUENCE: 56

Arg His Ile Lys Ile Trp Phe Gln Asn Arg Arg Met Lys Trp Lys Lys
1               5                   10                  15

<210> SEQ ID NO 57
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Met Gly Leu Gly Leu His Leu Leu Val Leu Ala Ala Ala Leu Gln Gly
1               5                   10                  15

Ala Lys Lys Lys Arg Lys Val
            20

<210> SEQ ID NO 58
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Val Lys Ser Lys Ile Gly Ser Trp Ile Leu Val Leu Phe Val Ala
1               5                   10                  15

Met Trp Ser Asp Val Gly Leu Cys Lys Lys Arg Pro Lys Pro
            20                  25                  30

<210> SEQ ID NO 59
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Ala Val Leu Leu Pro Val Leu Leu Ala Ala Pro Val Gln Arg Lys
1               5                   10                  15

Arg Gln Lys Leu Pro
            20

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Ala Val Leu Leu Pro Val Leu Leu Ala Ala Pro
1               5                   10

<210> SEQ ID NO 62
<211> LENGTH: 24
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 62

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 63
<211> LENGTH: 20
<212> TYPE: PRT
<213> ORGANISM: Pyrrhocoris apterus

<400> SEQUENCE: 63

Val Asp Lys Gly Ser Tyr Leu Pro Arg Pro Thr Pro Pro Arg Pro Ile
1               5                   10                  15

Tyr Asn Arg Asn
            20

<210> SEQ ID NO 64
<211> LENGTH: 22
<212> TYPE: PRT
<213> ORGANISM: Homo sapiens

<400> SEQUENCE: 64

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 65
<211> LENGTH: 21
<212> TYPE: PRT
<213> ORGANISM: Unknown
<220> FEATURE:
<223> OTHER INFORMATION: Description of Unknown:
      Buforin 2 sequence

<400> SEQUENCE: 65

Thr Arg Ser Ser Arg Ala Gly Leu Gln Trp Pro Val Gly Arg Val His
1               5                   10                  15

Arg Leu Leu Arg Lys
            20

<210> SEQ ID NO 66
<211> LENGTH: 26
<212> TYPE: PRT
<213> ORGANISM: Unknown
<220> FEATURE:
<223> OTHER INFORMATION: Description of Unknown:
      Melittin sequence

<400> SEQUENCE: 66

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 67
<211> LENGTH: 23
<212> TYPE: PRT
<213> ORGANISM: Unknown
```

```
<220> FEATURE:
<223> OTHER INFORMATION: Description of Unknown:
      Magainin 2 sequence

<400> SEQUENCE: 67

Gly Ile Gly Lys Trp Leu His Ser Ala Lys Lys Phe Gly Lys Ala Phe
1               5                   10                  15

Val Gly Glu Ile Met Asn Ser
            20

<210> SEQ ID NO 68
<211> LENGTH: 38
<212> TYPE: PRT
<213> ORGANISM: Unknown
<220> FEATURE:
<223> OTHER INFORMATION: Description of Unknown:
      LL-37 sequence

<400> SEQUENCE: 68

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser Cys
        35

<210> SEQ ID NO 69
<211> LENGTH: 18
<212> TYPE: PRT
<213> ORGANISM: Unknown
<220> FEATURE:
<223> OTHER INFORMATION: Description of Unknown:
      SynB1 sequence

<400> SEQUENCE: 69

Arg Gly Gly Arg Leu Ser Tyr Ser Arg Arg Arg Phe Ser Thr Ser Thr
1               5                   10                  15

Gly Arg

<210> SEQ ID NO 70
<211> LENGTH: 14
<212> TYPE: PRT
<213> ORGANISM: Unknown
<220> FEATURE:
<223> OTHER INFORMATION: Description of Unknown:
      Crotamine sequence

<400> SEQUENCE: 70

Tyr Lys Gln Cys His Lys Lys Gly Gly Lys Lys Gly Ser Gly
1               5                   10

<210> SEQ ID NO 71
<211> LENGTH: 20
<212> TYPE: PRT
<213> ORGANISM: Unknown
<220> FEATURE:
<223> OTHER INFORMATION: Description of Unknown:
      S413-PVrev sequence

<400> SEQUENCE: 71

Ala Leu Trp Lys Thr Leu Leu Lys Lys Val Leu Lys Ala Pro Lys Lys
1               5                   10                  15

Lys Arg Lys Val
            20
```

```
<210> SEQ ID NO 72
<211> LENGTH: 20
<212> TYPE: PRT
<213> ORGANISM: Unknown
<220> FEATURE:
<223> OTHER INFORMATION: Description of Unknown:
      L-2 sequence

<400> SEQUENCE: 72

His Ala Arg Ile Lys Pro Thr Phe Arg Arg Leu Lys Trp Lys Tyr Lys
1               5                   10                  15

Gly Lys Phe Trp
            20

<210> SEQ ID NO 73
<211> LENGTH: 22
<212> TYPE: PRT
<213> ORGANISM: Unknown
<220> FEATURE:
<223> OTHER INFORMATION: Description of Unknown:
      Inv3 sequence

<400> SEQUENCE: 73

Thr Lys Arg Arg Ile Thr Pro Lys Asp Val Ile Asp Val Arg Ser Val
1               5                   10                  15

Thr Thr Glu Ile Asn Thr
            20

<210> SEQ ID NO 74
<211> LENGTH: 27
<212> TYPE: PRT
<213> ORGANISM: Unknown
<220> FEATURE:
<223> OTHER INFORMATION: Description of Unknown:
      Erns viral sequence

<400> SEQUENCE: 74

Arg Gln Gly Ala Ala Arg Val Thr Ser Trp Leu Gly Arg Gln Leu Arg
1               5                   10                  15

Ile Ala Gly Lys Arg Leu Glu Gly Arg Ser Lys
            20                  25

<210> SEQ ID NO 75
<211> LENGTH: 34
<212> TYPE: PRT
<213> ORGANISM: Unknown
<220> FEATURE:
<223> OTHER INFORMATION: Description of Unknown:
      VP22 viral sequence

<400> SEQUENCE: 75

Asn Ala Ala Thr Ala Thr Arg Gly Arg Ser Ala Ala Ser Arg Pro Thr
1               5                   10                  15

Gln Arg Pro Arg Ala Pro Ala Arg Ser Ala Ser Arg Pro Arg Arg Pro
            20                  25                  30

Val Gln

<210> SEQ ID NO 76
<211> LENGTH: 16
<212> TYPE: PRT
<213> ORGANISM: Human immunodeficiency virus 1

<400> SEQUENCE: 76

Arg His Ser Arg Ile Gly Ile Ile Gln Gln Arg Arg Thr Arg As

<210> SEQ ID NO 77
<211> LENGTH: 29
<212> TYPE: PRT
<213> ORGANISM: Unknown
<220> FEATURE:
<223> OTHER INFORMATION: Description of Unknown:
      Ribotoxin2 L3 loop viral sequence

<400> SEQUENCE: 77

Lys Leu Ile Lys Gly Arg Thr Pro Ile Lys Phe Gly Lys Ala Asp Cys
1               5                   10                  15

Asp Arg Pro Pro Lys His Ser Gln Asn Gly Met Gly Lys
            20                  25

<210> SEQ ID NO 78
<211> LENGTH: 12
<212> TYPE: PRT
<213> ORGANISM: Unknown
<220> FEATURE:
<223> OTHER INFORMATION: Description of Unknown:
      PreS2-TLM viral sequence

<400> SEQUENCE: 78

Pro Leu Ser Ser Ile Phe Ser Arg Ile Gly Asp Pro
1               5                   10

<210> SEQ ID NO 79
<211> LENGTH: 26
<212> TYPE: PRT
<213> ORGANISM: Bos sp.

<400> SEQUENCE: 79

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 80
<211> LENGTH: 10
<212> TYPE: PRT
<213> ORGANISM: Unknown
<220> FEATURE:
<223> OTHER INFORMATION: Description of Unknown:
      HRSV bacterial sequence

<400> SEQUENCE: 80

Arg Arg Ile Pro Asn Arg Arg Pro Arg Arg
1               5                   10

<210> SEQ ID NO 81
<211> LENGTH: 5
<212> TYPE: PRT
<213> ORGANISM: Unknown
<220> FEATURE:
<223> OTHER INFORMATION: Description of Unknown:
      AIP6 bacterial sequence

<400> SEQUENCE: 81

Arg Leu Arg Trp Arg
1               5

<210> SEQ ID NO 82
<211> LENGTH: 22
<212> TYPE: PRT

```
<213> ORGANISM: Unknown
<220> FEATURE:
<223> OTHER INFORMATION: Description of Unknown:
      ARF(1-22) bacterial sequence

<400> SEQUENCE: 82

Met Val Arg Arg Phe Leu Val Thr Leu Arg Ile Arg Arg Ala Cys Gly
1               5                   10                  15

Pro Pro Arg Val Arg Val
            20

<210> SEQ ID NO 83
<211> LENGTH: 22
<212> TYPE: PRT
<213> ORGANISM: Unknown
<220> FEATURE:
<223> OTHER INFORMATION: Description of Unknown:
      M918 bacterial sequence

<400> SEQUENCE: 83

Met Val Thr Val Leu Phe Arg Arg Leu Arg Ile Arg Arg Ala Cys Gly
1               5                   10                  15

Pro Pro Arg Val Arg Val
            20

<210> SEQ ID NO 84
<211> LENGTH: 18
<212> TYPE: PRT
<213> ORGANISM: Unknown
<220> FEATURE:
<223> OTHER INFORMATION: Description of Unknown:
      pVEC bacterial sequence

<400> SEQUENCE: 84

Leu Leu Ile Ile Leu Arg Arg Arg Ile Arg Lys Gln Ala His Ala His
1               5                   10                  15

Ser Lys

<210> SEQ ID NO 85
<211> LENGTH: 18
<212> TYPE: PRT
<213> ORGANISM: Unknown
<220> FEATURE:
<223> OTHER INFORMATION: Description of Unknown:
      Azurin p18 bacterial sequence

<400> SEQUENCE: 85

Leu Ser Thr Ala Ala Asp Met Gln Gly Val Val Thr Asp Gly Met Ala
1               5                   10                  15

Ser Gly

<210> SEQ ID NO 86
<211> LENGTH: 28
<212> TYPE: PRT
<213> ORGANISM: Unknown
<220> FEATURE:
<223> OTHER INFORMATION: Description of Unknown:
      Azurin p28 bacterial sequence

<400> SEQUENCE: 86

Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp
            20                  25
```

```
<210> SEQ ID NO 87
<211> LENGTH: 15
<212> TYPE: PRT
<213> ORGANISM: Unknown
<220> FEATURE:
<223> OTHER INFORMATION: Description of Unknown:
      hCT18-32 bacterial sequence

<400> SEQUENCE: 87

Lys Phe His Thr Phe Pro Gln Thr Ala Ile Gly Val Gly Ala Pro
1               5                   10                  15

<210> SEQ ID NO 88
<211> LENGTH: 5
<212> TYPE: PRT
<213> ORGANISM: Unknown
<220> FEATURE:
<223> OTHER INFORMATION: Description of Unknown:
      Bip bacterial sequence

<400> SEQUENCE: 88

Val Pro Thr Leu Lys
1               5

<210> SEQ ID NO 89
<211> LENGTH: 6
<212> TYPE: PRT
<213> ORGANISM: Unknown
<220> FEATURE:
<223> OTHER INFORMATION: Description of Unknown:
      C105Y bacterial sequence

<400> SEQUENCE: 89

Pro Phe Val Tyr Leu Ile
1               5

<210> SEQ ID NO 90
<211> LENGTH: 10
<212> TYPE: PRT
<213> ORGANISM: Unknown
<220> FEATURE:
<223> OTHER INFORMATION: Description of Unknown:
      FGF12 bacterial sequence

<400> SEQUENCE: 90

Pro Ile Glu Val Cys Met Tyr Arg Glu Pro
1               5                   10

<210> SEQ ID NO 91
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Lys Glu Thr Trp Trp Glu Thr Trp Trp Thr Glu Trp Ser Gln Pro Lys
1               5                   10                  15

Lys Arg Lys Val
            20

<210> SEQ ID NO 92
<211> LENGTH: 27
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 92

Gly Leu Ala Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 93
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 94
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Gly Tyr Leu Leu Gly His Ile Asn Leu His His Leu Ala His Leu
1               5                   10                  15

Ala Ile Asx His His Ile Leu
            20

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Lys Leu Ala Leu Lys Ala Leu Lys Ala Leu Lys Ala Ala Leu Lys Leu
1               5                   10                  15

Ala

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Arg Trp Trp Arg Arg Trp Arg Arg
1               5

<210> SEQ ID NO 97
<211> LENGTH: 20
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 97

Gly Leu Trp Arg Ala Leu Trp Arg Leu Leu Arg Ser Leu Trp Arg Leu
1               5                   10                  15

Leu Trp Arg Ala
            20

<210> SEQ ID NO 98
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 99
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 100
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Leu Lys Thr Leu Thr Glu Thr Leu Lys Glu Leu Thr Lys Thr Leu Thr
1               5                   10                  15

Glu Leu

<210> SEQ ID NO 101
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Leu Ala Leu Gln Leu Ala Leu Gln Ala Leu Gln Ala Ala Leu Gln
1               5                   10                  15

Leu Ala

```
<210> SEQ ID NO 102
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gly Pro Ser Gln Pro Thr Tyr Pro Gly Asp Asp Ala Pro Val Arg Asp
1               5                   10                  15

Leu Ile Arg Phe Tyr Arg Asp Leu Gln Arg Tyr Leu Asn Val Val Thr
            20                  25                  30

Arg His Arg Tyr
        35

<210> SEQ ID NO 103
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gly Pro Ser Gln Pro Thr Tyr Pro Gly Asp Asp Ala Pro Val Arg Asp
1               5                   10                  15

Leu Ile Arg Phe Tyr Arg Asp Leu Arg Arg Tyr Leu Asn Val Val Thr
            20                  25                  30

Arg His Arg Tyr
        35

<210> SEQ ID NO 104
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gly Pro Ser Gln Pro Thr Tyr Pro Gly Asp Asp Ala Pro Val Arg Asp
1               5                   10                  15

Leu Arg Arg Phe Tyr Arg Asp Leu Arg Arg Tyr Leu Asn Val Val Thr
            20                  25                  30

Arg His Arg Tyr
        35

<210> SEQ ID NO 105
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Val Arg Leu Pro Pro Pro Val Arg Leu Pro Pro Pro Val Arg Leu Pro
1               5                   10                  15

Pro Pro

<210> SEQ ID NO 106
<211> LENGTH: 18
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Val Glu Leu Pro Pro Pro Val Glu Leu Pro Pro Pro Val Glu Leu Pro
1               5                   10                  15

Pro Pro

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Phe Lys Ile Tyr Asp Lys Lys Val Arg Thr Arg Val Val Lys His
1               5                   10                  15

<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Ala Ser Lys Arg Asp Gly Ser Trp Val Lys Lys Leu His Arg Ile
1               5                   10                  15

Leu Glu

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Lys Gly Thr Tyr Lys Lys Lys Leu Met Arg Ile Pro Leu Lys Gly Thr
1               5                   10                  15

<210> SEQ ID NO 110
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Leu Tyr Lys Lys Gly Pro Ala Lys Lys Gly Arg Pro Pro Leu Arg Gly
1               5                   10                  15

Trp Phe His

<210> SEQ ID NO 111
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 111

His Ser Pro Ile Ile Pro Leu Gly Thr Arg Phe Val Cys His Gly Val
1               5                   10                  15
Thr

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Tyr Thr Ala Ile Ala Trp Val Lys Ala Phe Ile Arg Lys Leu Arg Lys
1               5                   10                  15

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ile Ala Trp Val Lys Ala Phe Ile Arg Lys Leu Arg Lys Gly Pro Leu
1               5                   10                  15
Gly

<210> SEQ ID NO 114
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ile Ala Trp Val Lys Ala Phe Ile Arg Lys Leu Arg Lys Gly Pro Leu
1               5                   10                  15
Gly

<210> SEQ ID NO 115
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Leu Ser Gly Met Asn Glu Val Leu Ser Phe Arg Trp Leu
1               5                   10

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 116

Ser Asp Leu Trp Glu Met Met Met Val Ser Leu Ala Cys Gln Tyr
1               5                   10                  15

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Val Thr Trp Thr Pro Gln Ala Trp Phe Gln Trp Val
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Ser Pro Trp Gly Leu Gln His His Pro Pro Arg Thr
1               5                   10

<210> SEQ ID NO 119
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Pro Phe His Phe Tyr Gln Phe Leu Phe Pro Pro Val
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Thr Ser Pro Leu Asn Ile His Asn Gly Gln Lys Leu
1               5                   10

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Cys Ala Tyr His Arg Leu Arg Arg Cys
1               5

<210> SEQ ID NO 122
<211> LENGTH: 18
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 122

Arg Cys Gly Arg Ala Ser Arg Cys Arg Val Arg Trp Met Arg Arg Arg
1               5                   10                  15

Arg Ile

<210> SEQ ID NO 123
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Pro Tyr Ser Arg Pro His Val Gln Leu Trp Tyr Pro Asn Arg Glu Ser
1               5                   10                  15

Cys Arg Ser Leu Ile Arg Ser Leu Gly Pro
            20                  25

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Pro Leu Ile Leu Leu Arg Leu Leu Arg Gly Gln Phe
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Pro Leu Ile Tyr Leu Arg Leu Leu Arg Gly Gln Phe
1               5                   10

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Lys Leu Trp Met Arg Trp Tyr Ser Pro Thr Thr Arg Arg Tyr Gly
1               5                   10                  15

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 127

Asp His Leu Ala Ser Leu Trp Trp Gly Thr Glu Leu
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Asn Tyr Ser Lys Pro Thr Asp Arg Gln Tyr His Phe
1               5                   10

<210> SEQ ID NO 129
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Cys Ala Gln Lys Leu Asp Gly Cys Ser Tyr Ile Ser Trp Ser Cys
1               5                   10                  15

Gly

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ala Cys Ser Gly Trp Trp Pro Lys Cys Gln Gly Tyr Ile Pro Gly Cys
1               5                   10                  15

Gly

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Cys Ala Pro Gly Val Tyr Arg Cys Asn Gln Asn Phe Ile Trp Cys
1               5                   10                  15

Gly

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ile Pro Leu Pro Pro Pro Ser Arg Pro Phe Phe Lys
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Leu Met Asn Pro Asn Asn His Pro Arg Thr Pro Arg
1               5                   10

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Cys His His Asn Leu Thr His Ala Cys
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Cys Leu His His Tyr His Gly Ser Cys
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Cys His His Ala Leu Thr His Ala Cys
1               5

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Pro Arg Pro Arg His Thr Leu Arg Leu Ser Leu
1               5                   10

<210> SEQ ID NO 138
<211> LENGTH: 12
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 138

Thr Met Gly Phe Thr Ala Pro Arg Phe Pro His Tyr
1               5                   10

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Arg Met Trp Pro Ser Ser Thr Val Asn Leu Ser Ala Gly Arg Arg
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asn Gly Tyr Glu Ile Glu Trp Tyr Ser Trp Val Thr His Gly Met Tyr
1               5                   10                  15

<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Phe Arg Ser Phe Glu Ser Cys Leu Ala Lys Ser His
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Tyr His Trp Tyr Gly Tyr Thr Pro Gln Asn Val Ile
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gln His Tyr Asn Ile Val Asn Thr Gln Ser Arg Val
1               5                   10

```
<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gln Arg His Lys Pro Arg Glu
1               5

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

His Ser Gln Ala Ala Val Pro
1               5

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ala Gly Asn Trp Thr Pro Ile
1               5

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Pro Leu Leu Gln Ala Thr Leu
1               5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Leu Ser Leu Ile Thr Arg Leu
1               5

<210> SEQ ID NO 149
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149
```

```
Cys Arg Gly Asp Cys Leu
1               5
```

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

```
Gly Ala Cys Arg Gly Asp Cys Leu Gly Ala
1               5                   10
```

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

```
Cys Arg Arg Glu Thr Ala Trp Ala Cys
1               5
```

<210> SEQ ID NO 152
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

```
Gly Ala Cys Arg Arg Glu Thr Ala Trp Ala Cys Gly Ala
1               5                   10
```

<210> SEQ ID NO 153
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

```
Val Ser Trp Phe Ser Arg His Arg Tyr Ser Pro Phe Ala Val Ser
1               5                   10                  15
```

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

```
Cys Asp Cys Arg Gly Asp Cys Phe Cys
1               5
```

<210> SEQ ID NO 155
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 155

Arg Thr Asp Leu Asp Ser Leu Arg Thr Tyr Thr Leu
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Cys Thr Thr His Trp Gly Phe Thr Leu Cys
1               5                   10

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ala Pro Ser Pro Met Ile Trp
1               5

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Trp Thr Leu Tyr Thr Pro Ser Gly Gln Ser Lys
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ser Trp Glu Leu Tyr Tyr Pro Leu Arg Ala Asn Leu
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Trp Gln Pro Asp Thr Ala His His Trp Ala Thr Leu
1               5                   10
```

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Cys Ser Asp Ser Trp His Tyr Trp Cys
1               5

<210> SEQ ID NO 162
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Trp His Trp Leu Pro Asn Leu Arg His Tyr Ala Ser
1               5                   10

<210> SEQ ID NO 163
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Trp His Thr Glu Ile Leu Lys Ser Tyr Pro His Glu Asx
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Tyr Asn Thr Asn His Val Pro Leu Ser Pro Lys Tyr
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Tyr Ser Ala Tyr Pro Asp Ser Val Pro Met Met Ser
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 166

Thr Asn Tyr Leu Phe Ser Pro Asn Gly Pro Ile Ala
1               5                   10

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Cys Leu Ser Tyr Tyr Pro Ser Tyr Cys
1               5

<210> SEQ ID NO 168
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (9)..(16)
<223> OTHER INFORMATION: Intrachain disulfide bond between Cys residues

<400> SEQUENCE: 168

Ala Cys Ser Leu Gln Asp Pro Asn Cys Asp Trp Trp Gly His Tyr Cys
1               5                   10                  15

Gly

<210> SEQ ID NO 169
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Cys Gly Leu Gln Gly Tyr Gly Cys Trp Gly Met Tyr Gly Lys Cys
1               5                   10                  15

Gly

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Cys Val Gly Val Leu Pro Ser Gln Asp Ala Ile Gly Ile Cys
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171
```

```
Cys Gly Pro Leu Pro Val Asp Trp Tyr Trp Cys
1               5                   10
```

<210> SEQ ID NO 172
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

```
Cys Glu Trp Lys Phe Asp Pro Gly Leu Gly Gln Ala Arg Cys
1               5                   10
```

<210> SEQ ID NO 173
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

```
Cys Asp Tyr Met Thr Asp Gly Arg Ala Ala Ser Lys Ile Cys
1               5                   10
```

<210> SEQ ID NO 174
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

```
Lys Cys Cys Tyr Ser Leu
1               5
```

<210> SEQ ID NO 175
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

```
Met Ala Arg Ser Gly Leu
1               5
```

<210> SEQ ID NO 176
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

```
Trp Thr Gly Trp Cys Leu Asn Pro Glu Glu Ser Thr Trp Gly Phe Cys
1               5                   10                  15

Thr Gly Ser Phe
            20
```

<210> SEQ ID NO 177

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Met Cys Gly Val Cys Leu Ser Ala Gln Arg Trp Thr
1               5                   10

<210> SEQ ID NO 178
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ser Gly Leu Trp Trp Leu Gly Val Asp Ile Leu Gly
1               5                   10

<210> SEQ ID NO 179
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asn Pro Gly Thr Cys Lys Asp Lys Trp Ile Glu Cys Leu Leu Asn Gly
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Asp Pro Arg His Cys Gln Lys Arg Val Leu Pro Cys Pro Ala Trp Leu
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Phe Arg Glu Arg Cys Asp Lys His Pro Gln Lys Cys Thr Lys Phe Leu
1               5                   10                  15

<210> SEQ ID NO 182
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182
```

```
Gly Gly Val Ser Cys Met Gln Thr Ser Pro Val Cys Glu Asn Asn Leu
1               5                   10                  15
```

<210> SEQ ID NO 183
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

```
Ala Asn Thr Pro Cys Gly Pro Tyr Thr His Asp Cys Pro Val Lys Arg
1               5                   10                  15
```

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

```
Pro Gln Asn Ser Lys Ile Pro Gly Pro Thr Phe Leu Asp Pro His
1               5                   10                  15
```

<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

```
Ile Val Trp His Arg Trp Tyr Ala Trp Ser Pro Ala Ser Arg Ile
1               5                   10                  15
```

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

```
His Gly Arg Phe Ile Leu Pro Trp Trp Tyr Ala Phe Ser Pro Ser
1               5                   10                  15
```

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

```
Cys Gly Leu Ile Ile Gln Lys Asn Glu Cys
1               5                   10
```

<210> SEQ ID NO 188
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 188

Cys Asn Ala Gly Glu Ser Ser Lys Asn Cys
1               5                   10

<210> SEQ ID NO 189
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ala Glu Ser Gly Asp Asp Tyr Cys Val Leu Val Phe Thr Asp Ser Ala
1               5                   10                  15

Trp Thr Lys Ile Cys Asp Trp Ser His Phe Arg Asn
            20                  25

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Met Gln Leu Pro Leu Ala Thr
1               5

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Cys Arg Ala Leu Leu Arg Gly Ala Pro Phe His Leu Ala Glu Cys
1               5                   10                  15

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ile Glu Leu Leu Gln Ala Arg
1               5

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Thr Leu Thr Tyr Thr Trp Ser

```
1               5
```

<210> SEQ ID NO 194
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

```
Cys Val Ala Tyr Cys Ile Glu His His Cys Trp Thr Cys
1               5                   10
```

<210> SEQ ID NO 195
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

```
Ala Cys Glu Arg Tyr Gln Gly Cys Phe Ser Val Gly Gly Tyr Cys Gly
1               5                   10                  15
```

<210> SEQ ID NO 196
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

```
Thr His Glu Asn Trp Pro Ala
1               5
```

<210> SEQ ID NO 197
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

```
Trp His Pro Trp Ser Tyr Leu Trp Thr Gln Gln Ala
1               5                   10
```

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

```
Val Leu Trp Leu Lys Asn Arg
1               5
```

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 199

Cys Thr Val Arg Thr Ser Ala Asp Cys
1               5

<210> SEQ ID NO 200
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ala Ala Ala Pro Leu Ala Gln Pro His Met Trp Ala
1               5                   10

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ser His Ser Leu Leu Ser Ser
1               5

<210> SEQ ID NO 202
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ala Leu Trp Pro Pro Asn Leu His Ala Trp Val Pro
1               5                   10

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Leu Thr Val Ser Pro Trp Tyr
1               5

<210> SEQ ID NO 204
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ser Ser Met Asp Ile Val Leu Arg Ala Pro Leu Met
1               5                   10

<210> SEQ ID NO 205

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Phe Pro Met Phe Asn His Trp Glu Gln Trp Pro Pro
1               5                   10

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ser Tyr Pro Ile Pro Asp Thr
1               5

<210> SEQ ID NO 207
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

His Thr Ser Asp Gln Thr Asn
1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Cys Leu Phe Met Arg Leu Ala Trp Cys
1               5

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Asp Met Pro Gly Thr Val Leu Pro
1               5

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210
```

Asp Trp Arg Gly Asp Ser Met Asp Ser
1               5

<210> SEQ ID NO 211
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Val Pro Thr Asp Thr Asp Tyr Ser
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Val Glu Glu Gly Gly Tyr Ile Ala Ala
1               5

<210> SEQ ID NO 213
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Val Thr Trp Thr Pro Gln Ala Trp Phe Gln Trp Val
1               5                   10

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ala Gln Tyr Leu Asn Pro Ser
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Cys Ser Ser Arg Thr Met His His Cys
1               5

<210> SEQ ID NO 216
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 216

Cys Pro Leu Asp Ile Asp Phe Tyr Cys
1               5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Cys Pro Ile Glu Asp Arg Pro Met Cys
1               5

<210> SEQ ID NO 218
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Arg Gly Asp Leu Ala Thr Leu Arg Gln Leu Ala Gln Glu Asp Gly Val
1               5                   10                  15

Val Gly Val Arg
            20

<210> SEQ ID NO 219
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ser Pro Arg Gly Asp Leu Ala Val Leu Gly His Lys
1               5                   10

<210> SEQ ID NO 220
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ser Pro Arg Gly Asp Leu Ala Val Leu Gly His Lys Tyr
1               5                   10

<210> SEQ ID NO 221
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Cys Gln Gln Ser Asn Arg Gly Asp Arg Lys Arg Cys
```

<210> SEQ ID NO 222
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Cys Met Gly Asn Lys Cys Arg Ser Ala Lys Arg Pro
1               5                   10

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Cys Gly Glu Met Gly Trp Val Arg Cys
1               5

<210> SEQ ID NO 224
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gly Phe Arg Phe Gly Ala Leu His Glu Tyr Asn Ser
1               5                   10

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Cys Thr Leu Pro His Leu Lys Met Cys
1               5

<210> SEQ ID NO 226
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ala Ser Gly Ala Leu Ser Pro Ser Arg Leu Asp Thr
1               5                   10

<210> SEQ ID NO 227
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 227

Ser Trp Asp Ile Ala Trp Pro Pro Leu Lys Val Pro
1               5                   10

<210> SEQ ID NO 228
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Cys Thr Val Ala Leu Pro Gly Gly Tyr Val Arg Val Cys
1               5                   10

<210> SEQ ID NO 229
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Glu Thr Ala Pro Leu Ser Thr Met Leu Ser Pro Tyr
1               5                   10

<210> SEQ ID NO 230
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Gly Ile Arg Leu Arg Gly
1               5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Cys Pro Gly Pro Glu Gly Ala Gly Cys
1               5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Cys Gly Arg Arg Ala Gly Gly Ser Cys
1               5

<210> SEQ ID NO 233

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Cys Arg Gly Arg Arg Ser Thr
1               5

<210> SEQ ID NO 234
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Cys Asn Gly Arg Cys Val Ser Gly Cys Ala Gly Arg Cys
1               5                   10

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Cys Gly Asn Lys Arg Thr Arg Gly Cys
1               5

<210> SEQ ID NO 236
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

His Val Gly Gly Ser Ser Val
1               5

<210> SEQ ID NO 237
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Arg Gly Asp Gly Ser Ser Val
1               5

<210> SEQ ID NO 238
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

```
Ser Trp Lys Leu Pro Pro Ser
1               5
```

<210> SEQ ID NO 239
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

```
Cys Arg Gly Asp Lys Arg Gly Pro Asp Cys
1               5                   10
```

<210> SEQ ID NO 240
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

```
Gly Gly Lys Arg Pro Ala Arg
1               5
```

<210> SEQ ID NO 241
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

```
Arg Ile Gly Arg Pro Leu Arg
1               5
```

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

```
Cys Gly Phe Tyr Trp Leu Arg Ser Cys
1               5
```

<210> SEQ ID NO 243
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

```
Arg Pro Ala Arg Pro Ala Arg
1               5
```

<210> SEQ ID NO 244
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 244

Thr Leu Thr Tyr Thr Trp Ser
1               5

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ser Ser Gln Pro Phe Trp Ser
1               5

<210> SEQ ID NO 246
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Tyr Arg Cys Thr Leu Asn Ser Pro Phe Phe Trp Glu Asp Met Thr His
1               5                   10                  15

Glu Cys His Ala
            20

<210> SEQ ID NO 247
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Lys Thr Leu Leu Pro Thr Pro
1               5

<210> SEQ ID NO 248
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly
        35

<210> SEQ ID NO 249
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      6xHis

<400> SEQUENCE: 249

His His His His His His
1               5

<210> SEQ ID NO 250
<211> LENGTH: 5
<212> TYPE: PRT
<213> ORGANISM: Unknown
<220> FEATURE:
<223> OTHER INFORMATION: Description of Unknown:
      Bip bacterial sequence

<400> SEQUENCE: 250

Pro Met Leu Lys Glu
1               5

<210> SEQ ID NO 251
<211> LENGTH: 5
<212> TYPE: PRT
<213> ORGANISM: Unknown
<220> FEATURE:
<223> OTHER INFORMATION: Description of Unknown:
      Bip bacterial sequence

<400> SEQUENCE: 251

Val Pro Ala Leu Arg
1               5

<210> SEQ ID NO 252
<211> LENGTH: 5
<212> TYPE: PRT
<213> ORGANISM: Unknown
<220> FEATURE:
<223> OTHER INFORMATION: Description of Unknown:
      Bip bacterial sequence

<400> SEQUENCE: 252

Val Ser Ala Leu Lys
1               5

<210> SEQ ID NO 253
<211> LENGTH: 5
<212> TYPE: PRT
<213> ORGANISM: Unknown
<220> FEATURE:
<223> OTHER INFORMATION: Description of Unknown:
      Bip bacterial sequence

<400> SEQUENCE: 253

Ile Pro Ala Leu Lys
1               5

<210> SEQ ID NO 254
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Arg Arg Arg Arg Arg Arg Arg Arg
1               5
```

```
<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Arg Arg Arg Arg Arg Arg Arg Arg Arg
1               5

<210> SEQ ID NO 256
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Arg Arg Arg Arg Arg Arg Arg Arg Arg Arg
1               5                   10

<210> SEQ ID NO 257
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Arg Arg Arg Arg Arg Arg Arg Arg Arg Arg Arg Arg
1               5                   10

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Pro Pro Arg Pro Pro Arg Pro Pro Arg
1               5

<210> SEQ ID NO 259
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Pro Pro Arg Pro Pro Arg Pro Pro Arg Pro Pro Arg
1               5                   10

<210> SEQ ID NO 260
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260
```

```
Pro Pro Arg Pro Pro Arg Pro Pro Arg Pro Pro Arg Pro Pro Arg
1               5                   10                  15
```

<210> SEQ ID NO 261
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

```
Pro Pro Arg Pro Pro Arg Pro Pro Arg Pro Pro Arg Pro Pro Arg Pro
1               5                   10                  15

Pro Arg
```

<210> SEQ ID NO 262
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

```
Pro Arg Arg Pro Arg Arg Pro Arg Arg
1               5
```

<210> SEQ ID NO 263
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

```
Pro Arg Arg Pro Arg Arg Pro Arg Arg Pro Arg Arg
1               5                   10
```

<210> SEQ ID NO 264
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

```
Pro Arg Arg Pro Arg Arg Pro Arg Arg Pro Arg Arg Pro Arg Arg
1               5                   10                  15
```

<210> SEQ ID NO 265
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

```
Pro Arg Arg Pro Arg Arg Pro Arg Arg Pro Arg Arg Pro Arg Arg Pro
1               5                   10                  15

Arg Arg
```

```
<210> SEQ ID NO 266
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Leu Pro Ala Phe Phe Val Thr Asn Gln Thr Gln Asp
1               5                   10

<210> SEQ ID NO 267
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Leu Gln Asn Ala Pro Arg Ser
1               5

<210> SEQ ID NO 268
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Met Ala Arg Ala Lys Glu
1               5

<210> SEQ ID NO 269
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Met Ser Arg Thr Met Ser
1               5
```

GENE TRANSFER SYSTEMS FOR STEM CELL ENGINEERING

CROSS-REFERENCE TO RELATED PATENT APPLICATIONS

This application is a U.S. National Phase Application under 35 U.S.C. § 371 of International Patent Application No. PCT/US2018/042909, filed Jul. 19, 2018, and claims the benefit of priority under 35 U.S.C. Section 119(e) of U.S. Application Ser. No. 62/534,300, filed Jul. 19, 2017. The International Application was published on Jan. 24, 2019 as International Publication No. WO 2019/018660 A1.

SEQUENCE LISTING

The instant application contains a Sequence Listing which has been filed electronically in ASCII format and is hereby incorporated by reference in its entirety. Said ASCII copy, created on Jan. 18, 2023, is named 10491_006017-US1_SL.txt and is 89,231 bytes in size.

FIELD OF THE INVENTION

The present invention relates to compositions and methods for delivering a nucleic acid such as a gene into mammalian cells.

BACKGROUND OF THE INVENTION

Stem cells have the ability to self-renew and transform into various cell types in an organism. Due to this unique characteristic, they have been used as a source of donor cells to replace damaged organs. In addition, current evidence indicates that systemically administered mesenchymal stem cells (MSCs) can migrate to primary and metastatic solid tumors and deliver therapeutic molecules to tumor foci[1, 2, 3, 4]. It is envisioned that stem cell-mediated gene delivery could emerge as a strategy to improve the efficacy and minimize the toxicity of various cancer gene therapy approaches[4, 5]. For such purposes, MSCs are first harvested from donors and then genetically modified ex vivo to express a variety of bioactive agents. For example, MSCs can be engineered to express prodrug converting enzymes or antiproliferative, pro-apoptotic, anti-angiogenic agents[6, 7]. The vector that is used for stem cell transfection needs to be highly efficient because the methods to rapidly produce unlimited quantities of undifferentiated stem cells have not yet been perfected. Moreover, stem cells in cell culture change/mutate over time (usually after eight to ten passages), thereby providing a limited window of opportunity for processing.

Vectors that are currently used for stem cell engineering can be categorized into viral (adenovirus, lentivirus, AAV) and non-viral (polymer and lipid based). Adenoviral (Ad) vectors can be used to mediate transient and high-level transgene expression. However, for adenoviral vectors to achieve transduction efficiency beyond 50% in MSCs, the multiplicity of infection (MOI) needs to be increased to >5000. Unfortunately, presence of such large amounts of viral proteins in transfected cells could elicit immune response after implantation into the human body, resulting in rapid clearance of transfected MSCs[8]. Integrating vectors such as lentivirus and AAVs can transfect stem cells efficiently but are marred by the potential for insertional mutagenesis[9]. Consequently, the transfected stem cells require an extensive screening process to ensure safety, which in turn, raises the concern of cost-effectiveness in clinical trials. Electroporation is another method for MSC transfection, but it leads to excessive cell death[10].

Commercially available non-viral vectors based on polymers and lipids bear a positive surface charge and have the ability to condense plasmid DNA (pDNA) into nanosize particles suitable for cellular uptake. While such nanoparticles may not show significant toxicity in terms of impact on metabolic activity, as evaluated by MTT or similar assays, recent studies show that these nanoparticles may cause genotoxicity[11, 12]. This could become notably problematic when dealing with stem cells because such vectors could theoretically turn a normal mesenchymal stem cell into a cancer initiating cell.

As high levels of safety are expected, there is a need for efficient and non-genotoxic systems for engineering stem cells.

BRIEF DESCRIPTION OF THE DRAWINGS

FIG. 2A: Schematics of the fusion polypeptide composed of a fusogenic peptide GALA (G) to disrupt endosomal membranes, a DNA condensing motif with inherent nuclear localization signal (H4) and a HER2 targeting peptide (TP). FIG. 2B: By removing the HER2 targeting peptide and replacing it with VEGFR targeting or cell penetrating peptides, the fusion polypeptide is tailor-made for carrying genes into MSCs. The 3-D structure of each motif was simulated independently by I-TASSER server for protein structure and function prediction[37]. FIG. 2C: The size of the DBV/pEGFP nanocomplexes as determined by dynamic light scattering. FIG. 2D: The surface charge of the DBV/pEGFP nanocomplexes as determined by laser doppler velocimetry. FIG. 2E: The shape of the DBV/pEGFP nanocomplexes captured by TEM. The scale bar is 100 nm (Magnification: 75000×). FIG. 2F: The surface charge analysis of the commercial vectors in complex with pEGFP.

FIG. 3A: Flow cytometry histograms showing the percentage of cells in each phase at different time points (i.e., 16-28 hours). FIG. 3B: Bar chart summarizing the percentage of cell population in each cell cycle phase at different time points. Since the percentages of cells in Sub G1 phase is very low, they are not observable in the bar chart. FIG. 3C: Flow cytometry histogram/dotplots showing the overexpression of VEGFR-1 on the surface of ADSCs, A431 cells and in comparison.

FIGS. 4A-C: Bar charts that quantitatively demonstrate the percentage of transfected cells using DBVs and commercial non-viral and viral vectors. The arrows point at the most efficient vectors. FIGS. 4D-F: Bar charts that demonstrate the impact of DBVs and commercial vectors on the proliferation rate of ADSCs. The arrows highlight the vectors which had high efficiencies (>25%) with acceptable impacts on cell proliferation rate. FIG. 4G: LDH release assay demonstrating the impact of vectors on cell membrane integrity.

FIG. 5A: Evaluation of the impact of the gene delivery systems on the formation of micronuclei in transfected ADSCs. The percentage of micronuclei in untransfected cells is normalized to a one-fold increase and is considered as the negative control. FIG. 5B: The PCR microarray analysis of the dysregulated genes in cells transfected with H4G (0.3 and 0.4 μg pEGFP), Vanta-H4G (0.4 μg pEGFP) and Ad-GFP (MOI: 5K and 50K). Only the upregulated (ur) and downregulated (dr) genes are mentioned in each panel.

FIG. 6A: Fluorescent microscopy images of the differentiated ADSCs. FIG. 6B: Bar chart showing the percentages of differentiated cells in each treated and untreated group using flow cytometry.

FIG. 8A: Transfected ADSCs by commercial non-viral vectors using different amounts of pEGFP. FIG. 8B: Transfected ADSCs by Ad-GFP at different MOIs ranging from 100 to 50,000.

FIGS. 10A-10B show flow cytometry histogram (FIG. 10A) and fluoroscope microscope image (FIG. 10B) of HEK293 cells transfected with H4G/pEGFP nanocomplexes. The percentage of transfected cells is determined by flow cytometry (mean±s.d., n=3).

FIGS. 11A-11C show the transfection efficiency of ADSC cells (VEGFR-1 positive) and U87 (VEGFR-1 negative) cells transfected with Vanta-H4G. FIG. 11A: Flow cytometry histogram of transfected ADSCs (n=3). FIG. 11B: Flow cytometry histogram of transfected U87 cells (n=3). FIG. 11C: Bar chart showing the percentage of transfected cells in each cell line as determined by flow cytometry.

FIGS. 12A-12B show flow cytometry histogram (FIG. 12A) and fluorescent microscope image (FIG. 12B) of SKOV-3 cells transfected with Pep1-H4G carrying 0.5 μg of pEGFP. The percentage of transfected cells is determined by flow cytometry.

FIG. 16A: Bar chart showing the percentage of transfected cells as determined by flow cytometry. FIG. 16B: Bar chart showing the percentage of viable cells as determined by flow cytometry. The data are presented as mean±s.d. (n=3).

Figure 1A:
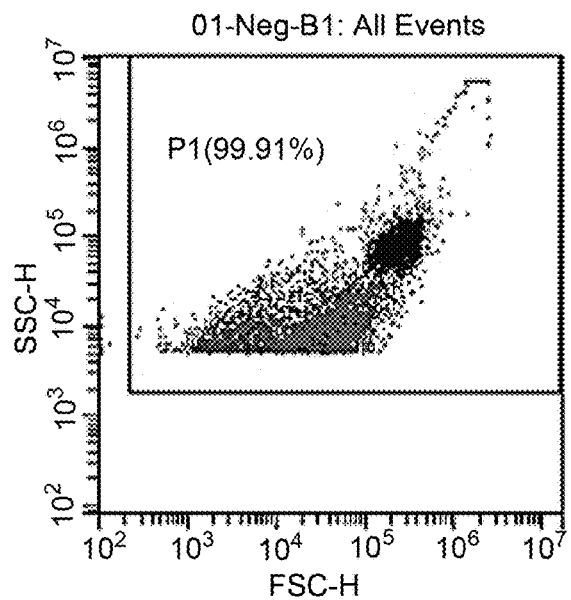
FIGS. 1A-1G show flow cytometry plots for quantification of micronuclei formation in transfected stem cells.

DBV: designer biomimetic vector. As used herein, DBVs are embodiments of the present systems.

SUMMARY

The present disclosure provides for a fusion polypeptide, comprising (or consisting essentially of, or consisting of): (i) a cell surface receptor-binding peptide; (ii) a nucleic acid-binding polypeptide; and (iii) an endosomolytic peptide.

The cell surface receptor-binding peptide may be a vascular endothelial growth factor receptor (VEGFR)-binding peptide, an insulin-like growth factor receptor (IGFR)-binding peptide, a fibroblast growth factor receptor (FGFR)-binding peptide, an epidermal growth factor receptor (EGFR)-binding peptide, a platelet-derived growth factor receptor (PDGFR)-binding peptide, or an integrin-binding peptide.

In certain embodiments, the fusion polypeptide comprises (or consists essentially of, or consists of) an amino acid sequence at least about 70%, at least about 75%, at least about 80%, at least about 85%, at least about 90% identical to the amino acid sequence set forth in SEQ ID NO: 10 or SEQ ID NO: 11.

In certain embodiments, the fusion polypeptide comprises (or consists essentially of, or consists of) an amino acid sequence at least 90% identical to the amino acid sequence set forth in SEQ ID NO: 22, SEQ ID NO: 23, SEQ ID NO: 24, SEQ ID NO: 25, or SEQ ID NO: 26.

In certain embodiments, the fusion polypeptide comprises (or consists essentially of, or consists of) an amino acid sequence at least 90% identical to the amino acid sequence set forth in SEQ ID NO: 7.

In certain embodiments, the cell surface receptor-binding peptide is located at the N-terminus of the fusion polypeptide. In certain embodiments, the endosomolytic peptide is located at the C-terminus of the fusion polypeptide.

The present disclosure provides for a fusion polypeptide, comprising (or consisting essentially of, or consisting of): (i) a cell-penetrating peptide; (ii) a nucleic acid-binding polypeptide; and (iii) an endosomolytic peptide.

In certain embodiments, the cell-penetrating peptide is Pep1. In certain embodiments, the cell-penetrating peptide is MPG.

In certain embodiments, the cell-penetrating peptide comprises (or consists essentially of, or consists of) an amino acid sequence at least about 70%, at least about 75%, at least about 80%, at least about 85%, at least about 90% identical to the amino acid sequence set forth in SEQ ID NO: 3.

In certain embodiments, the cell-penetrating peptide comprises (or consists essentially of, or consists of) an amino acid sequence at least about 70%, at least about 75%, at least about 80%, at least about 85%, at least about 90% identical to the amino acid sequence set forth in SEQ ID NO: 4.

In certain embodiments, the cell-penetrating peptide is located at the N-terminus of the fusion polypeptide. In certain embodiments, the endosomolytic peptide is located at the C-terminus of the fusion polypeptide.

In certain embodiments, the fusion polypeptide comprises (or consists essentially of, or consists of) an amino acid sequence at least about 70%, at least about 75%, at least about 80%, at least about 85%, at least about 90% identical to the amino acid sequence set forth in SEQ ID NO: 8 or SEQ ID NO: 9.

In certain embodiments, the VEGFR-binding peptide is an antagonist of VEGFR. In certain embodiments, the VEGFR-binding peptide is an agonist of VEGFR.

In certain embodiments, the VEGFR-binding peptide comprises (or consists essentially of, or consists of) an amino acid sequence at least about 70%, at least about 75%, at least about 80%, at least about 85%, at least about 90% identical to the amino acid sequence set forth in SEQ ID NO: 1.

In certain embodiments, the VEGFR-binding peptide comprises (or consists essentially of, or consists of) an amino acid sequence at least about 70%, at least about 75%, at least about 80%, at least about 85%, at least about 90% identical to the amino acid sequence set forth in SEQ ID NO: 2.

In certain embodiments, the nucleic acid-binding polypeptide comprises repeats of a histone, a histone variant, or a fragment thereof. In certain embodiments, the nucleic acid-binding polypeptide comprises repeats of a fragment of histone H2A. In certain embodiments, the nucleic acid-binding polypeptide comprises 1 to 10 repeats of a N-terminal fragment of histone H2A, and wherein the fragment has 15-50 amino acid residues in length. In one embodiment, the nucleic acid-binding polypeptide comprises 4 repeats of a N-terminal fragment of histone H2A, and wherein the fragment has about 37 amino acid residues in length. In one embodiment, the nucleic acid-binding polypeptide comprises a nuclear localization sequence.

In certain embodiments, the nucleic acid-binding polypeptide comprises (or consists essentially of, or consists of) an amino acid sequence at least about 70%, at least about 75%, at least about 80%, at least about 85%, at least about 90% identical to the amino acid sequence set forth in SEQ ID NO: 5.

In certain embodiments, the endosomolytic peptide is GALA, INF-7, KALA, RALA, or HSWYG.

In certain embodiments, the endosomolytic peptide comprises (or consists essentially of, or consists of) an amino acid sequence at least about 70%, at least about 75%, at least about 80%, at least about 85%, at least about 90% identical to the amino acid sequence set forth in SEQ ID NO: 6.

In certain embodiments, the VEGFR-binding peptide is located at the N-terminus of the fusion polypeptide. In certain embodiments, the endosomolytic peptide is located at the C-terminus of the fusion polypeptide.

Also encompassed by the present disclosure is a system for transfection of a nucleic acid into a cell, comprising: (a) the present fusion polypeptide; and (b) a nucleic acid.

In certain embodiments, the fusion polypeptide and the nucleic acid are suspended in an aqueous medium with a conductivity no greater than 10 mS/cm, or no greater than 2 mS/cm. In one embodiment, the fusion polypeptide and the nucleic acid are suspended in an aqueous medium with a conductivity of about 0.45 mS/cm.

In certain embodiments, the system further comprises dexamethasone, insulin (or its fragment), transferrin (or its fragment), a selenite, or combinations thereof. In one embodiment, the system further comprises about 0.1 μg/ml to about 0.6 μg/ml dexamethasone, about 5 μg/ml to about 20 μg/ml insulin (or its fragment), about 3 μg/ml to about 10 μg/ml transferrin (or its fragment), and about 0.003 μg/ml to about 0.010 μg/ml selenite.

In certain embodiments, the N:P ratio of the system ranges from about 1:1 to about 12:1. In one embodiment, the N:P ratio is about 5:1.

The present disclosure provides for a method of transfecting a nucleic acid into a cell, the method comprising contacting the cell with the present system. The contacting step of the method may be in vitro, ex vivo and/or in vivo.

The cell may be a eukaryotic cell, including mammalian cell. In one embodiment, the cell is a stem cell.

The present disclosure also provides for a kit comprising the present fusion polypeptide, or comprising the present system.

DETAILED DESCRIPTION

The present disclosure provides for non-viral compositions and methods for delivering nucleic acids into eukaryotic cells (e.g., stem cells) with high efficiency and low genotoxicity and/or cytotoxicity. The present fusion polypeptide may facilitate entry of nucleic acids into a cell, and release of nucleic acids from compartments or organelles (e.g., endosomes) within the transfected cells.

The present system and method achieve transfection efficiency of at least about 20%, at least about 30%, at least about 40%, at least about 45%, at least about 50%, at least about 55%, at least about 60%, at least about 65%, at least about 70%, at least about 75%, at least about 80%, at least about 85%, or at least about 90%. The transfection efficiency of the present system and method may be at least 1.2 fold, at least 1.5 fold, at least 2 fold, at least 2.5 fold, or at least 3 fold, of the transfection efficiency of the lipid-based or polymer-based transfection system of the prior art.

The present system and method has low cytotoxicity, killing less than about 40%, less than about 30%, less than about 25%, less than about 20%, less than about 15%, less than about 10%, or less than about 5%, of the cells which have been in contact with the present system or which have been transfected. In certain embodiments, the present system and method do not show any (or show minimal) genotoxicity and/or cytotoxicity, or negative impact on gene function or ability of the cell to differentiate.

The present disclosure provides for a fusion polypeptide, comprising (or consisting essentially of, or consisting of): (i) a cell surface receptor-binding peptide; (ii) a nucleic acid-binding polypeptide; and (iii) an endosomolytic peptide.

The cell surface receptor-binding peptide may be a vascular endothelial growth factor receptor (VEGFR)-binding peptide, an insulin-like growth factor receptor (IGFR)-binding peptide, a fibroblast growth factor receptor (FGFR)-binding peptide, an epidermal growth factor receptor (EGFR)-binding peptide, a platelet-derived growth factor receptor (PDGFR)-binding peptide, or an integrin-binding peptide.

The present disclosure provides for a fusion polypeptide, comprising: (i) a vascular endothelial growth factor receptor (VEGFR)-binding peptide; (ii) a nucleic acid-binding polypeptide; and (iii) an endosomolytic peptide.

In certain embodiments, the fusion polypeptide comprises (or consists essentially of, or consists of) an amino acid sequence at least about 50%, at least about 55%, at least about 60%, at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID NO: 10, SEQ ID NO: 11, SEQ ID NO: 22, SEQ ID NO: 23, SEQ ID NO: 24, SEQ ID NO: 25, or SEQ ID NO: 26 (Table 2).

In certain embodiments, the cell surface receptor-binding peptide is located at the N-terminus or C-terminus of the fusion polypeptide. In certain embodiments, the endosomolytic peptide is located at the C-terminus or N-terminus of the fusion polypeptide.

In certain embodiments, the VEGFR-binding peptide is located at the N-terminus or C-terminus of the fusion polypeptide. In certain embodiments, the endosomolytic peptide is located at the C-terminus or N-terminus of the fusion polypeptide.

The present disclosure also provides for a fusion polypeptide, comprising: (i) a cell-penetrating peptide; (ii) a nucleic acid-binding polypeptide; and (iii) an endosomolytic peptide.

In certain embodiments, the fusion polypeptide comprises (or consists essentially of, or consists of) an amino acid sequence at least about 60%, at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID NO: 8 or SEQ ID NO: 9 (Table 2).

In certain embodiments, the fusion polypeptide further comprises the Arg-Gly-Asp (RGD) peptide.

In certain embodiments, the cell-penetrating peptide is located at the N-terminus or C-terminus of the fusion polypeptide. In certain embodiments, the endosomolytic peptide is located at the C-terminus or N-terminus of the fusion polypeptide.

The fusion polypeptide can be designed to place the various functional moieties (a nucleic acid-binding polypeptide, an endosomolytic peptide, a cell surface receptor-binding peptide, and/or a cell-penetrating peptide) in any order. In the fusion polypeptide, these functional moieties may be covalently ligated continuously or non-continuously (e.g., they may be separated by linkers (e.g., linker amino acid residues)). The linker may have up to 30, up to 20, up to 18, up to 15, up to 12, up to 11, or up to 10, amino acid residues in length. In certain embodiments, the linker has about 1, 2, 3, 4, 5, 6, 7, 8, 9, 10-20, 8-10, 8-12, 8-15, 8-20, or 8-30 amino acid residues in length. In certain embodiments, the linker has about 7-10, 7-12, 7-15, 7-20, or 7-30 amino acid residues in length.

The present polypeptides or peptides may include variants, analogs, orthologs, homologs and derivatives of amino acids or peptides. The present polypeptides or peptides may contain one or more analogs of amino acids (including, for example, non-naturally occurring amino acids, amino acids which only occur naturally in an unrelated biological system, modified amino acids etc.), peptides with substituted linkages, as well as other modifications known in the art. The present polypeptides or peptides may comprise a peptidomimetic, such as a peptoid. The present polypeptides or peptides may contain one or more amino acid residues modified by, e.g., glycosylation, acylation (e.g., acetylation, formylation, myristoylation, palmitoylation, lipoylation), alkylation (e.g., methylation), isoprenylation or prenylation (e.g., farnesylation, geranylgeranylation), sulfation, amidation, hydroxylation, succinylation, etc.

In certain embodiments, the present fusion polypeptide includes a nuclear localization sequence (NLS) to direct the nucleic acid to the nucleus.

The present disclosure provides for a system (e.g., a nucleic acid delivery system, such as a gene delivery system) for delivering a nucleic acid into a cell, or a system for transfecting a cell. In certain embodiments, the system comprises: (a) the fusion polypeptide as described herein; and (b) a nucleic acid.

In certain embodiments, the present system further comprises one or more steroids (e.g., dexamethasone, prednisolone, methylprednisolone, etc.) insulin (or its fragment), transferrin (or its fragment), selenious acid, selenite, or combinations thereof. The steroids may be a corticosteroid (including glucocorticoids and mineralocorticoids) or a sex steroid.

In one embodiment, the present system comprises (a) the fusion polypeptide as described herein; (b) a nucleic acid, and (c) dexamethasone, insulin (or its fragment), transferrin (or its fragment), and/or selenious acid (and/or selenite).

The concentration of the steroid (e.g., dexamethasone, prednisolone, methylprednisolone, etc.) in the present system may range from about 0.01 µg/ml to about 1.00 µg/ml, from about 0.05 µg/ml to about 0.8 µg/ml, or from about 0.1 µg/ml to about 0.6 µg/ml. In one embodiment, the steroid (e.g., dexamethasone, prednisolone, methylprednisolone, etc.) is in the present system at a concentration of about 0.40 µg/ml.

The concentration of insulin (or its fragment) in the present system may range from about 1 µg/ml to about 40 µg/ml, from about 3 µg/ml to about 30 µg/ml, or from about 5 µg/ml to about 20 µg/ml. In one embodiment, insulin (or its fragment) is in the present system at a concentration of about 10 µg/ml. In certain embodiments, the insulin is human insulin. In certain embodiments, the insulin is from other non-human species as described herein.

The concentration of transferrin (or its fragment) in the present system may range from about 1 µg/ml to about 20 µg/ml, from about 2 µg/ml to about 15 µg/ml, or from about 3 µg/ml to about 10 µg/ml. In one embodiment, transferrin (or its fragment) is in the present system at a concentration of about 6 µg/ml. In another embodiment, transferrin (or its fragment) is present in the present system at a concentration of about 5.5 µg/ml. In certain embodiments, the transferrin is human transferrin. In certain embodiments, the transferrin is from other non-human species as described herein.

The concentration of selenious acid or selenite in the present system may range from about 0.001 µg/ml to about 0.015 µg/ml, from about 0.002 µg/ml to about 0.012 µg/ml, or from about 0.003 µg/ml to about 0.010 µg/ml. In one embodiment, selenious acid or selenite is in the present system at a concentration of about 0.007 µg/ml. In another embodiment, selenious acid or selenite is in the present system at a concentration of about 0.0067 µg/ml. In one embodiment, the selenite is sodium selenite.

In certain embodiments, a solution of the fusion polypeptide is desalted before mixing with the nucleic acids. In certain embodiments, the salt concentration of the solution of the fusion polypeptide is lowered before mixing with the nucleic acids.

The desalting step (or the step to lower the salt concentration) may be by using gel filtration chromatography (e.g., a desalting column), dialysis, ultrafiltration, and/or other methods known in the art.

In certain embodiments, before mixing with the nucleic acid, the fusion polypeptide is in an aqueous medium with a conductivity no greater than 10 mS/cm (milliSiemens per centimeter), no greater than 9 mS/cm, no greater than 8 mS/cm, no greater than 7 mS/cm, no greater than 6 mS/cm, no greater than 5 mS/cm, no greater than 4 mS/cm, no greater than 3 mS/cm, no greater than 2 mS/cm, no greater than 1 mS/cm, or no greater than 0.5 mS/cm. In one embodiment, the aqueous medium has a conductivity of about 0.45 mS/cm. In another embodiment, the aqueous medium has a conductivity of about 0.5 mS/cm.

The present disclosure also provides for a method of delivering a nucleic acid into a cell, or a method for transfecting a cell. The method may comprise contacting the cell with the present system. The contacting step may occur in vitro, ex vivo and/or in vivo (e.g., to treat a subject in need of treatment by the present system or method).

In certain embodiments, the present fusion polypeptide is used in an effective amount. An "effective amount" of the fusion polypeptide is an amount that will allow transfection to occur.

In certain embodiments, the present fusion polypeptides and nucleic acids form a complex in an aqueous solution. Such complexes may be formed spontaneously by mixing the fusion polypeptides with nucleic acids at the desired ratio.

The ratio of fusion polypeptides to nucleic acids may be balanced to maximize transfection efficiency and minimize genotoxicity and/or cytotoxicity.

In certain embodiments, the nucleic acids/fusion polypeptides complexes (e.g., nanoparticles) may have a N:P ratio ranging from about 1:1 to about 15:1, from about 1:1 to about 12:1, from about 1:1 to about 10:1, from about 1:1 to about 9:1, from about 1:1 to about 8:1, from about 1:1 to about 7:1, from about 1:1 to about 6:1, from about 1:1 to about 5:1, from about 1:1 to about 4:1, from about 4:1 to about 5:1, from about 4:1 to about 12:1, from about 5:1 to about 12:1, from about 4:1 to about 10:1, from about 5:1 to about 10:1, greater than 2:1, greater than 3:1, greater than 4:1, greater than 5:1, about 4:1, or about 5:1.

As used herein, the term "N:P ratio" refers to the molar ratio of positively charged nitrogen atoms in the nucleic acid-binding peptide to negatively charged phosphates in the nucleic acid (e.g., DNA, RNA, or any other nucleic acid as described herein). As the number of positive side-groups in a peptide side chain depends upon the sequence, different peptides will have differing numbers of positive charges per unit mass. In order to calculate this, the following equation may be used:

$$\text{N:P ratio} = M_{peptide}/M_{nucleic\ acid} \cdot C_{NP}$$

$M_{peptide}$ is the mass of the peptide (e.g., the nucleic acid-binding peptide). $M_{nucleic\ acid}$ is the mass of the nucleic acid (e.g., DNA, RNA, or any other nucleic acid as described herein). $C_{NP}$ is the N:P constant. The N:P constant is the ratio of the peptide's side chain positive charge density to the nucleic acid's backbone density, with the charge density being the charge of a substance divided by its molecular mass. In certain embodiments, for the peptide, lysine, arginine and histidine side groups are counted. In certain embodiments, for the nucleic acid, the average mass of one single base pair, and the charge of the phosphate group are used.

In certain embodiments, the fusion polypeptide and the nucleic acid are in an aqueous medium with a conductivity no greater than 10 mS/cm (milliSiemens per centimeter), no greater than 9 mS/cm, no greater than 8 mS/cm, no greater than 7 mS/cm, no greater than 6 mS/cm, no greater than 5 mS/cm, no greater than 4 mS/cm, no greater than 3 mS/cm, no greater than 2 mS/cm, no greater than 1 mS/cm, or no greater than 0.5 mS/cm. In one embodiment, the aqueous medium has a conductivity of about 0.45 mS/cm. In another embodiment, the aqueous medium has a conductivity of about 0.5 mS/cm.

In certain embodiments, the fusion polypeptides and nucleic acids form nanoparticles. In certain embodiments, the nanoparticles have sizes ranging from about 10 nm to about 600 nm, from about 10 nm to about 500 nm, from about 10 nm to about 400 nm, from about 50 nm to about 400 nm, from about 20 nm to about 150 nm, from about 10 nm to about 100 nm, from about 20 nm to about 100 nm, from about 10 nm to about 150 nm, from about 20 nm to about 150 nm, or from about 50 nm to about 150 nm.

In certain embodiments, the nucleic acids/fusion polypeptides nanoparticles are formed by the Flash Mixing method[19]. In brief, the fusion polypeptide solution is added to the nucleic acid (e.g., DNA, RNA, or other nucleic acid described herein) solution rapidly and flash mixed. The mixture is incubated, and then added/administered to the cells.

In certain embodiments, the nucleic acids/fusion polypeptides nanoparticles are formed by adding the nucleic acid solution to the fusion polypeptide solution dropwise while stirring. In certain embodiments, the nucleic acids/fusion polypeptides nanoparticles are formed by adding the fusion polypeptide solution to the nucleic acid solution dropwise while stirring. In certain embodiments, the nucleic acids/fusion polypeptides nanoparticles are formed by simultaneous mixing of the nucleic acid and fusion polypeptide solution using a microfluidic chamber.

The present fusion polypeptide may further include a fragment (e.g., tag) useful for polypeptide production and/or detection, including, but not limited to, poly-histidine (e.g., six histidine residues (SEQ ID NO: 249)) a maltose binding protein, GST, green fluorescent protein (GFP), hemagglutinin, or alkaline phosphatase, secretion signal peptides (e.g., preprotyrypsin signal sequence), c-myc, and/or FLAG.

The present fusion polypeptide can be derivatized or linked to another functional molecule. For example, present fusion polypeptide can be functionally linked (by chemical coupling, genetic fusion, noncovalent interaction, etc.) to one or more other molecular entities, such as an antibody or antibody fragment, a detectable agent, an immunosuppressant, a cytotoxic agent, a pharmaceutical agent, a protein or peptide that can mediate association with another molecule (such as a streptavidin core region or a polyhistidine tag), amino acid linkers, signal sequences, immunogenic carriers, or ligands useful in protein purification, such as glutathione-S-transferase, histidine tag, and staphylococcal protein A. Cytotoxic agents may include radioactive isotopes, chemotherapeutic agents, and toxins such as enzymatically active toxins of bacterial, fungal, plant, or animal origin, and fragments thereof.

One type of derivatized protein is produced by crosslinking two or more polypeptides (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Useful detectable agents with which a protein can be derivatized (or labeled) include fluorescent agents, various enzymes, prosthetic groups, luminescent materials, bioluminescent materials, and radioactive materials. Non-limiting, exemplary fluorescent detectable agents include fluorescein, fluorescein isothiocyanate, rhodamine, and, phycoerythrin. A polypeptide can also be derivatized with detectable enzymes, such as alkaline phosphatase, horseradish peroxidase, beta-galactosidase, acetylcholinesterase, glucose oxidase and the like. A polypeptide can also be derivatized with a prosthetic group (e.g., streptavidin/biotin and avidin/biotin).

In certain embodiments, the present system does not contain lipids. In certain embodiments, the present system comprises lipids.

The term "transfection" is used herein generally to mean the delivery and introduction of biologically functional nucleic acid (or polynucleotide) into a cell, e.g., a eukaryotic cell, in such a way that the nucleic acid retains its function within the cell. Transfection encompasses delivery and introduction of expressible nucleic acid into a cell such that the cell is rendered capable of expressing that nucleic acid. The term "transfecting" also means that a polynucleotide becomes associated with a selected cell. The polynucleotide can be on the membrane of the cell or inside the cytoplasm, nucleus, or other organelle of the cell. Other terms sometimes used interchangeably with transfecting include "delivering" or "transferring" to a cell.

The term "contacting" or "contact" as used herein in connection with contacting a cell includes subjecting the cell to an appropriate solution, buffer, or culture medium which comprises the present system. Where the cell is in vivo, "contacting" or "contact" includes administering the present system in a pharmaceutical composition to a subject via an appropriate administration route so that the nucleic acids contacts the cell in vivo.

As used herein, the term "genotoxicity" refers to the destructive effect of a nucleic acid delivery system (e.g., a gene delivery system) on a cell's genetic material (DNA and/or RNA) affecting its integrity. In certain embodiments, genotoxicity is reflected by micronuclei formation.

As used herein, the term "cytotoxicity" refers to the loss of cell viability after cell exposure to a nucleic acid delivery system (e.g., a gene delivery system), or a component or a solution of a nucleic acid delivery system.

Transfection activity or efficiency may be measured by detecting the presence of the transfected nucleic acid in a cell. In certain embodiments, a transfected nucleic acid is detected by measuring the biological function of the peptide/protein encoded by the nucleic acid in the cell. In certain embodiments, a transfected nucleic acid is assessed by measuring the level of transient or stable expression of a reporter gene contained in the transfected nucleic acid. The level of reporter gene expression may depend on, among other things, the amount of nucleic acid transfected. Generally, there are two classes of reporter gene detection systems used for reporter gene assays to determine gene transfer efficiency: quantitation and visualization. Quantitative methods use the appropriate substrates to measure a reporter gene product's activity. For example, the bioluminescent enzyme luciferase catalyzes the oxidative carboxylation of beet luciferin, emitting photons that may be measured using a luminometer. The amount of luciferase activity is usually proportional to the overall efficiency of transfection for a cell sample. In one common approach to measuring luciferase activity in a sample of transfected cells, cell extracts are prepared and the amount of luciferase activity in the extract is determined. Measurements of the activities of reporter gene products may be used in turn to determine the gene transfection efficiency. In certain embodiments, transfection activity or efficiency is assessed by determining the percent of cells in a sample that have been transfected. With these techniques, individual cells are visualized under a microscope and the number of cells exhibiting characteristics of the transfected reporter gene are counted. For example, cells transfected with the reporter gene beta-galactosidase undergo X-gal staining, during which the beta-galactosidase present in a cell will hydrolyze X-gal (5-bromo-4chloro-3-indoyl-beta-D-galactopyranoside) and yield a blue precipitate. Other detection and quantitative methods which may be used are well known in the art.

In certain embodiments, medium employed in transfection is similar to the medium used to culture cells for transfection. The medium may contain serum or may be serum-free medium.

It will also be apparent to those of ordinary skill in the art that methods, reagents, procedures and techniques other than those specifically detailed herein may be employed or readily adapted to produce the systems of the present disclosure and practice the present transfection methods. Such alternative methods, reagents, procedures and techniques are within the spirit and scope of this disclosure.

Cell Surface Receptor-Binding Peptides

In certain embodiments, the present fusion polypeptide comprises a peptide (e.g., a receptor-binding peptide) that binds to a cell surface receptor. Non-limiting examples of the cell surface receptors include growth factor receptors (e.g., vascular endothelial growth factor (VEGF) receptor, fibroblast growth factor receptor (FGFR), epidermal growth factor receptor (EGFR), etc.) or hormone receptors. Non-limiting examples of the cell surface receptors also include insulin-like growth factor receptor (IGFR), platelet-derived growth factor receptor (PDGFR), and integrin.

In certain embodiments, the present fusion polypeptide comprises a peptide (e.g., a cell surface antigen-binding peptide) that binds to a cell surface antigen.

The VEGF receptors (VEGFRs) may be VEGFR-1 (Flt-1), VEGFR-2 (KDR/Flk-1), or VEGFR-3 (Flt-4). A VEGFR may be membrane-bound (mbVEGFR) or soluble (sVEGFR). The VEGFR-binding peptide may be VEGFR-1-binding peptide, VEGFR-2-binding peptide, or VEGFR-3-binding peptide.

In certain embodiments, the VEGFR-binding peptide is an antagonist of VEGFR (e.g., VEGFR-1, VEGFR-2, and/or VEGFR-3). In certain embodiments, the VEGFR-binding peptide is an agonist of VEGFR (e.g., VEGFR-1, VEGFR-2, and/or VEGFR-3). In certain embodiments, the VEGFR-binding peptide is neither an antagonist nor an agonist of VEGFR (e.g., VEGFR-1, VEGFR-2, and/or VEGFR-3).

In certain embodiments, the VEGFR-binding peptide is an antibody (or a fragment thereof) that is specific for VEGFR (e.g., VEGFR-1, VEGFR-2, and/or VEGFR-3). For example, antibodies directed to VEGF, VEGFR1, VEGFR2, or the VEGF-VEGFR1 or VEGF-VEGFR2 complex are described in U.S. Patent Publication No. 20020032313, which is incorporated by reference in its entirety. Such antibodies can be monoclonal or polyclonal antibodies. Antibodies can also be variant antibodies, such as chimeric antibodies and humanized antibodies, and hybrid antibodies comprising immunoglobulin chains capable of binding VEGFR or the VEGF-VEGFR complex. The antibodies include all immunoglobulin classes (e.g., IgA, IgD, IgE, IgG, and IgM) and subclasses, as well as antibody fragments, so long as they are capable of binding VEGFR, or the VEGF-VEGFR complex. In certain embodiments, the antibody fragment has an antigen-binding portion. In certain embodiments, antibody fragments include, but are not limited to, Fab, F(ab')2, Fab', F(ab)', Fv, a disulfide linked Fv, single chain Fv (scFv), bivalent scFv (bi-scFv), trivalent scFv (tri-scFv), Fd, dAb fragment (e.g., Ward et al., Nature, 341:544-546 (1989)), an isolated CDR, diabodies, affibodies, triabodies, tetrabodies, linear antibodies, single-chain antibody molecules. Single chain antibodies produced by joining antibody fragments using recombinant methods, or a synthetic linker, are also encompassed by the present disclosure. Bird et al. Science, 1988, 242:423-426. Huston et al., Proc. Natl. Acad. Sci. USA, 1988, 85:5879-5883. Antibody fragments comprise only a portion of an intact antibody, generally including an antigen binding site of the intact antibody and thus retaining the ability to bind antigen. Examples of antibody fragments encompassed by the present invention include: the Fab fragment, having a light chain variable domain (V$_L$), light chain constant domain (C$_L$), heavy chain variable domain (V$_H$), and heavy chain constant domain (C$_H$); the Fab' fragment, which is a Fab fragment having one or more cysteine residues at the C-terminus of the C$_H$ domain; the Fd fragment having V$_H$ and C$_H$ domains; the Fd' fragment having V$_H$ and C$_H$ domains and one or more cysteine residues at the C-terminus of the C$_H$ domain; the Fv fragment having the V$_L$ and V$_H$ domains of a single arm of an antibody; the dAb fragment (Ward et al., "Binding Activities of a Repertoire of Single Immunoglobulin Variable Domains Secreted from *Escherichia coli*," Nature 341: 544-546 (1989), which is hereby incorporated by reference in its entirety) which consists of a V$_H$ domain; isolated CDR regions; F(ab')2 fragments, a bivalent fragment including two Fab' fragments linked by a disulphide bridge at the hinge region; single chain antibody molecules (Bird et al., "Single-Chain Antigen Binding Proteins," Science 242:423-426 (1988); and Huston et al., "Protein Engineering of Antibody Binding Sites: Recovery of Specific Activity in an Anti-Digoxin Single-Chain Fv Analogue Produced in *Escherichia coli*," PNAS 85:5879-5883 (1988), which are hereby incorporated by reference in their entirety); diabodies with two antigen binding sites, comprising a V$_H$ domain connected to a V$_L$ domain in the same polypeptide chain (see, e.g., WO 93/11161 to Whitlow et al. and Hollinger et al., "Diabodies: Small Bivalent and Bispecific Antibody Fragments," PNAS 90:6444-6448 (1993), which are hereby incorporated by reference in their entirety); affibodies which are triple helix high affinity peptides (see, e.g., Nygren P., Alternative binding proteins: Affibody binding proteins developed from a small three-helix bundle scaffold, FEBS Journal 275 (2008) 2668-2676, which is hereby incorporated by reference in its entirety), and linear antibodies comprising a pair of tandem Fd segments (VH-CH1-VH-CH1) which, together with complementary light chain polypeptides, form a pair of antigen binding regions (Zapata et al., "Engineering Linear F(ab')2 Fragments for Efficient Production in *Escherichia coli* and Enhanced Antiproliferative Activity," Protein Eng. 8(10): 1057-1062 (1995); and U.S. Pat. No. 5,641,870, which are hereby incorporated by reference in their entirety). See U.S. Pat. No. 8,580,755.

In certain embodiments, the VEGFR-binding peptide has up to 100, up to 90, up to 80, up to 70, up to 60, up to 50, up to 40, up to 30, up to 20, up to 18, up to 15, up to 12, up to 11, or up to 10, amino acid residues in length. In certain embodiments, the VEGFR-binding peptide has about 10-20, 8-10, 8-12, 8-15, 8-20, 8-30, 8-40, 8-50, or 8-60 amino acid residues in length. In certain embodiments, the VEGFR-binding peptide has about 7-10, 7-12, 7-15, 7-20, 7-30, 7-40, 7-50, or 7-60 amino acid residues in length.

In certain embodiments, the VEGFR-binding peptide comprises (or consists essentially of, or consists of) an amino acid sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID NO: 1 or SEQ ID NO: 2 (Table 1).

In certain embodiments, the VEGFR-binding peptide is an antagonist of VEGFR-1 as described in U.S. Pat. No. 7,250,395, incorporated herein by reference in its entirely.

In certain embodiments, the VEGFR-binding peptide is a fragment of VEGF (vascular endothelial growth factor) including, e.g., VEGF-A, placenta growth factor (PGF), VEGF-B, VEGF-C and VEGF-D. In certain embodiments, the VEGFR-binding peptide is a derivative, or a modified form of a fragment of VEGF. In certain embodiments, the VEGFR-binding peptide is a VEGF biomimetic peptide. In certain embodiments, the VEGFR-binding peptide is a fragment of a VEGF variant. Exemplary VEGF variant proteins are described in U.S. Patent Publication No. 20060286636 and 20070253952, which are hereby incorporated by reference in their entirety.

In certain embodiments, the VEGFR is human VEGFR. In certain embodiments, the VEGF is human VEGF.

The FGF receptors (FGFRs) may be FGFR1, FGFR2, FGFR3, FGFR4, FGFRL1, or FGFR6. The FGFR-binding peptide may be FGFR1-binding peptide, FGFR2-binding peptide, FGFR3-binding peptide, FGFR4-binding peptide, FGFRL1-binding peptide, or FGFR6-binding peptide.

The EGF receptors (EGFRs) may be EGFR (ErbB-1), HER2/neu (ErbB-2), Her 3 (ErbB-3), or Her 4 (ErbB-4). The EGFR-binding peptide may be ErbB-1-binding peptide, ErbB-2-binding peptide, ErbB-3-binding peptide, or ErbB-4-binding peptide.

The IGF receptors (IGFRs) may be IGFR-1. The IGFR-binding peptide may be IGFR-1-binding peptide.

In certain embodiments, the cell surface receptor-binding peptide is an antagonist of the cell surface receptor. In certain embodiments, the cell surface receptor-binding peptide is an agonist of the cell surface receptor. In certain embodiments, the cell surface receptor-binding peptide is neither an antagonist nor an agonist of the cell surface receptor.

In certain embodiments, the cell surface receptor-binding peptide is an antibody (or a fragment thereof) that is specific for the cell surface receptor. Such antibodies can be monoclonal or polyclonal antibodies. Antibodies can also be variant antibodies, such as chimeric antibodies and humanized antibodies, and hybrid antibodies comprising immunoglobulin chains capable of binding the cell surface receptor or the cell surface receptor-ligand complex. The antibodies include all immunoglobulin classes (e.g., IgA, IgD, IgE, IgG, and IgM) and subclasses, as well as antibody fragments, so long as they are capable of binding the cell surface receptor, or the cell surface receptor-ligand complex. In certain embodiments, the antibody fragment has an antigen-binding portion. In certain embodiments, antibody fragments include, but are not limited to, Fab, F(ab')2, Fab', F(ab)', Fv, a disulfide linked Fv, single chain Fv (scFv), bivalent scFv (bi-scFv), trivalent scFv (tri-scFv), Fd, dAb fragment (e.g., Ward et al., Nature, 341:544-546 (1989)), an isolated CDR, diabodies, triabodies, tetrabodies, linear antibodies, single-chain antibody molecules. Single chain antibodies produced by joining antibody fragments using recombinant methods, or a synthetic linker, are also encompassed by the present disclosure. Bird et al. Science, 1988, 242:423-426. Huston et al., Proc. Natl. Acad. Sci. USA, 1988, 85:5879-5883. Antibody fragments comprise only a portion of an intact antibody, generally including an antigen binding site of the intact antibody and thus retaining the ability to bind antigen. Examples of antibody fragments encompassed by the present invention include: the Fab fragment, having a light chain variable domain (V$_L$), light chain constant domain (C$_L$), heavy chain variable domain (V$_H$), and heavy chain constant domain (C$_H$); the Fab' fragment, which is a Fab fragment having one or more cysteine residues at the C-terminus of the C$_H$ domain; the Fd fragment having V$_H$ and C$_H$ domains; the Fd' fragment having V$_H$ and C$_H$ domains and one or more cysteine residues at the C-terminus of the C$_H$ domain; the Fv fragment having the $V_L$ and $V_H$ domains of a single arm of an antibody; the dAb fragment (Ward et al., "Binding Activities of a Repertoire of Single Immunoglobulin Variable Domains Secreted from *Escherichia coli*," Nature 341:544-546 (1989), which is hereby incorporated by reference in its entirety) which consists of a $V_H$ domain; isolated CDR regions; F(ab')2 fragments, a bivalent fragment including two Fab' fragments linked by a disulphide bridge at the hinge region; single chain antibody molecules (Bird et al., "Single-Chain Antigen Binding Proteins," Science 242:423-426 (1988); and Huston et al., "Protein Engineering of Antibody Binding Sites: Recovery of Specific Activity in an Anti-Digoxin Single-Chain Fv Analogue Produced in *Escherichia coli*," PNAS 85:5879-5883 (1988), which are hereby incorporated by reference in their entirety); diabodies with two antigen binding sites, comprising a $V_H$ domain connected to a $V_L$ domain in the same polypeptide chain (see, e.g., WO 93/11161 to Whitlow et al. and Hollinger et al., "Diabodies: Small Bivalent and Bispecific Antibody Fragments," PNAS 90:6444-6448 (1993), which are hereby incorporated by reference in their entirety); and linear antibodies comprising a pair of tandem Fd segments (VH-CH1-VH-CH1) which, together with complementary light chain polypeptides, form a pair of antigen binding regions (Zapata et al., "Engineering Linear F(ab')2 Fragments for Efficient Production in *Escherichia coli* and Enhanced Antiproliferative Activity," Protein Eng. 8(10): 1057-1062 (1995); and U.S. Pat. No. 5,641,870, which are hereby incorporated by reference in their entirety). See U.S. Pat. No. 8,580,755.

In certain embodiments, the cell surface receptor-binding peptide has up to 100, up to 90, up to 80, up to 70, up to 60, up to 50, up to 40, up to 30, up to 20, up to 18, up to 15, up to 12, up to 11, or up to 10, amino acid residues in length.

In certain embodiments, the cell surface receptor-binding peptide has about 10-20, 8-10, 8-12, 8-15, 8-20, 8-30, 8-40, 8-50, or 8-60 amino acid residues in length. In certain embodiments, the the cell surface receptor-binding peptide has about 7-10, 7-12, 7-15, 7-20, 7-30, 7-40, 7-50, or 7-60 amino acid residues in length.

In certain embodiments, the cell surface receptor-binding peptide comprises (or consists essentially of, or consists of) an amino acid sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID NO: 17, SEQ ID NO: 18, SEQ ID NO: 19, SEQ ID NO: 20, or SEQ ID NO: 21 (Table 1).

In certain embodiments, the FGFR is human FGFR. In certain embodiments, the FGF is human FGF.

In certain embodiments, the EGFR is human EGFR. In certain embodiments, the EGF is human EGF.

In certain embodiments, the IGFR is human IGFR. In certain embodiments, the IGF is human IGF.

In certain embodiments, the PDGFR is human PDGFR. In certain embodiments, the PDGF is human PDGF.

In certain embodiments, the integrin is human integrin.

Non-limiting examples of cell surface receptor-binding peptides also include the cell surface receptor-binding peptides in Tables 10-11. Liu et al., Tumor-targeting peptides from combinatorial libraries, Advanced Drug Delivery Reviews 110-111 (2017) 13-37, the content of which is incorporated herein by reference in its entirety.

TABLE 10

| Receptor | Sequence | SEQ ID NO |
|---|---|---|
| GPC3 | DHLASLWWGTEL (TJ12P1) | SEQ ID NO: 127 |
| PD-L1 | NYSKPTDRQYHF (APP1) | SEQ ID NO: 128 |
| β-Catenin | ACAQKLDGCSYISWSCG (BC1), | SEQ ID NO: 129 |
|  | ACSGWWPKCQGYIPGCG (BC2) | SEQ ID NO: 130 |
|  | ACAPGVYRCNQNFIWCG (BC3) | SEQ ID NO: 131 |
| PDGFRβ | IPLPPPSRPFFK | SEQ ID NO: 132 |
| PKCδ | LMNPNNHPRTPR (PKC-bp) | SEQ ID NO: 133 |
| PTPRJ | CHHNLTHAC (PTPRJ-pep19), | SEQ ID NO: 134 |
|  | CLHHYHGSC (PTPRJ-pep24) | SEQ ID NO: 135 |
|  | CHHALTHAC (PTPRJ-pep19.4) | SEQ ID NO: 136 |
| TfR 1 | SPRPRHTLRLSL (B18) | SEQ ID NO: 137 |
| Tie 2 | TMGFTAPRFPHY | SEQ ID NO: 138 |
| CD-21 | RMWPSSTVNLSAGRR (P1) | SEQ ID NO: 139 |
| VEGFRI (Flt-1) | NGYEIEWYSWVTHGMY (SP5.2) | SEQ ID NO: 140 |
| IL-10 RA | FRSFESCLAKSH | SEQ ID NO: 141 |
| EGFR | YHWYGYTPQNVI (GE11) | SEQ ID NO: 142 |
|  | QHYNIVNTQSRV | SEQ ID NO: 143 |
|  | QRHKPRE | SEQ ID NO: 144 |
| FGF8b | HSQAAVP (P12) | SEQ ID NO: 145 |
| aFGF | AGNWTPI (AP8) | SEQ ID NO: 146 |
| bFGF | PLLQATL (P7) | SEQ ID NO: 147 |

TABLE 10-continued

| Receptor | Sequence | SEQ ID NO |
|---|---|---|
| IL-6Rα | LSLITRL (S7) | SEQ ID NO: 148 |
| α5β1 | CRGDCL | SEQ ID NO: 149 |
| | GACRGDCLGA (synthetic peptide) | SEQ ID NO: 150 |
| | CRRETAWAC | SEQ ID NO: 151 |
| | GACRRETAWACGA (synthetic peptide) | SEQ ID NO: 152 |
| α6β1 | VSWFSRHRYSPFAVS (P3) | SEQ ID NO: 153 |
| αvβ3/αvβ5 | CDCRGDCFC (RGD-4C) | SEQ ID NO: 154 |
| αvβ6 | RTDLDSLRTYTL | SEQ ID NO: 155 |
| MMP-9 | CTTHWGFTLC (CTT) | SEQ ID NO: 156 |
| CD133 | APSPMIW, | SEQ ID NO: 157 |
| | LQNAPRS | SEQ ID NO: 267 |
| N-cadherin | SWTLYTPSGQSK | SEQ ID NO: 158 |
| E-cadherin | SWELYYPLRANL | SEQ ID NO: 159 |
| PSMA | WQPDTAHHWATL | SEQ ID NO: 160 |
| VEGFR-3 | CSDSWHYWC (P1) | SEQ ID NO: 161 |
| | WHWLPNLRHYAS (peptide III) | SEQ ID NO: 162 |
| EGFRvIII/EGFR | WHTEILKSYPHEb, | SEQ ID NO: 163 |
| | LPAFFVTNQTQD | SEQ ID NO: 266 |
| Carbonic anhydrase IX | YNTNHVPLSPKY (CALX-P1) | SEQ ID NO: 164 |
| EphA2 | YSAYPDSVPsMMS (YSA) | SEQ ID NO: 165 |
| EphB4 | TNYLFSPNGPIA (TNYL) | SEQ ID NO: 166 |
| PS | CLSYYPSYC | SEQ ID NO: 167 |
| HER2 | ACSLQDPNC#DWWGHYCG (H8) | SEQ ID NO: 168 |
| | ACGLQGYGCWGMYGKCG (H30) | SEQ ID NO: 169 |
| | CVGVLPSQDAIGIC (L-26-19) | SEQ ID NO: 170 |
| | CGPLPVDWYWC (L-26-24) | SEQ ID NO: 171 |
| | CEWKFDPGLGQARC (N-12-1) | SEQ ID NO: 172 |
| | CDYMTDGRAASKIC (N-12-2) | SEQ ID NO: 173 |
| | KCCYSL (p6.1) | SEQ ID NO: 174 |
| | MARSGL, | SEQ ID NO: 175 |
| | MARAKE, | SEQ ID NO: 268 |
| | MSRTMS | SEQ ID NO: 269 |
| | WTGWCLNPEESTWGFCTGSF (EC-1) | SEQ ID NO: 176 |
| | MCGVCLSAQRWT, | SEQ ID NO: 177 |
| | SGLWWLGVDILG | SEQ ID NO: 178 |
| TGA-72 | NPGTCKDKWIECLLNG (A3-10) | SEQ ID NO: 179 |
| | DPRHCQKRVLPCPAWL, | SEQ ID NO: 180 |
| | FRERCDKHPQKCTKFL | SEQ ID NO: 181 |
| | GGVSCMQTSPVCENNL (A2-6) | SEQ ID NO: 182 |
| Galectin-3 | ANTPCGPYTHDCPVKR (G3-C12), | SEQ ID NO: 183 |
| | PQNSKIPGPTFLDPH (G3-A9) | SEQ ID NO: 184 |
| T antigen | IVWHRWYAWSPASRI (P30-1) | SEQ ID NO: 185 |
| | HGRFILPWWYAFSPS (P-30) | SEQ ID NO: 186 |
| Fibrin-fibronectin complexes | CGLIIQKNEC (CTL1) | SEQ ID NO: 187 |
| | CNAGES SKNC (CTL2) | SEQ ID NO: 188 |
| FGFR | AESGDDYCVLVFTDSAWTKICDWSHFRN (C19) | SEQ ID NO: 189 |
| | MQLPLAT | SEQ ID NO: 190 |
| | CRALLRGAPFHLAEC | SEQ ID NO: 191 |
| E-selectin | IELLQAR | SEQ ID NO: 192 |

TABLE 10-continued

| Receptor | Sequence | SEQ ID NO |
|---|---|---|
| MMP2-processed collagen IV | TLTYTWS | SEQ ID NO: 193 |
| PSA | CVAYCIEHHCWTC (C-4) | SEQ ID NO: 194 |
| Notch1 NRR | ACERYQGCFSVGGYCG (NRR17) | SEQ ID NO: 195 |
| CD44 | THENWPA (CV-1) | SEQ ID NO: 196 |
|  | WHPWSYLWTQQA (RP-1) | SEQ ID NO: 197 |
| FGF3 | VLWLKNR (FP16) | SEQ ID NO: 198 |
| Extradomain-B fibronectin | CTVRTSADC (ZD2) | SEQ ID NO: 199 |
| APRIL | AAAPLAQPHMWA (sAPRIL-BP1) | SEQ ID NO: 200 |
| p16 | SHSLLSS | SEQ ID NO: 201 |
| pre-miR-21 | ALWPPNLHAWVP | SEQ ID NO: 202 |

GPC3: Glypican-3; T antigen: Thomson-Friedenreich glycoantigen; PS: Phosphatidyl serine; IL-10 RA: human interleukin-10 receptor alpha; TfR 1: human transferrin receptor 1; IL-6Rα: Interleukin 6 receptor chain α; Notch1 NRR, negative regulatory region in Notch 1; p16: Protein p (16INK4a).

TABLE 11

| Receptor | Sequence | SEQ ID NO |
|---|---|---|
| HER2 | LTVSPWY | SEQ ID NO: 203 |
| α-Enolase | SSMDIVLRAPLM (pHCT74) | SEQ ID NO: 204 |
| EGFR | FPMFNHWEQWPP | SEQ ID NO: 205 |
|  | SYPIPDT (P1) | SEQ ID NO: 206 |
|  | HTSDQTN (P2) | SEQ ID NO: 207 |
| MUC18 | CLFMRLAWC | SEQ ID NO: 208 |
| Nucleolin | DMPGTVLP | SEQ ID NO: 209 |
|  | DWRGDSMDS | SEQ ID NO: 210 |
|  | VPTDTDYS | SEQ ID NO: 211 |
|  | VEEGGYIAA | SEQ ID NO: 212 |
| GP130 | VTWTPQAWFQWV (VTW) | SEQ ID NO: 213 |
| Nestin | AQYLNPS | SEQ ID NO: 214 |
| Cadherins | CSSRTMHHC | SEQ ID NO: 215 |
| α4β1 | CPLDIDFYC | SEQ ID NO: 216 |
| α5β1 | CPIEDRPMC (RPMrel) | SEQ ID NO: 217 |
| αvβ6 | RGDLATLRQLAQEDGVVG-VR (H2009.1) | SEQ ID NO: 218 |
|  | SPRGDLAVLGHK (HBP) | SEQ ID NO: 219 |
|  | SPRGDLAVLGHKY (HBP-1) | SEQ ID NO: 220 |
| αvβ3 (RMS-I) | CQQSNRGDRKRC (RMS-I) | SEQ ID NO: 221 |
|  | CMGNKCRSAKRP (RMS-II) | SEQ ID NO: 222 |
| IL-13Rα2 | CGEMGWVRC | SEQ ID NO: 223 |
| VPAC1 | GFRFGALHEYNS (VP2) | SEQ ID NO: 224 |
| IGHC | CTLPHLKMC | SEQ ID NO: 225 |
| HSPG | ASGALSPSRLDT (OSP-1) | SEQ ID NO: 226 |
| Adenoviral receptor | SWDIAWPPLKVP | SEQ ID NO: 227 |
| GRP78 | CTVALPGGYVRVC (Pep42) | SEQ ID NO: 228 |
| GRP78 | ETAPLSTMLSPY (GMBP1) | SEQ ID NO: 229 |
| GRP78 | GIRLRG | SEQ ID NO: 230 |
| APP | CPGPEGAGC | SEQ ID NO: 231 |
| IL-11Rα | CGRRAGGSC | SEQ ID NO: 232 |
| PDGFRβ | CRGRRST (RGR) | SEQ ID NO: 233 |
| APN (CD13) | CNGRCVSGCAGRC (NGR) | SEQ ID NO: 234 |
| p32/gC1qR | CGNKRTRGC (LyP-1) | SEQ ID NO: 235 |
| TIP-1 | HVGGSSV | SEQ ID NO: 236 |
| α2bβ3 | RGDGSSV | SEQ ID NO: 237 |
| α3β1 | SWKLPPS | SEQ ID NO: 238 |
| αvβ3 αvβ5 | CRGDKRGPDC (iRGD) | SEQ ID NO: 239 |
| NRP-1 | GGKRPAR (P4) | SEQ ID NO: 240 |
|  | RIGRPLR (P7) | SEQ ID NO: 241 |
|  | CGFYWLRSC | SEQ ID NO: 242 |
|  | RPARPAR | SEQ ID NO: 243 |
| MMP2-processed collagen IV | TLTYTWS | SEQ ID NO: 244 |
| VAV3 | SSQPFWS | SEQ ID NO: 245 |
| CRKL | YRCTLNSPFFWEDMTHEC-HA | SEQ ID NO: 246 |
| Plectin-1 | KTLLPTP (PTP) | SEQ ID NO: 247 |

IGHC: immuno-globulin heavy chain; HSPG: heparin sulfate proteoglycans; IL-13Rα2: Interleukin 13 receptor α2; GRP78: glucose-regulated protein 78; APP: aminopeptidase P; NRP-1: neurophil-1; APN: aminopeptidase N.

Nucleic Acid-Binding Polypeptides

Nucleic acid-binding polypeptides may complex with a nucleic acid and compact the nucleic acid. Nucleic acid-binding polypeptides may bind to nucleic acids through electrostatic, hydrophobic, and/or steric interactions.

In certain embodiments, the nucleic acid-binding polypeptide is a cationic polypeptide.

In certain embodiments, the nucleic acid-binding polypeptide is wild-type, mutated, or modified.

In certain embodiments, the nucleic acid-binding polypeptide comprises one, or two or more repeats, of a nucleic acid-binding peptide (monomer). In the nucleic acid-binding polypeptide, these monomers may be repeated continuously or non-continuously. Thus, they may be separated by linkers (e.g., linker amino acid residues).

In some embodiments, the nucleic acid-binding peptide (monomer) has one or more lysine, arginine, and/or histidine residues. In some embodiments, the nucleic acid-binding peptide (monomer) further contains one or more cysteine residues.

In certain embodiments, the nucleic acid-binding polypeptide comprises one, or two or more repeats, of a nucleic acid-binding peptide (monomer), including, but not limited to, histones, nucleolin, protamines (e.g., PRM1 and PRM2), helix-loop-helix (HLH) proteins, zinc finger proteins, polylysines, transcription factors, polyhistidines, polyarginines, spermine, spermidine, DNA-binding peptides (such as the DNA-binding peptide mu from adenovirus), and fragments or variants thereof. In certain embodiments, the nucleic acid-binding peptide may comprise a N-terminal fragment of a C-terminal fragment of histones, nucleolin, protamines (e.g., PRM1 and PRM2), helix-loop-helix (HLH) proteins, zinc finger proteins, polylysines, transcription factors, polyhistidines, polyarginines, spermine, spermidine, DNA-binding peptides (such as the DNA-binding peptide mu from adenovirus). Nishikawa et al., Targeted delivery of plasmid DNA to hepatocytes in vivo: optimization of the pharmacokinetics of plasmid DNA/galactosylated poly(L-lysine) complexes by controlling their physicochemical properties. J Pharmacol Exp Ther 1998; 287 (1):408-15. Strydom et al., Studies on the transfer of DNA into cells through use of avidin-polylysine conjugates complexed to biotinylated transferrin and DNA. J Drug Target 1993; 1(2): 165-74.

In certain embodiments, the nucleic acid-binding polypeptide comprises one, or two or more repeats, of a histone (wildtype or mutated), a histone variant, or fragments thereof. Histones are basic proteins with high a content of lysine or arginine and function in the packaging of DNA. Histones are highly conserved and can be grouped into five major classes: H1/H5, H2A, H2B, H3, and H4.

As described herein, a histone may be a full-length histone, a histone variant, or a fragment of a histone.

A histone variant may be a histone modified by, for example, the deletion, addition and/or substitution of one or more amino acid residues (10 or fewer, 9 or fewer, 8 or fewer, 7 or fewer, 6 or fewer, 5 or fewer, 4 or fewer, 3 or fewer, 2 or fewer, amino acid residues or 1 amino acid residue). Alternatively, a histone may be modified by acetylation and/or methylation. In certain embodiments, the modifications do not substantially compromise the polycationic nature of the histone.

Suitable amino acid substitutions include, but are not necessarily limited to, amino acid substitutions known in the art as "conservative". A "conservative" substitution is one in which an amino acid is substituted for another amino acid that has similar properties, such that one skilled in the art of peptide chemistry would expect the biological activity, secondary structure and/or hydropathic nature of the polypeptide to be substantially unchanged Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine, histidine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; And (5) Phe, Tyr, Trp, His. A histone variant may also, or alternatively, contain non-conservative amino acid changes.

As used herein, the term variant also denotes any peptide, pseudopeptide (peptide incorporating non-biochemical elements) or protein differing from the wildtype protein or peptide, obtained by one or more genetic and/or chemical modifications. Genetic and/or chemical modification may be understood to mean any mutation, substitution, deletion, addition and/or modification of one or more residues of the protein or peptide considered. Chemical modification may refer to any modification of the peptide or protein generated by chemical reaction or by chemical grafting of biological or non-biological molecule(s) onto any number of residues of the protein.

The nucleic acid-binding polypeptide may be glycosylated, sulfonated and/or phosphorylated and/or grafted to complex sugars or to a lipophilic compound such as, for example, a polycarbon chain or a cholesterol derivative.

The sequence of a variant of a histone (histone variant) may be at least about 40%, at least about 45%, at least about 50%, at least about 55%, at least about 60%, at least about 65%, at least about 70%, at least about 75%, at least about 80%, at least about 83%, at least about 85%, at least about 88%, at least about 90%, at least about 93%, at least about 95%, at least about 96%, at least about 97%, at least about 98%, or at least about 99% identical to the sequence of a wildtype histone or a reference histone.

Also included within the meaning of the term "histone variant" are homologues of histones. A histone homologue is typically from a different species but sharing substantially the same biological function or activity as the corresponding histone from another species. For example, homologues of histones include but are not limited to, those from different species of mammals or microorganisms.

The histone fragment may be greater than 50 amino acids in length, between about 5 and about 50 amino acid residues in length, between about 5 and about 45 amino acid residues in length, between about 5 and about 40 amino acid residues in length, between about 5 and about 35 amino acid residues in length, between about 5 and about 30 amino acid residues in length, between about 5 and about 25 amino acid residues in length, between about 5 and about 20 amino acid residues in length, between about 5 and about 15 amino acid residues in length, or between about 5 and about 10 amino acid residues in length. In certain embodiments, a fragment of a polypeptide (e.g., histone) is 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more than 40 amino acid residues in length.

In certain embodiments, the nucleic acid-binding polypeptide comprises about 1, 2, 3, 4, 5, 6, 7, 8, 9, 10, about 1-10, about 2-10, about 3-10, about 4-10, about 5-10, about 2-100, about 2-50, about 2-20, or about 3-15, repeating units, of a nucleic acid-binding peptide (monomer).

In certain embodiments, the nucleic acid-binding polypeptide comprises two or more tandem repeats of a nucleic acid-binding peptide (monomer). The term "tandem repeat" means at least one identical nucleic acid-binding peptide (monomer) after another in tandem within the nucleic acid-binding polypeptide, also identified as (monomer)n, where n is about 1, 2, 3, 4, 5, 6, 7, 8, 9, 10, about 1-10, about 2-10, about 3-10, about 4-10, about 5-10, about 2-100, about 2-50, about 2-20, or about 3-15.

In certain embodiments, the nucleic acid-binding polypeptide has from about 10% to about 80%, from about 15% to about 70%, from about 20% to about 70%, from about 30% to about 70%, from about 30% to about 60%, or from about 30% to about 50%, lysine and/or arginine residues.

In certain embodiments, the nucleic acid-binding polypeptide comprises about 1, 2, 3, 4, 5, 6, 7, 8, 9, 10, about 1-10, about 2-10, about 3-10, about 4-10, about 5-10, about 2-100, about 2-50, about 2-20, or about 3-15 repeats of H2A, H2A variant, or a fragment of H2A.

In certain embodiments, the nucleic acid-binding polypeptide comprises 2 to 10 repeats of a N-terminal fragment of histone H2A, and where the fragment has 15-50 amino acid residues in length.

In certain embodiments, the nucleic acid-binding polypeptide comprises 4 repeats of a N-terminal fragment of histone H2A, and wherein the fragment has about 37 amino acid residues in length.

In certain embodiments, the nucleic acid-binding polypeptide comprises (or consists essentially of, or consists of) about 1, 2, 3, 4, 5, 6, 7, 8, 9, 10, about 1-10, about 2-10, about 3-10, about 4-10, about 5-10, about 2-100, about 2-50, about 2-20, or about 3-15 repeating units of an amino acid sequence at least about 60%, at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID NO: 5 (Table 1).

In certain embodiments, the nucleic acid-binding polypeptide comprises one or more repeats of one or more types of the nucleic acid-binding peptide (monomer) as described herein.

Endosomolytic Peptides

The endosomolytic peptide is capable of (or promotes) disrupting or lysing the endosome membrane facilitating/resulting in the release of the endosomal content into the cytoplasm of the cell. In certain embodiments, the endosomolytic peptide promotes the lysis of, and/or transport of the present fusion polypeptides and/or nucleic acids from, the cellular compartments such as the endosome, lysosome, endoplasmic reticulum (ER), golgi apparatus, microtubule, peroxisome, or other vesicular bodies within the cell, to the cytoplasm of the cell. In certain embodiments, the endosomolytic peptides include pH-sensitive peptides, natural or synthetic fusogenic lipids, and natural or synthetic cationic lipids.

In certain embodiments, the endosomolytic peptide is rich in histidine. The percentage of histidine in the endosomolytic peptide may range from about 10% to about 70%, or from about 20% to about 40%. In one embodiment, the endosomolytic peptide contains histidine, lysine, and/or arginine. In certain embodiments, the endosomolytic peptide includes one or more amino acids with imidazole side chains.

In certain embodiments, the endosomolytic peptide has up to 60, up to 50, up to 40, up to 30, up to 20, up to 18, up to 15, up to 12, up to 11, or up to 10, amino acid residues in length. In certain embodiments, the endosomolytic peptide has about 10-20, 8-10, 8-12, 8-15, 8-20, 8-30, 8-40, 8-50, or 8-60 amino acid residues in length. In certain embodiments, the endosomolytic peptide has about 7-10, 7-12, 7-15, 7-20, 7-30, 7-40, 7-50, or 7-60 amino acid residues in length.

Non-limiting examples of the endosomolytic peptides include GALA, INF-7, KALA, RALA, HSWYG and LAGA (Table 3). Lochmann et al., Drug delivery of oligonucleotides by peptides. Eur. J. Pharm. Biopharm. 58: 237-251.

In certain embodiments, the fusion polypeptide comprises an endosomolytic peptide comprising (or consisting essentially of, or consisting of) an amino acid sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID NO: 6 (Table 1).

In certain embodiments, the fusion polypeptide comprises an endosomolytic peptide comprising (or consisting essentially of, or consisting of) an amino acid sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in any of SEQ ID NOs: 12, 13, 14, 15 and 16.

Cell-Penetrating Peptides

Cell-penetrating peptides (CPPs) can cross the cellular membrane. In certain embodiments, cell-penetrating peptides gain entry into the cell via endocytosis and/or direct translocation through the cellular membrane. Endocytosis occurs by various mechanisms, including clathrin-dependent endocytosis and clathrin-independent endocytosis.

Cell-penetrating peptides can be cationic, amphipathic, hydrophobic, anionic, hydrophilic, or non-amphipathic. Cell-penetrating peptides can be linear or cyclical. Cell-penetrating peptides can be random coiled, alpha-helical, or contain beta-sheets.

In certain embodiments, the present fusion polypeptide comprises a non-cationic cell-penetrating peptide.

In certain embodiments, the cell-penetrating peptide has up to 60, up to 50, up to 40, up to 30, up to 20, up to 18, up to 15, up to 12, up to 11, or up to 10, amino acid residues in length. In certain embodiments, the cell-penetrating peptide has about 10-20, 8-10, 8-12, 8-15, 8-20, 8-30, 8-40, 8-50, or 8-60 amino acid residues in length. In certain embodiments, the cell-penetrating peptide has about 7-10, 7-12, 7-15, 7-20, 7-30, 7-40, 7-50, or 7-60 amino acid residues in length.

In certain embodiments, the fusion polypeptide comprises a cell-penetrating peptide comprising (or consisting essentially of, or consisting of) an amino acid sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID NOs: 3 or 4.

Non-limiting examples of cell-penetrating peptides also include the cell-penetrating peptides in Tables 4-9. Milletti, F., Cell-penetrating peptides: classes, origin, and current landscape, Drug Discovery Today, 2012, Volume 17, Numbers 15/16: 850-860, the content of which is incorporated herein by reference in its entirety.

TABLE 4

CPPs derived from heparan-, RNA- and DNA-binding proteins

Cationic
Heparan binding proteins

| Sequence | Name | SEQ ID |
|---|---|---|
| RKKRRRESRKKRRRES | DPV3 | SEQ ID NO: 27 |
| GRPRESGKKRKRKRLKP | DPV6 | SEQ ID NO: 28 |
| GKRKKKGKLGKKRDP | DPV7 | SEQ ID NO: 29 |
| GKRKKKGKLGKKRPRSR | DPV7b | SEQ ID NO: 30 |
| RKKRRRESRRARRSPRHL | DPV3/10 | SEQ ID NO: 31 |
| SRRARRSPRESGKKRKRKR | DPV10/6 | SEQ ID NO: 32 |
| VKRGLKLRHVRPRVTRMDV | DPV1047 | SEQ ID NO: 33 |
| SRRARRSPRHLGSG | DPV10 | SEQ ID NO: 34 |
| LRRERQSRLRRERQSR | DPV15 | SEQ ID NO: 35 |
| GAYDLRRRERQSRLRRRERQSR | DPV15b | SEQ ID NO: 36 |

RNA binding proteins

| Sequence | Name | SEQ ID |
|---|---|---|
| RKKRRQRRR | HIV-1 Tat | SEQ ID NO: 37 |
| RRRRNRTRRNRRRVR | FHV coat | SEQ ID NO: 38 |
| TRQARRNRRRRWRERQR | HIV-1 Rev | SEQ ID NO: 39 |
| TRRQRTRRARRNR | HTLV-II Rex | SEQ ID NO: 40 |
| KMTRAQRRAAARRNRWTAR | BMV Gag | SEQ ID NO: 41 |
| NAKTRRHERRRKLAIER | P22 N | SEQ ID NO: 42 |
| MDAQTRRRERRAEKQAQWKAAN | λN(1-22) | SEQ ID NO: 43 |
| TAKTRYKARRAELIAERR | φ21N(12-29) | SEQ ID NO: 44 |
| TRRNKRNRIQEQLNRK | Yeast PrP6 | SEQ ID NO: 45 |

DNA binding proteins

| Sequence | Name | SEQ ID |
|---|---|---|
| PRRRRSSSRPVRRRRRPRVSRRRRRRGGRRRR | Protamine 1 | SEQ ID NO: 46 |

Leucine zipper

| Sequence | Name | SEQ ID |
|---|---|---|
| RIKAERKRMRNRIAASKSRKRKLERIAR | Human cJun | SEQ ID NO: 47 |
| KRRIRRERNKMAAAKSRNRRRELTDT | Human cFos | SEQ ID NO: 48 |

Transcription factors

| Sequence | Name | SEQ ID |
|---|---|---|
| KRARNTEAARRSRARKLQRMKQ | Yeast GCN4 | SEQ ID NO: 49 |

Homeoproteins

| Sequence | Name | SEQ ID |
|---|---|---|
| RQIKIWFQNRRMKWKK | Penetratin | SEQ ID NO: 50 |
| RVIRVWFQNKRCKDKK | Islet-1 | SEQ ID NO: 51 |
| SKRTRQTYTRYQTLELEKEFHF | Fushi-tarazu | SEQ ID NO: 52 |
| NRYITRRRRIDIANALSLSERQIKIWFQNRRMKSKKDR | | |
| SQIKIWFQNKRAKIKK | Engrailed-2 | SEQ ID NO: 53 |
| RQVTIWFQNRRVKEKK | HoxA-13 | SEQ ID NO: 54 |
| KQINNWFINQRKRHWK | Knotted-1 | SEQ ID NO: 55 |
| RHIKIWFQNRRMKWKK | PDX-1 | SEQ ID NO: 56 |

TABLE 5

CPPs derived from signal peptides

Amphipathic (I): signal peptide + NLS

| Sequence | Name | SEQ ID |
|---|---|---|
| MGLGLHLLVLAAALQGAKKKRKV | Ig(v) | SEQ ID NO: 57 |
| MVKSKIGSWILVLFVAMWSDVGLCKKRPKP | BPrPp(1-30) | SEQ ID NO: 58 |

TABLE 5-continued

CPPs derived from signal peptides

| Sequence | Name | SEQ ID |
|---|---|---|
| MANLGYWLLALFVTMWTDVGLCKKRPKP | MPrPp(1-28) | SEQ ID NO: 59 |
| AAVLLPVLLAAPVQRKRQKLP | K-FGF + NLS | SEQ ID NO: 60 |

Hydrophobic: signal peptide alone

| Sequence | Name | SEQ ID |
|---|---|---|
| AAVLLPVLLAAP | K-FGF | SEQ ID NO: 61 |

TABLE 6

CPPs derived from antimicrobial peptides

Pro-rich

| Sequence | Name | SEQ ID |
|---|---|---|
| RRIRPRPPRLPRPRPRPLPFPRPG | Bac7 | SEQ ID NO: 62 |
| VDKGSYLPRPTPPRPIYNRN | Pyrrhocoricin | SEQ ID NO: 63 |

Amphipathic

| Sequence | Name | SEQ ID |
|---|---|---|
| KCFQWQRNMRKVRGPPVSCIKR | Human lactoferrin (19-40) | SEQ ID NO: 64 |
| TRSSRAGLQWPVGRVHRLLRK | Buforin 2 | SEQ ID NO: 65 |
| GIGAVLKVLTTGLPALISWIKRKRQQ | Melittin | SEQ ID NO: 66 |
| GIGKWLHSAKKFGKAFVGEIMNS | Magainin 2 | SEQ ID NO: 67 |
| LLGDFFRKSKEKIGKEFKRIVQRIK-DFLRNLVPRTESCRGGRLSYSRRRFSTSTGR | LL-37 | SEQ ID NO: 68 |
| | SynB1 | SEQ ID NO: 69 |
| YKQCHKKGGKKGSG | Crotamine | SEQ ID NO: 70 |
| ALWKTLLKKVLKAPKKKRKV | S4$_{13}$-PV$_{rev}$ | SEQ ID NO: 71 |
| HARIKPTFRRLKWKYKGKFW | L-2 | SEQ ID NO: 72 |

TABLE 7

CPPs derived from viral proteins

Unknown structure

| Sequence | Name | SEQ ID |
|---|---|---|
| TKRRITPKDVIDVRSVTTEINT | Inv3 | SEQ ID NO: 73 |

Amphipathic

| Sequence | Name | SEQ ID |
|---|---|---|
| RQGAARVTSWLGRQLRIAGKRLEGRSK | E$^{rns}$ | SEQ ID NO: 74 |
| NAATATRGRSAASRPTQRPRAPARSASRPRRPVQ | VP22 | SEQ ID NO: 75 |
| RHSRIGIIQQRRTRNG | HIV-1 VPR 77-92 | SEQ ID NO: 76 |
| KLIKGRTPIKFGKADCDRPPKHSQNGMGK | Ribotoxin2 L3 loop | SEQ ID NO: 77 |
| PLSSIFSRIGDP | PreS2-TLM | SEQ ID NO: 78 |

Amphipathic (b-sheet)

| Sequence | Name | SEQ ID |
|---|---|---|
| DPKGDPKGVTVTVTVTVTGKGDPKPD | VT5 | SEQ ID NO: 79 |

TABLE 8

CPPs derived from various natural proteins

Cationic

| Sequence | Name | SEQ ID |
|---|---|---|
| RRIPNRRPRR | HRSV | SEQ ID NO: 80 |
| RLRWR | AIP6 | SEQ ID NO: 81 |

TABLE 8-continued

CPPs derived from various natural proteins

Amphipathic (I)

| | | |
|---|---|---|
| MVRRFLVTLRIRRACGPPRVRV | ARF(1-22) | SEQ ID NO: 82 |
| MVTVLFRRLRIRRACGPPRVRV | M918 | SEQ ID NO: 83 |
| LLIILRRRIRKQAHAHSK | pVEC | SEQ ID NO: 84 |

Amphipathic (helical)

| | | |
|---|---|---|
| LSTAADMQGVVTDGMASG | Azurin p18 | SEQ ID NO: 85 |
| LSTAADMQGVVTDGMASGLDKDYLKPDD | Azurin p28 | SEQ ID NO: 86 |
| KFHTFPQTAIGVGAP | hCT18-32 | SEQ ID NO: 87 |

Hydrophobic

| | | |
|---|---|---|
| VPTLK | Bip | SEQ ID NO: 88 |
| (PMLKE, | | SEQ ID NO: 250 |
| VPALR, | | SEQ ID NO: 251 |
| VSALK, | | SEQ ID NO: 252 |
| IPALK) | | SEQ ID NO: 253 |
| PFVYLI | C105Y | SEQ ID NO: 89 |
| PIEVCMYREP | FGF12 | SEQ ID NO: 90 |

TABLE 9

Designed CPPs and CPPs derived from peptide libraries

Designed
Cationic

| | | |
|---|---|---|
| R8, | Polyarginine | SEQ ID NO: 254 |
| R9, | | SEQ ID NO: 255 |
| R10, | | SEQ ID NO: 256 |
| R12 | | SEQ ID NO: 257 |

Amphipathic (cationic I)

| | | |
|---|---|---|
| KETWWETWWTEWSQPKKKRKV | Pep-1 | SEQ ID NO: 91 |
| GLAFLGFLGAAGSTMGAWSQPKKKRKV | MPG | SEQ ID NO: 92 |

Amphipathic (cationic II)

| | | |
|---|---|---|
| GWTLNSAGYLLGKINLKALAALAKKIL | Transportan | SEQ ID NO: 93 |
| AGYLLGHINLHHLAHLAibHHIL | TH | SEQ ID NO: 94 |
| KLALKALKALKAALKLA | MAP | SEQ ID NO: 95 |
| RRWWRRWRR | W/R | SEQ ID NO: 96 |
| GLWRALWRLLRSLWRLLWRA | CADY | SEQ ID NO: 97 |
| LIRLWSHLIHIWFQNRRLKWKKK | EB-1 | SEQ ID NO: 98 |

Amphipathic (anionic II)

| | | |
|---|---|---|
| WEAALAEALAEALAEHLAEALAEALEALAA | GALA | SEQ ID NO: 99 |
| LKTLTETLKELTKTLTEL | MAP12 | SEQ ID NO: 100 |

Amphipathic (zero-charge II)

| | | |
|---|---|---|
| QLALQLALQALQAALQLA | MAP17 | SEQ ID NO: 101 |

Amphipathic (Proline-rich)

| | | |
|---|---|---|
| (PPR)3, | (PPR)n | SEQ ID NO: 258 |
| (PPR)4, | | SEQ ID NO: 259 |
| (PPR)5, | | SEQ ID NO: 260 |
| (PPR)6 | | SEQ ID NO: 261 |
| (PRR)3, | (PRR)n | SEQ ID NO: 262 |
| (PRR)4, | | SEQ ID NO: 263 |
| (PRR)5, | | SEQ ID NO: 264 |
| (PRR)6 | | SEQ ID NO: 265 |
| GPSQPTYPGDDAPVRDLIRFYRDLQRYLNVVTRHRY | aPP4R1 | SEQ ID NO: 102 |
| GPSQPTYPGDDAPVRDLIRFYRDLRRYLNVVTRHRY | aPP5R1 | SEQ ID NO: 103 |
| GPSQPTYPGDDAPVRDLRRFYRDLRRYLNVVTRHRY | aPP6R1 | SEQ ID NO: 104 |
| $G(P_LXX)_{NP_L}$ | PoliProline-based | |
| VRLPPPVRLPPPVRLPPP | SAP | SEQ ID NO: 105 |
| VELPPPVELPPPVELPPP | SAP(E) | SEQ ID NO: 106 |

Peptide libraries
Support-vector machine model

| | | |
|---|---|---|
| FKIYDKKVRTRVVKH | SVM1 | SEQ ID NO: 107 |
| RASKRDGSWVKKLHRILE | SVM2 | SEQ ID NO: 108 |
| KGTYKKKLMRIPLKGT | SVM3 | SEQ ID NO: 109 |
| LYKKGPAKKGRPPLRGWFH | SVM4 | SEQ ID NO: 110 |
| HSPIIPLGTRFVCHGVT | SVM5 | SEQ ID NO: 111 |
| YTAIAWVKAFIRKLRK | YTA2 | SEQ ID NO: 112 |
| IAWVKAFIRKLRKGPLG | YTA4 | SEQ ID NO: 113 |
| IAWVKAFIRKLRKGPLG | YTA4 | SEQ ID NO: 114 |

TABLE 9-continued

Designed CPPs and CPPs derived from peptide libraries

Plasmid display
Amphipathic

| | | |
|---|---|---|
| RLSGMNEVLSFRWL | SG3 | SEQ ID NO: 115 |

Phage display
Hydrophobic

| | | |
|---|---|---|
| SDLWEMMMVSLACQY | Pep-7 | SEQ ID NO: 116 |
| VTWTPQAWFQWV | | SEQ ID NO: 117 |
| GSPWGLQHHPPRT | 439a | SEQ ID NO: 118 |
| GPFHFYQFLFPPV | 435b | SEQ ID NO: 119 |
| TSPLNIHNGQKL | HN-1 | SEQ ID NO: 120 |

Other

| | | |
|---|---|---|
| CAYHRLRRC | | SEQ ID NO: 121 |

Phylomer library
Cationic

| | | |
|---|---|---|
| RCGRASRCRVRWMRRRRI | BEN_1079 | SEQ ID NO: 122 |

Other

| | | |
|---|---|---|
| PYSRPHVQLWYPNRESCRSLIRSLGP | BEN_0805 | SEQ ID NO: 123 |

Peptide arrays
Hydrophobic

| | | |
|---|---|---|
| PLILLRLLRGQF | Pept1 | SEQ ID NO: 124 |
| PLIYLRLLRGQF | Pept2 | SEQ ID NO: 125 |
| KLWMRWYSPTTRRYG | IVV-14 | SEQ ID NO: 126 |

Nucleic Acids

The present systems and methods deliver nucleic acids into eukaryotic cells, particularly higher eukaryotic cells.

The nucleic acid may be deoxyribonucleic acid (DNA), ribonucleic acid (RNA) or a DNA/RNA hybrid. The nucleic acid may be linear or circular (such as a plasmid). The nucleic acid may be single-stranded, double-stranded, branched or modified by the ligation of non-nucleic acid molecules. The nucleic acid may be natural, synthetic, or semi-synthetic. These nucleic acids may be of human, animal, plant, bacterial, viral, etc. origin.

Such nucleic acids include, but are not limited to, ESTs, PCR products, genomic DNA, cDNA, RNA, oligonucleotides and antisense constructs; such nucleic acids may be present within expression vectors. The nucleic acids include isolated naturally occurring as well as synthetic nucleic acids, and nucleic acids produced by recombinant technology. An RNA may be a single or double-stranded RNA and may be a small interference RNA (siRNA) or a ribozyme.

In certain embodiments, the nucleic acid is a plasmid DNA including a coding sequence for a transcription product or a protein of interest, together with flanking regulatory sequences effective to cause the expression of the protein in the transfected cells. Examples of flanking regulatory sequences are a promoter sequence sufficient to initiate transcription and a terminator sequence sufficient to terminate the gene product, by termination of transcription or translation. Suitable transcriptional or translational enhancers can be included in the exogenous gene construct to further assist the efficiency of the overall transfection process and expression of the protein in the transfected cells.

A marker or reporter gene encodes a gene product which can be easily assayed, as described herein. The presence of the product of the marker gene indicates that the cell is transfected and the amount of the product indicates how efficient the transfection process.

The nucleic acid may encompass both DNA and RNA from any source comprising natural and non-natural bases. The nucleic acid may contain one or more nucleotide analogs such as nucleotides comprising bases other than the five naturally occurring bases (adenine, guanine, thymine, cytosine and uracil). The monomers of the nucleic acid (e.g., nucleotides and/or nucleotide analogs) can be connected by phosphodiester linkages or modified linkages such as phosphotriester, phosphoramidate, siloxane, carbonate, carboxymethyl ester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages.

Nucleic acids may have a variety of biological functions. They may encode proteins, comprise regulatory regions, function as inhibitors of gene or RNA expression (e.g., antisense DNA or RNA, or RNAi), function as inhibitors of proteins, function to inhibit cell growth or kill cells, catalyze reactions, or function in a diagnostic or other analytical assay.

Particular useful nucleic acids in the present invention comprise genes. Exemplary genes encode transcription factors, cytoskeleton proteins, hormones, oncogenes, metabolic enzymes, ion channels, and reporter genes. A reporter gene may be any fluorescent protein, any enzyme for which immunocytochemical determination is possible (beta-galactosidase, beta-lactamase, etc.), or any protein or epitope tagged protein for which specific antibodies are available.

Gene products can be detected directly, as by the products of an enzyme or by antibody binding, or indirectly, as by linked enzyme assays or by effects which alter cell function. Altered cell function which can be detected include changes in the cell polarity, cell pH, cell morphology, or ability of a cell to bind certain compounds. Detection can be by fluorescence or luminescence.

The nucleic acid may comprise a gene so that the present systems and methods are used in gene therapy. The gene may be intended to overcome a gene deficiency or defect in the subject, i.e., where the subject fails to produce active, endogenous protein at all or within normal levels, and the gene introduced in the plasmid is intended to make up this deficiency. The gene may encode one or more polypeptides designed to treat any existing disease or condition. The gene may encode an antigenic peptide, capable of generating an immune response in humans or animals. In this particular embodiment, the present system and method help produce either vaccines or immunotherapeutic treatments applied to humans or to animals. The gene may encode an antisense RNA, an interfering RNA (such as a small interfering RNA (siRNA), a small hairpin RNA (shRNA)) and a microRNA (miRNA), a ribozyme, a mRNA, etc.

The nucleic acid may be contained within an expression vector. Thus, for example, a nucleic acid sequence may be included in any one of a variety of expression vectors for expressing a polypeptide, and more than one nucleic acid of interest may be included in one expression vector. Alternatively, parts of one gene or nucleic acid may be included in separate vectors. In some embodiments, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and derivatives of viral DNA).

Cells

The present system and method may deliver nucleic acids into any suitable types of cells. The cell may a eukaryotic cell. The cell may a mammalian cell, such as a human cell or a non-human mammalian cell (e.g., a non-human primate cell). These include a number of cell lines that can be obtained from American Tissue Culture Collection. In certain embodiments, the cell is infected with a pathogen, e.g. virus, bacteria, mycobacteria, fungi, unicellular organisms. In certain embodiments, the cell is a tumor cell.

In certain embodiments, the cell is present in a subject (e.g., a mammal). The mammal can be a human or a non-human primate. Non-human primates include, but are not limited to, chimpanzees, cynomologous monkeys, spider monkeys, and macaques, e.g., Rhesus. The mammal can be a transgenic non-human mammal.

In certain embodiments, the cell may be removed and maintained in tissue culture in a primary, secondary, immortalized or transformed state. In certain embodiments, the cells are cultured cells or cells freshly obtained from a source (e.g., a tissue, an organ, a subject, etc.). The mammalian cell can be primary or secondary which means that it has been maintained in culture for a relatively short time after being obtained from an animal tissue. These include primary liver cells, primary muscle cells, primary myoblasts, etc.

In certain embodiments, the present system and method deliver nucleic acids into a stem cell or a progenitor cell. Stem cells are undifferentiated cells that have the ability both to self-renew, and to generate differentiated progeny (see Morrison et al. (1997) Cell 88:287-298). They are found in multicellular organisms. In mammals, there are two broad types of stem cells: embryonic stem cells, and adult stem cells, which are found in various tissues.

The stem cells may be bone marrow-derived stem cells (BMSCs), adipose-derived stem cells (ADSCs), neural stem cells (NSCs), blood stem cells, or hematopoietic stem cells. Stem cells can also be from umbilical cord blood. Stem cells may be generated through somatic cell nuclear transfer or dedifferentiation.

The stem cells include, but are not limited to, a blood stem cell, an adipose stem cell, a bone marrow mesenchymal stem cell, a mesenchymal stem cell, a neural stem cell (NSC), a skin stem cell, an endothelial stem cell, a hepatic stem cell, a pancreatic stem cell, an intestinal epithelium stem cell, or a germ stem cell. In certain embodiments, mesenchymal stem cells are isolated from mesodermal organs, such as bone marrow, umbilical cord blood, and adipose tissue.

In certain embodiments, the stem cell is an induced pluripotent stem cell (iPS cell or iPSC). IPSC refers to a type of pluripotent stem cell artificially generated from a non-pluripotent cell, typically an adult somatic cell, or terminally differentiated cell, such as fibroblast, a hematopoietic cell, a myocyte, a neuron, an epidermal cell, or the like.

In certain embodiments, the present system and method deliver nucleic acids into a proliferating cell. In certain embodiments, the present system and method deliver nucleic acids into a T cell (including a primary T cell).

The cells can include autologous cells that are harvested from the subject being treated and/or biocompatible allogeneic or syngeneic cells, such as autologous, allogeneic, or syngeneic stem cells (e.g., mesenchymal stem cells), progenitor cells (e.g., connective tissue progenitor cells or multipotent adult progenitor cells) and/or other cells that are further differentiated.

In certain embodiments, cells are cultured prior to transfection. In certain embodiments, cells in the G2/M phase are transfected, where cells are synchronized by double-thymidine blockage, aphidocolin treatment or nocodazole treatment before transfection (Mortimer et al., Gene Ther 6: 401 411 (1999); Tseng et al, Biochim Biophys Acta 1445: 53 64)).

In certain embodiments of the present method, the cells are contacted with the present system for a period of time, ranging from about 1 hour to about 30 days, from about 3 hours to about 20 days, from about 5 hours to about 10 days, from about 5 hours to about 5 days, from about 10 hours to about 3 days, from about 12 hours to about 48 hours, from about 12 hours to about 36 hours, or about 24 hours.

Kits

The present invention also provides kits comprising the present fusion polypeptide or the present system.

In some aspects, the present disclosure provides kits that include a suitable container containing the present fusion polypeptide or the present system. In some embodiments, the present fusion polypeptide or the present system is in a formulation, e.g., pharmaceutical composition. In addition to the fusion polypeptide or the present system, the kit can include informational material. The informational material can be descriptive, instructional, marketing or other material that relates to the methods described herein and/or the use of the fusion polypeptide or the present system for the methods described herein. For example, the informational material describes methods for administering the formulation to a subject or methods for transfecting a cell. The kit can also include a delivery device.

In one embodiment, the informational material can include instructions to administer the formulation in a suitable manner, e.g., in a suitable dose, dosage form, or mode of administration (e.g., a dose, dosage form, or mode of administration described herein).

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In some embodiments, the individual components of the formulation can be provided in one container. Alternatively, it can be desirable to provide the components of the formulation separately in two or more containers. The different components can be combined, e.g., according to instructions provided with the kit. The components can be combined according to a method described herein, e.g., to prepare and administer a pharmaceutical composition.

In addition to the present fusion polypeptide or the present system, the kit can include other ingredients, such as a solvent or buffer, a stabilizer or a preservative, and/or a second agent for treating a condition or disorder.

The present fusion polypeptide or the present system can be provided in any form, e.g., liquid, dried or lyophilized form.

EXAMPLE 1

The vector that is used for stem cell transfection requires high efficiency because the methods used to rapidly produce unlimited quantities of undifferentiated stem cells have not yet been perfected. In addition to possessing high efficiencies, these vectors need to be non-genotoxic in stem cells because they could potentially transform normal stem cells into cancer initiating cells. Thus, it is essential to ensure that the engineered stem cells do not incur not only somatic, but also genetic aberrations during the transfection process. Unfortunately, for demonstration of safety in stem cells, non-viral vectors have been mainly evaluated for their impact on metabolic activity without considering impact on membrane integrity, differentiation ability, genetic integrity, and gene dysregulation.

The objective of this research was to develop an efficient vector that can be used for genetic modification of stem cells without any significant negative somatic or genetic impact.

To achieve the objective, two types of designer biomimetic vectors (DBVs) were engineered; targeted and non-targeted. The targeted vectors were composed of four repeating units of histone H2A to condense DNA (H4), a pH-dependent endosomolytic fusogenic peptide GALA (G), and either a Vascular Endothelial Growth Factor Receptor 1 (VEGFR-1) agonist targeting peptide (Vago) or antagonist peptide (Vanta). The rationale for targeting VEGFR-1 is that this receptor is overexpressed on the surface of stem cells and internalizes via receptor mediated endocytosis. The non-targeted vectors are composed of the same motifs which are mentioned above but instead of the VEGFR-1 targeting peptide, they have non-cationic cell penetrating peptides such as Pep1 (tryptophan-rich cluster with high affinity for membranes) and MPG (derived from the fusion sequence of the HIV glycoprotein 41). While many other cell-penetrating peptides are reported in literature (e.g., Tat), the rationale behind choosing these two peptides are: 1) non-cationic nature, 2) high efficiency in membrane fusion and cellular entry and 3) negligible cytotoxicity 13, 14, 15, 16, 17. The role of the cell penetrating peptides is to facilitate internalization of the vector through the stem cell membrane. To evaluate efficiency and safety of the vectors, Adipose-Derived MSCs (ADSCs) were selected for this study because in the clinical setting, they can be obtained from patients in large amounts using minimally painful procedures (unlike bone marrow-derived). The following widely used commercially available non-viral vectors were selected as controls: GeneIn™, Lipofectamine® LTX with Plus, Attractene, FuGENE® HD and jetPRIME®. A commercially available adenoviral vector (Ad-GFP) was used as a viral vector control. This research addressed two significant deficiencies that currently exist. The first is the low efficiency of non-viral vectors in MSC transfection, and the second is a lack of comprehensive toxicity data related to the cell proliferation rate, membrane integrity, micronuclei formation (genotoxicity), gene dysregulation and cell differentiation. The results of this study revealed that the VEGFR-1 targeted recombinant fusion vector could transfect mesenchymal stem cells with high efficiency (>50%) without showing any genotoxicity or negative impact on gene function or ability to differentiate. Overall, the results of this study show that use of receptors as ports for cellular entry is a safer approach for stem cell transfection in comparison to vectors that enter through cellular membrane. The developed vector could be used to transfect any mammalian cell line that overexpresses VEGFR-1 including all types of mesenchymal stem cells.

Materials and Methods

Genetic Engineering and Production of Recombinant Vectors

We used standard genetic engineering techniques similar to our previous reports in order to clone, express, and purify the DBVs 18, 19, 20. In brief, the genes encoding H4G, MPG-H4G, Pep1-H4G, Vago-H4G, and Vanta-H4G with 6×-histidine tag (SEQ ID NO: 249) at the c-terminus, were designed and then chemically synthesized by Integrated DNA Technologies (Coralville, Iowa, US). The corresponding amino acid sequences of the vectors are shown in Table 1. The genes were restriction digested by NdeI and XhoI enzymes and cloned into a pET21b bacterial expression vector (Novagen®, EMD Millipore, Mass., US). The fidelity of each gene sequence to the original design was verified by DNA sequencing.

To express the vectors, the expression plasmids were transformed into the LOBSTR BL21(DE3) *E. coli* expression strain (Kerafast Inc., MA, US). The protein expression protocol is optimized for the production of highly cationic vectors in *E. coli* as described previously by our group[21]. In brief, one colony was picked from the LB agar plate and inoculated overnight in a 5 ml Miller's LB media supplemented with 100 µg/mL carbenicillin (Sigma-Aldrich, MO, US). The next day, the starter culture was transferred into 500 mL terrific broth (TB) supplemented with 100 µg/mL carbenicillin. The culture was incubated at 37° C. under vigorous shaking until the $OD_{600}$ reached 0.4-0.6. To induce protein expression, isopropyl β-D-1-thiogalactopyranoside (IPTG, Teknova, Calif., US) was added to the culture at the final concentration of 1 mM. After 2.5-4 hours of induction, the *E. Coli* pellet was collected by centrifugation at 5000 g, weighed and stored in −80° C. freezer.

To purify the peptides, a method based on Ni-NTA immobilized metal affinity chromatography (QIAGEN, Md., US) was developed. A lysis buffer was formulated beforehand, containing 8 M urea, 2 M NaCl, 100 mM $NaH_2PO_4$, 10 mM Tris, 1% (v/v) Triton X-100, and 10 mM imidazole. The bacterial pellet was lysed by the lysis buffer (5 mL buffer per 1 gram pellet) for one hour at room temperature under vigorous stirring. Then, the supernatant was collected by centrifuging the slurry for one hour, at 20,000 rpm, 4° C. Meanwhile, the Ni-NTA resin was washed with 10 mL distilled/deionized water and preconditioned with 2 mL of lysis buffer. Afterwards, the supernatant was mixed with the preconditioned Ni-NTA resin and incubated on ice with gentle shaking. After one hour of incubation, the mixture was diluted with 3 times lysis buffer and passed through a 10-mL polypropylene filter column (Bio-Rad Inc., US) by vacuum driven filtration. The column was washed by 100 mL of lysis buffer followed by 50 mL wash buffer (5 M Urea, 1.5 M NaCl, 100 mM $NaH_2PO_4$, 10 mM Tris and 40 mM imidazole). Finally, the purified vector was eluted by 5 mL of elution buffer (3 M Urea, 0.5 M NaCl, 100 mM $NaH_2PO_4$, 10 mM Tris and 300 mM imidazole) and collected in 500 µL fractions. The concentration of the peptide within each fraction was measured by the Nanodrop 2000 spectrophotometer (Thermo Fisher Scientific, US). The purity of each peptide was determined by SDS-PAGE analysis.

Peptide Desalting and Preparation of Stock Solution

To desalt, a disposable PD-10 desalting column with Sephadex G-25 resin (GE Healthcare's Life Sciences, MA, US) was preconditioned with 15 mL of 10 mM L-Glu/L-Arg buffer (pH 5.8-6.0). Then, each purified peptide fraction was loaded onto the column and eluted with additional 5 mL of buffer driven by gravity. The concentration of each peptide was measured by Nanodrop 2000 spectrophotometer (Thermo Fisher Scientific, US) using the molecular weight and corresponding extinction coefficient as calculated by the ProtParam tool from the ExPASy Bioinformatics Resource Portal. The conductivity of the peptide solution was determined by Laser Doppler Velocimetry using Malvern Nano-ZS Zetasizer (Malvern Instruments, UK).

Nanoparticle Formation and Particle Size, Charge and Shape Analysis

The DNA/peptides nanoparticles were formed by the Flash Mixing method[19]. In brief, the required amount of each peptide to condense 1 µg of pEGFP plasmid DNA (pDNA) at various N:P ratios was calculated beforehand. For example, to prepare a N:P ratio of 1, the required amounts of H4G, MPG-H4G, Pep1-H4G, Vago-H4G and Vanta-H4G were 1.17 µg, 1.22 µg, 1.29 µg, 1.27 µg, and 1.35 µg, respectively. Then, pEGFP was diluted to a volume of 50 µL using distilled/deionized water. Concurrently, predetermined amount of each peptide was diluted to 50 µL volume using distilled/deionized water and placed in another microfuge tube. The peptide solution was added to the pDNA solution rapidly and flash mixed. After 5-10 minutes of incubation, the nanoparticle size was measured by Dynamic Light Scattering and surface charge by Laser Doppler Velocimetry using Malvern Nano-ZS Zetasizer (Malvern Instruments, UK). To make nanoparticles with the commercial transfection reagents including GeneIn™ (MTI-GlobalStem, MD, US), Lipofectamine® LTX with Plus (Thermo Fisher Scientific, MA, US), Attractene (QIAGEN, Md., US), FuGENE® HD (Promega Corporation, WI, US) and jetPRIME® (Polyplus-transfection, France), we followed the corresponding manufacturers' protocols. Once nanoparticles were formed, the surface charges were measured in 5 mM NaCl solution. The data are presented as mean±s.d. (n=3). Each mean is the average of 15 measurements while n represents the number of independent batches prepared for the measurements.

To study the morphology of the nanoparticles, transmission electron microscopy (TEM) was utilized[19]. First, nanoparticles were formed and then one drop of the mixture was loaded onto a carbon type B coated copper grid. As soon as the sample dried on the surface, the solution of 1% sodium phosphotungstate was added to stain the nanoparticles. The detailed images were recorded by 1200EX electron microscope (JEOL, US).

ADSC Characterization

The ADSCs (Lonza, N.J., US) were cultured in ADSC™ Growth Medium Bullet kit (Lonza, N.J., US) which contains the basal media and the necessary supplements for proliferation of human adipose derived mesenchymal stem cells. ADSCs were characterized for cell cycle and VEGFR-1 expression by flow cytometry. The cell cycle study was performed using propidium iodide (PI) DNA staining protocol. In brief, cells were seeded in 96-well plates at the density of 6000 cells per well. After 16, 20, 24, 26, 28 hours of incubation with ADSC™ Growth Medium Bulletkit at 37° C. and 5% CO2, cells were detached through trypsinization. Cells were then fixed by 70% cold ethanol. After 1 hour, cells were collected by centrifugation, re-suspended in PBS and treated with 0.5 mg/mL Rnase A. Finally, cells were stained by PI (10 µg/mL) for 1 hour. The cell cycle distribution was determined by flow cytometry (Beckman Coulter GALLIOS Cytometer, CA, US).

To determine the level of VEGFR-1 expression, ADSCs were detached by Accutase® Cell Detachment Solution (Innovative Cell Technologies, CA, US). Cells were fixed by 4% formaldehyde solution in PBS and then permeabilized by 0.1% Tween 20/PBS solution. Cells were washed and re-suspended in the staining buffer (0.3M glycine and 10% normal goat serum in PBS solution). 2 µL of Anti-VEGFR-1 rabbit monoclonal antibody conjugated with Alexa Fluor® 488 (abcam, MA, US) was added to each sample. Rabbit monoclonal IgG conjugated with Alexa Fluor® 488 (abcam, MA, US) was used as isotype control. Samples were incubated overnight at 4° C. and then washed extensively with PBS. The expression level of VEGFR-1 was determined by flow cytometry (Beckman Coulter GALLIOS Cytometer, CA, US). The unstained sample was also included as a negative control.

Evaluation of Cell Transfection Efficiency

The day before transfection, ADSCs were seeded in 96-well tissue culture plates at the density of 6000 cells per well and incubated for 24 hours. In a microfuge tube, nanoparticles were prepared at various N:P ratios as described above in a total volume of 50 µL and incubated for 5-10 minutes at room temperature. Each tube was further supplemented with 200 µL of ADSC basal media, 1 µM dexamethasone (Sigma-Aldrich, MO, US) and 1×ITS Liquid Media. A 100×ITS solution includes 1.0 mg/mL recombinant human insulin, 0.55 mg/mL human transferrin and 0.5 µg/mL sodium selenite (Sigma-Aldrich, MO, US), Next, the old media in each well was removed and replaced with the 250 µL nanoparticle mixture. Twenty four hours post transfection, the media in each well was replaced with 200 µL full growth media and the cells were allowed to grow for another twenty four hours. The green fluorescent protein (GFP) expression was visualized and qualitatively evaluated by a fluorescent microscope (Olympus, Fla., US). To quantify GFP expression and percent transfection, cells were trypsinized and analyzed by flow cytometry (Beckman Coulter CytoFLEX Cytometer, CA, US). The ratio of GFP positive cells to untransfected cells was calculated by Kaluza flow analysis software (Beckman Coulter, Calif., US).

To measure the transfection efficiency of commercially available transfection reagents including GeneIn™, Lipofectamine® LTX with Plus, Attractene, FuGENE® HD and jetPRIME®, cells were seeded in 96-well plates at the density of 6,000 cells/well. Twenty four hours later, cells were transfected following each manufacturer's cell transfection protocol.

To measure transduction efficiency of adenoviruses, cells were seeded as above. Adenovirus particles encoding GFP (Ad-GFP) were purchased from Baylor College of Medicine (TX, US), and the transduction process was performed according to the manufacturer's protocol. In brief, the multiplicity of infection (MOI) was calculated based on viral titer (plaque-forming units, PFU/mL). The Ad-GFP particles were mixed thoroughly with 300 μL of ADSC basal media. Next, the old media in each well was replaced by the transduction mixture. Four hours post transduction, the media in each well was replaced by the full growth media and the GFP expression was quantified after forty eight hours by flow cytometry as described above. The data are presented as mean±s.d. (n=3).

Evaluation of Vectors' Impact on Cell Proliferation Rate, Membrane Integrity and Morphology The impact of each vector on ADSC proliferation rates was evaluated by the WST-1 cell proliferation assay. Cells were seeded in the 96-well plates at the density of 6,000 cells per well. After twenty four hours of incubation, ADSCs were transfected with vectors as described above. Forty eight hours post-transfection, the old media was replaced with 100 μL of fresh media containing 10 μL WST-1 reagent (1:10 dilution). After one hour of incubation at 37° C./5% CO2, the absorbance of each well was measured by Infinite® M200 PRO NanoQuant microplate reader (Tecan, Switzerland) at 440 nm/600 nm. The absorbance of each treatment was normalized to the negative control (untreated cells) to measure the percentage of cell viability.

To evaluate the impact of each vector on ADSC membrane integrity, a lactate dehydrogenase (LDH) release assay (Roche, Ind., US) was performed using manufacturer's kit and protocol. In brief, cells were seeded and transfected as described above. Cells were incubated in ADSC basal media for 48 hours post transfection since the LDH reagent is not compatible with serum. Media in each well was removed and centrifuged at 250 g for 5 minutes to pellet the debris. The supernatants were collected into a 96-well plate with 100 μL per well. Next, 100 μL LDH reagent was added into each well and incubated for 30 minutes at room temperature. The absorbance at wavelengths of 490 nm and 600 nm was measured using Infinite® M200 PRO NanoQuant (Tecan, Switzerland) microplate reader. The media, without contacting any cells, served as the background control. The media from the untransfected cells was used as the negative control (spontaneous LDH release). The media from the cells incubated with the 2% Triton X-100 was served as the positive control (maximum LDH release). after subtracting the background control, the percentage of impact on membrane integrity was calculated as follows: % membrane integrity= (Positive-Treatment)/(Positive-Negative)×100. The data are presented as mean±s.d. (n=3).

The morphology of ADSCs before and after transfection was studied by using phase-contrast microscopy (Olympus, Fla., US).

Evaluation of Vectors' Impact on Micronuclei Formation (Genotoxicity)

Figure 1B:
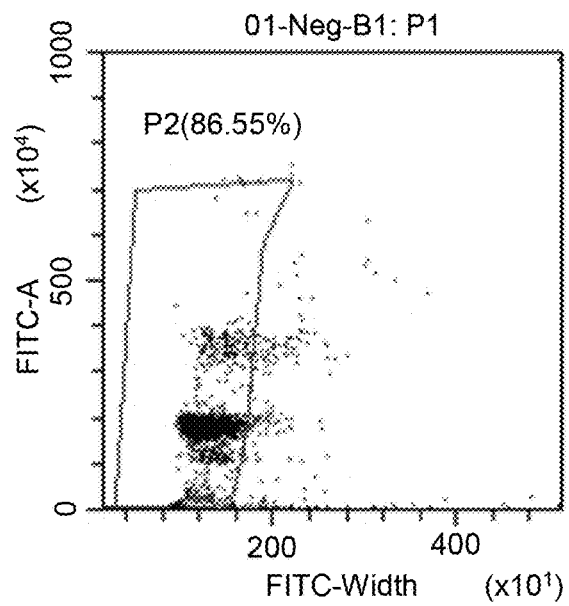
Figure 1C:
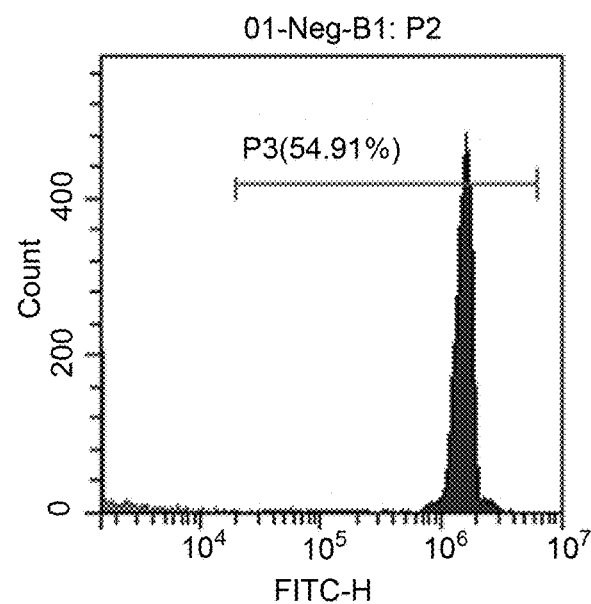
Figure 1D:
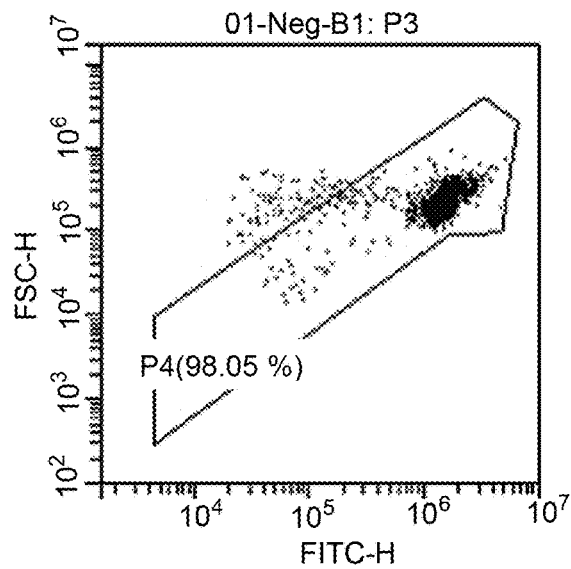
Figure 1E:
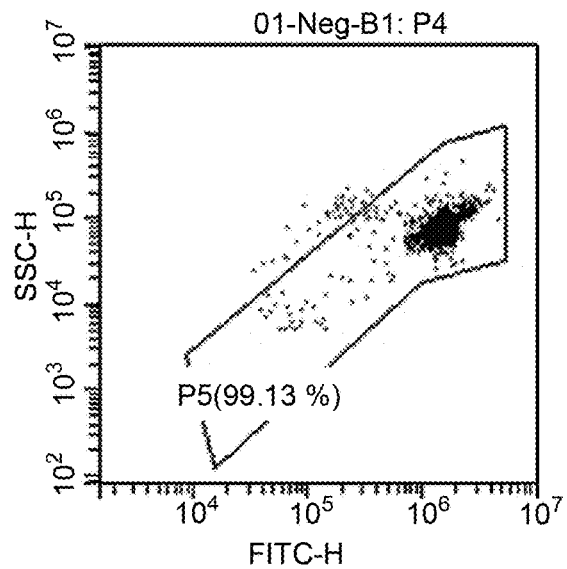
Figure 1F:
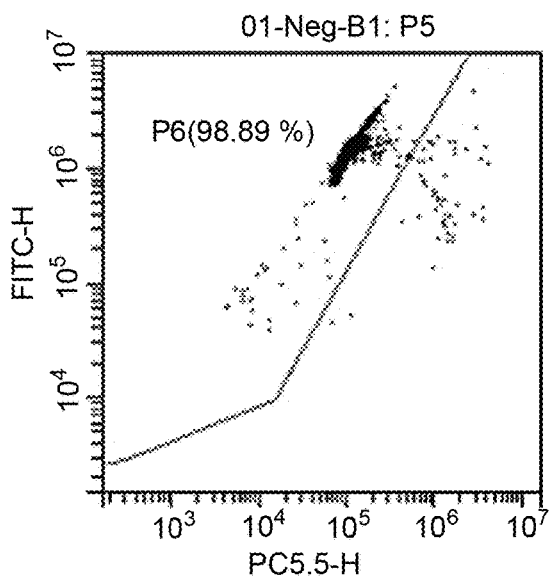
Figure 1G:
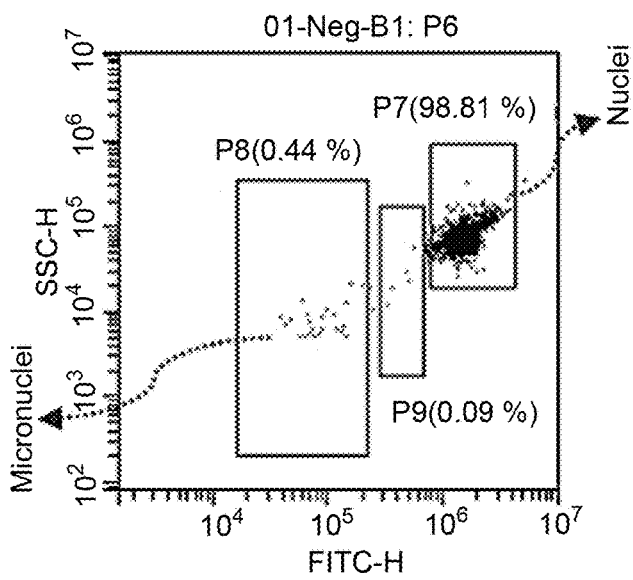

To quantify the percentage of micronuclei formation, cells were seeded and transfected as described above. Twenty four hours post-transfection (equivalent to 1-1.5 doubling time), cells were harvested and stained using an In Vitro MicroFlow® Kit (Litron Lab., NY). The staining was performed according to the manufacturer's protocol with several modifications. Briefly, cells were detached, transferred into a microfuge tube, and centrifuged for 6 min at 300 g. The supernatant was removed and the pellet was placed on ice for 20 min Next, ADSCs were resuspended in 50 μL of ethidium monoazide (EMA) solvent (Dye A). EMA is a DNA staining fluorescent dye that cannot pass through the cell membrane of live cells. As a result, it can only stain the late apoptotic or dead cells helping to distinguish them from live cells. After 30 min of incubation with EMA, cells were washed by the Kit's wash buffer, lysed by lysis buffer, and treated with Rnase enzyme. Cells were then exposed to SYTOX green fluorescent dye that stains all nuclei and micronuclei. The lysis and SYTOX green staining process were performed at 37° C. while samples were protected from light. After staining, samples were analyzed by CytoFlex Flow Cytometer (Beckman Coulter, Brea, Calif.) using an optimized acquisition protocol according to the guideline of In Vitro Microflow® Kit (FIGS. 1A-1G). The detailed information about the gating protocol can be found elsewhere[22]. Briefly, the process started by gating all events from side scatter vs. forward scatter plots (FIG. 1A) and continued with the second plot in which the doublet nuclei were discriminated and excluded by FITC width vs. FITC area plot (FIG. 1B). Next, the SYTOX Green positive events were selected (FIG. 1C) and the two different dot plots represented in FIGS. 1D and 1E illustrate nuclei and micronuclei populations with the correct size and pattern. This excludes other interfering events, such as smaller fluorescent particles, green fluorescent protein aggregates, and stained plasmids or nanoparticles. FIG. 1F shows exclusion of the EMA-positive events which originated from dead or late apoptotic cells. At this point, the number and percentage of micronuclei and nuclei shown in FIG. 1G can be quantified. In general, micronuclei are defined as events showing $\frac{1}{10}$ to $\frac{1}{100}$ of the mean intensity of SYTOX Green fluorescence found in nuclei of viable (i.e. EMA-negative) cells. The gating protocols were kept unchanged during the analysis and for each sample, at least 1000 EMA negative nuclei events were counted. Accordingly, % MN=Number of MN/Number of viable nuclei×100. The data are presented as mean±s.d. (n=4).

Determination of Vectors' Impact on Gene Regulation (Microarray Analysis)

The effects of vectors on the expression of 84 genes associated with cell growth regulation were analyzed by using the Human Genes RT[2] Profiler™ PCR Array (Qiagen, Md., US). The names of the tested genes are as follows: SERPINB5, MYCN, ABL1, AKT1, APC, ATM, BAX, BCL2, BCL2L1, BCR, BRCA1, BRCA2, CASP8, CCND1, CDH1, CDK4, CDKN1A, CDKN2A, CDKN2B, CDKN3, CTNNB1, E2F1, EGF, ELK1, ERBB2, ESR1, ETS1, FHIT, FOS, FOXD3, HGF, HIC1, HRAS, IGF2R, JAK2, JUN, JUNB, JUND, KIT, KITLG, KRAS, MCL1, MDM2, MEN1, MET, MGMT, MLH1, MOS, MYB, MYC, NF1, NF2, NFKB1, NFKBIA, NRAS, PIK3C2A, PIK3CA, PML, PRKCA, RAF1, RARA, RASSF1, RB1, REL, RET, ROS1, RUNX1, RUNX3, S100A4, SH3PXD2A, SMAD4, SRC, STAT3, STK11, TGFB1, TNF, TP53, TP73, TSC1, VHL, WT1, WWOX, XRCC1, ZHX2. ADSCs were seeded in the 96-well plates at the density of 6,000 cells per well and then transfected with selected DBVs. For adenovirus, ADSCs were seeded in a 6-well plate at the density of 100,000 cells per well and incubated for twenty four hours. Cells were transduced by Ad-GFP at MOI of 5,000 and 50,000 in a serum free media (ADSC basal media). Four hours post transduction, the media was removed and replaced with full growth media. Forty eight hours after, ADSCs were collected and the GFP positive cells were separated from the general population by the Moflo XDP Cell Sorter (Beckman Coulter, Calif., US). The GFP positive cells were reseeded in a 6-well plate at the density of 45,000 cells per well and allowed to fully recover from the process until they reached 80% confluency (4 to 8 days). The mRNAs of transfected and untransfected cells were extracted by Rneasy Mini Kit (Qiagen, Md., US). The genome DNA was eliminated by the Rnase-Free Dnase Set (Qiagen, Md., US) during the RNA isolation process. The concentration and purity of mRNA were evaluated by measuring the absorbance at wavelength 260 nm and 280 nm. Concurrently, an agarose gel (1%) electrophoresis was performed to examine the mRNA integrity. Then, 0.5 µg of mRNA was reverse transcribed into complementary DNA (cDNA) by $RT^2$ First Strand Kit (Qiagen, Md., US). The cDNA of each sample with $RT^2$ SYBR Green ROX PCR Master mix (Qiagen, Md., US) was loaded onto the PCR array. The real-time PCR reactions were performed using StepOnePlus™ Real-Time PCR System (Thermo Fisher Scientific, MA, US). The program settings on temperature cycling were followed as instructed by the manufacturer. The raw data and gene profile expression was analyzed by "Double Delta Ct Method" using the manufacturer's online software tool. Here, five housekeeping genes (ACTB, B2M, GAPDH, HPRT1 and RPLP0) were used as controls. All experiments were performed in triplicates while a two-fold change in RNA levels served as the cut-off point (*, $p<0.05$).

Evaluation of Vectors' Impact on ADSC Differentiation

To examine whether the transfection process had a negative impact on ADSC differentiation, the cells were induced to differentiate into adipocytes. ADSCs were transfected with the developed vectors and after 48 h post-transfection, were harvested and sorted by flow cytometry according to their respective GFP expression. The sorted GFP-positive cells were then reseeded in 96-well plates at the density of 10,000 cells per well and incubated at 37° C. with ADSC full media. The media was changed every other day until cells reached maximum confluency. At this point, the ADSC full growth media was removed and replaced with adipogenesis differentiation media cocktail (Lonza Inc., NJ) containing 1 µM dexamethasone, 0.5 mM isobutyl-methylxanthine (IBMX), 1 µg/ml insulin, and 100 µM indomethacin. The differentiation media was gently replaced every 3 days for 12 days. Next, ADSCs were washed by PBS and stained with AdipoRed™ fluorescent staining reagent (Lonza Inc., NJ). The production of intracellular oil vesicles was visualized by fluorescent microscopy (Olympus Co., USA) and the percentage of differentiated ADSCs was quantified by flow cytometry. Untransfected ADSCs were subjected to the same differentiation protocol and used as the positive control. The data are presented as mean±s.d. (n=3).

Results and Discussion

Figure 2A:
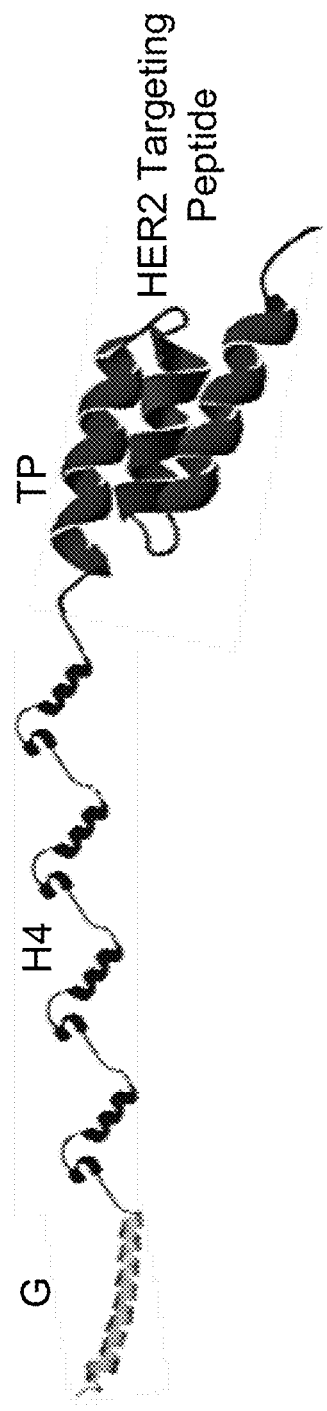
FIGS. 2A-2F show fusion polypeptide schematics and characterization of nanoparticles in terms of size, charge and shape.
Figure 2B:
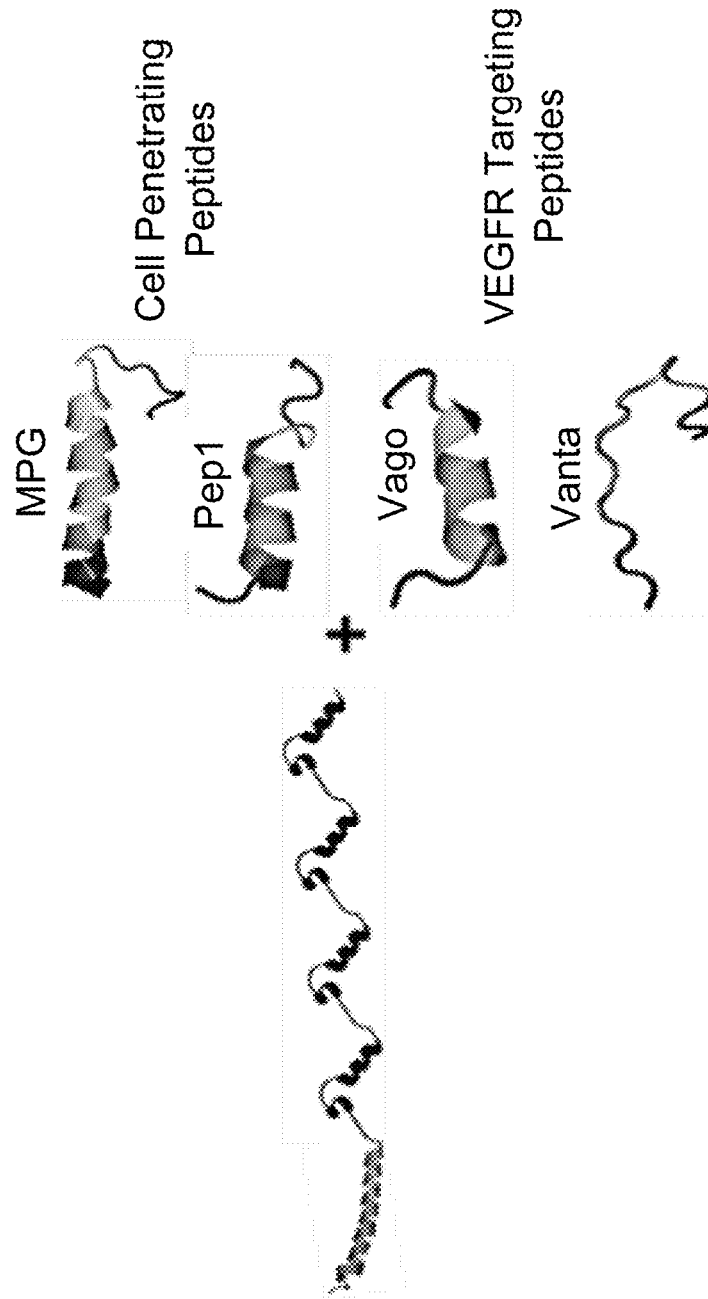

The concept of engineering recombinant fusion vectors for gene delivery dates back to the late 1990s[23]. However, due to significant technical difficulties related to recombinant production of highly cationic vectors and formulation of stable and efficient nanoparticles, recombinant fusion vectors remained ineffective for more than a decade (reviewed in reference[24]). Since 2006, we have worked to overcome these challenges and through the use of several innovative approaches, have successfully created highly efficient targeted fusion vectors for various gene delivery applications including the targeting of different cancer cell types or compartments within the cell[25, 26, 27, 28, 29]. We have previously reported the structure of a DBV composed of four repeating units of histone H2A (H4) for efficient condensation of DNA into nanosize particles and a pH-dependent fusogenic peptide (GALA) for disruption of endosome membranes facilitating the escape of cargo into the cytoplasm. Due to the presence of an inherent nuclear localization signal in the structure of histone H2A[30], the vector also uses microtubules to actively transport the nanoparticles towards the cell nuclear membrane[20]. To make the above mentioned vector (i.e., H4G) suitable for targeted gene transfer to HER2 positive mammalian cells (e.g., SKOV-3), a HER2 targeting affibody was fused with the vector sequence (FIG. 2A)[29]. We have demonstrated that this vector can target and transfect SKOV-3 cancer cells above a 95% efficiency[31]. To make this vector suitable for transfection of stem cells, a primary cell line without HER2 expression, we replaced the HER2 targeting peptide in the vector structure with the VEGFR1 targeting peptides and cell penetrating peptides (FIG. 2B). The sequences of the VEGFR targeting peptides (agonist and antagonist) are previously reported and also shown in Table 1[32, 33]. To achieve the objective, we first genetically engineered the DBVs as described below.

Genetic Engineering and Production of Fusion Vectors

Figure 7:
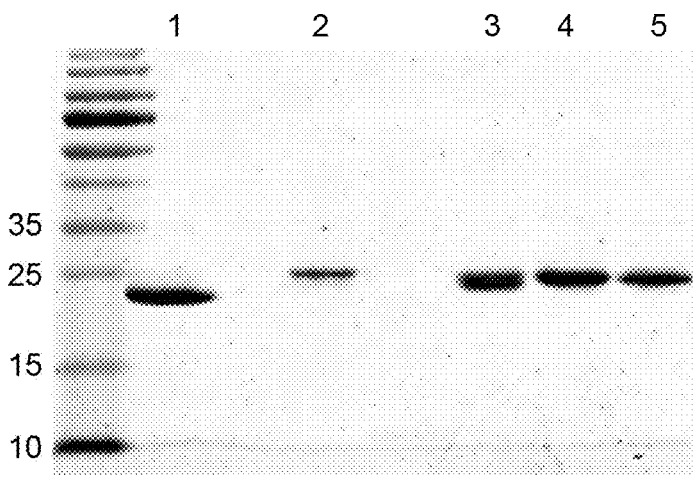
FIG. 7: SDS-PAGE analysis of the purified designer biomimetic vectors (DBVs). Lanes 1 to 5: H4G (19.75 kDa), Pep1-H4G (22.58 kDa), MPG-H4G (22.54 kDa), Vago-H4G (22.33 kDa), Vanta-H4G (22.45 kDa), respectively.

Considering that the above mentioned DBVs are highly cationic, their production in *E. coli* expression systems is marred by low expression yield which complicates the possibility of obtaining pure products. For example, SlyD and ArnA endogenous *E. coli* proteins are considered the major culprits that co-purify with the low-expressing DBVs during metal affinity chromatography[34]. The inability to produce highly pure vectors and in sufficient quantities are among the major obstacles that significantly hampered the progress of this field of research. To overcome this obstacle, we developed and previously reported an optimized protocol for the recombinant production of cationic fusion vectors[21]. Using this protocol, all constructs were expressed in an *E. coli* expression system, purified by Ni-NTA affinity columns and analyzed for purity by SDS-PAGE. The results of this study showed that by using *E. coli* BL21(DE3) LOBSTR strain in combination with the developed stringent expression and Ni-NTA purification methods, highly pure products in one purification step (>95% purity) could be obtained (FIG. 7). In the next step, we examined the ability of the vectors to condense pDNA into nanosize particles.

Nanoparticle Formation and Particle Size, Charge and Shape Analysis

Figure 2C:
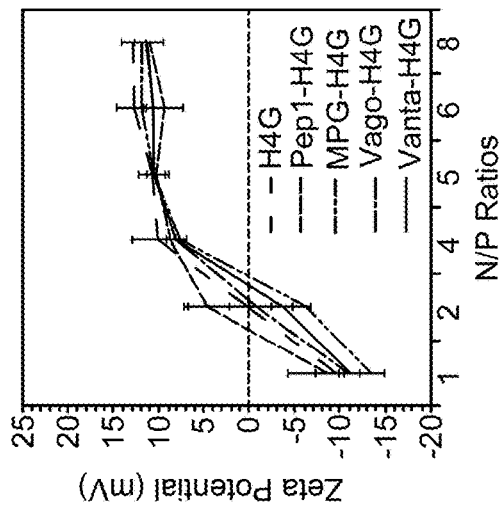
Figure 2D:
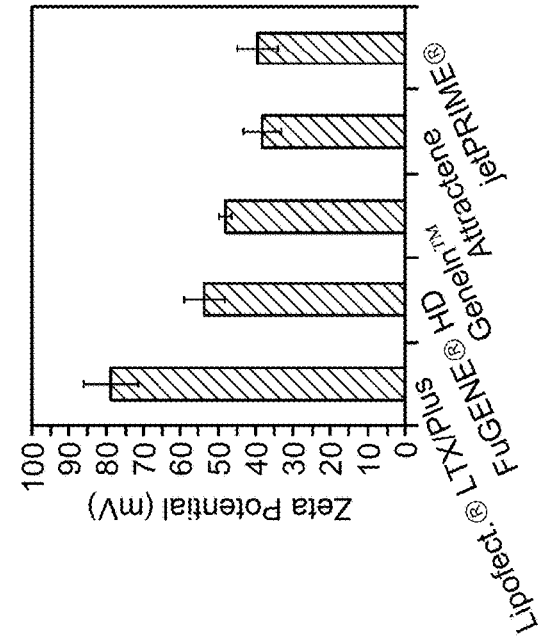
Figure 2E:
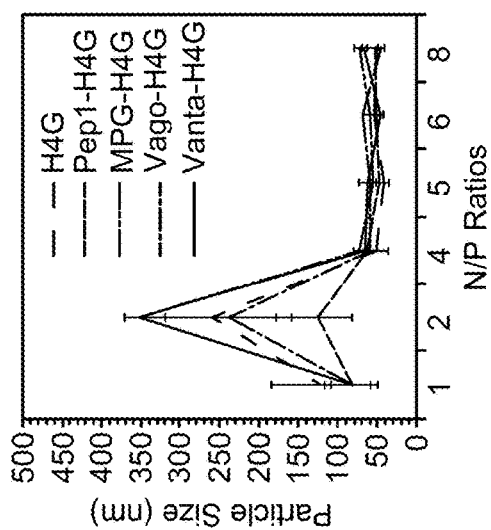

We performed a peptide desalting step before forming nanoparticles. The desalting step is important as it helps remove the excess ions from the system. This procedure stabilizes the nanoparticles' diameters by minimizing the possibility of inter-particle salt bridge formation and ensuing aggregation. In addition, presence of excess ions in the media interferes with the electrostatic interactions between cationic residues in the vector sequence and anionic residues in the pDNA resulting in formation of pseudo-condensed DNA. Therefore, we performed a desalting step to significantly reduce the ionic strength of DBV solution which brought down the solution conductivity from 33.7±0.6 mS/cm to 0.45±0.01 mS/cm without compromising solubility. We have previously shown that this level of conductivity is equivalent to that of a 5 mM NaCl solution[35]. The low conductivity value allows for efficient condensation of pDNA by DBVs and production of stable nanoparticles. The purified/desalted DBVs were then complexed with pDNA (i.e., pEGFP) at various N:P ratios and characterized in terms of size, surface charge and morphology. The results of this study showed that all DBVs were able to condense pEGFP into floccus, spherical particles with sizes of less than 100 nm and surface charges below +15 mV (FIG. 2C-E). The analysis of data showed that all nanoparticles beyond the N:P 4 ratio were statistically the same in terms of size and charge (p>0.05). Maintaining the nanoparticle surface charge below +20 mV is critically important as it has been shown that the potential for genetic aberrations (genotoxicity) increases when the surface charge goes beyond +20 mV[36]. This goal could be reached due to the unique structure of the histone H2A in the DBV sequence. Histone H2A is a basic peptide with the amino acid sequence of SGRGKQGGKARA-KAKTRSSRAGLQFPVGRVHRLLRKG (SEQ ID NO: 248). Even though only 33% of amino acid residues in the Histone H2A sequence are cationic, it can efficiently condense pDNA into nanosize particles. This efficiency in DNA condensation is attributed to the alpha-helix secondary structure at the H2A N-terminal domain[30]. As a result, less amount of vector is needed to efficiently condense pDNA into compact nanoparticles.

Figure 2F:
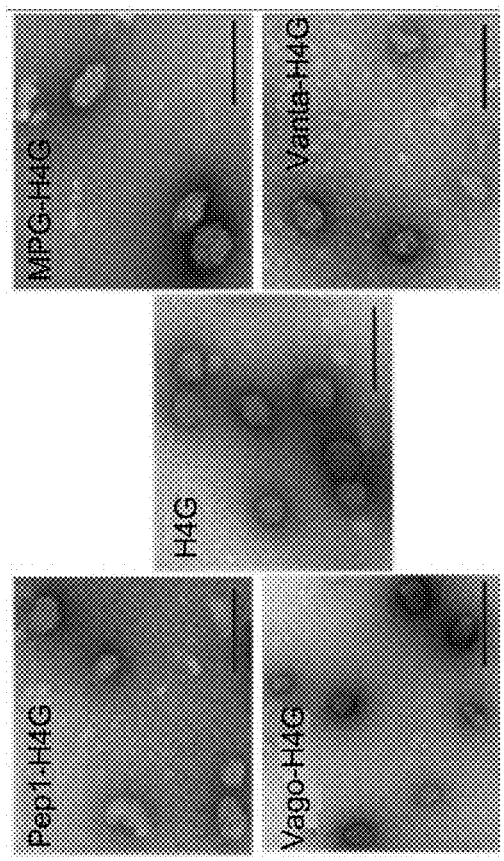

The commercial vectors used in this study were able to generate nanoparticles with surface charges ranging from +30 mV to +80 mV (FIG. 2F). While this high surface charge guarantees production of stable nanoparticles even in the presence of serum, there remains significant potential for toxicity in primary mammalian cell lines such as stem cells.

Characterization of ADSCs in Terms of Cell Cycle and VEGFR-1 Expression

Figure 3A:
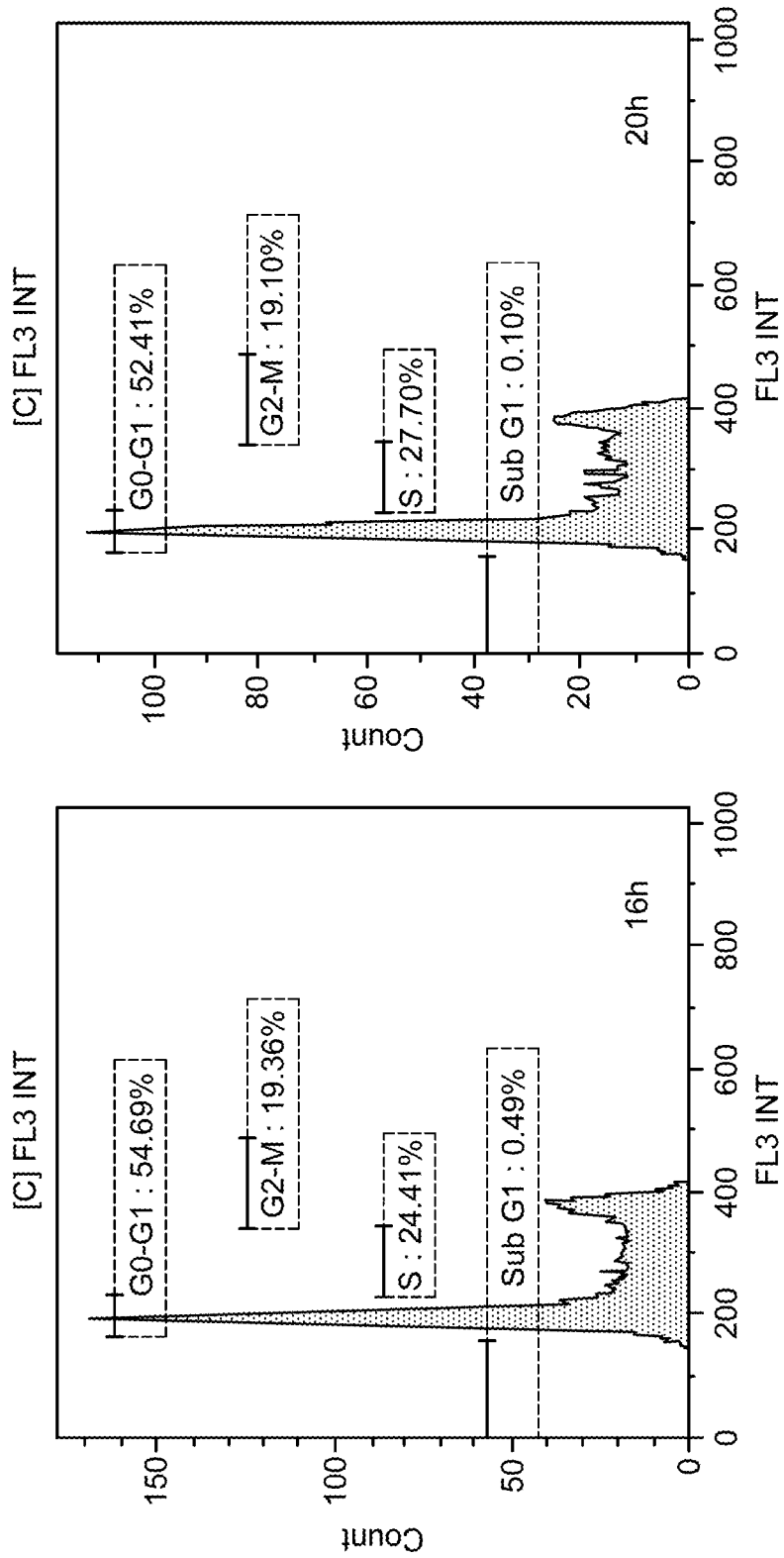
FIG. 3A-3C show characterization of adipose-derived stem cells (ADSCs) in terms of cell cycle and expression of VEGFR-1.
Figure 3A:
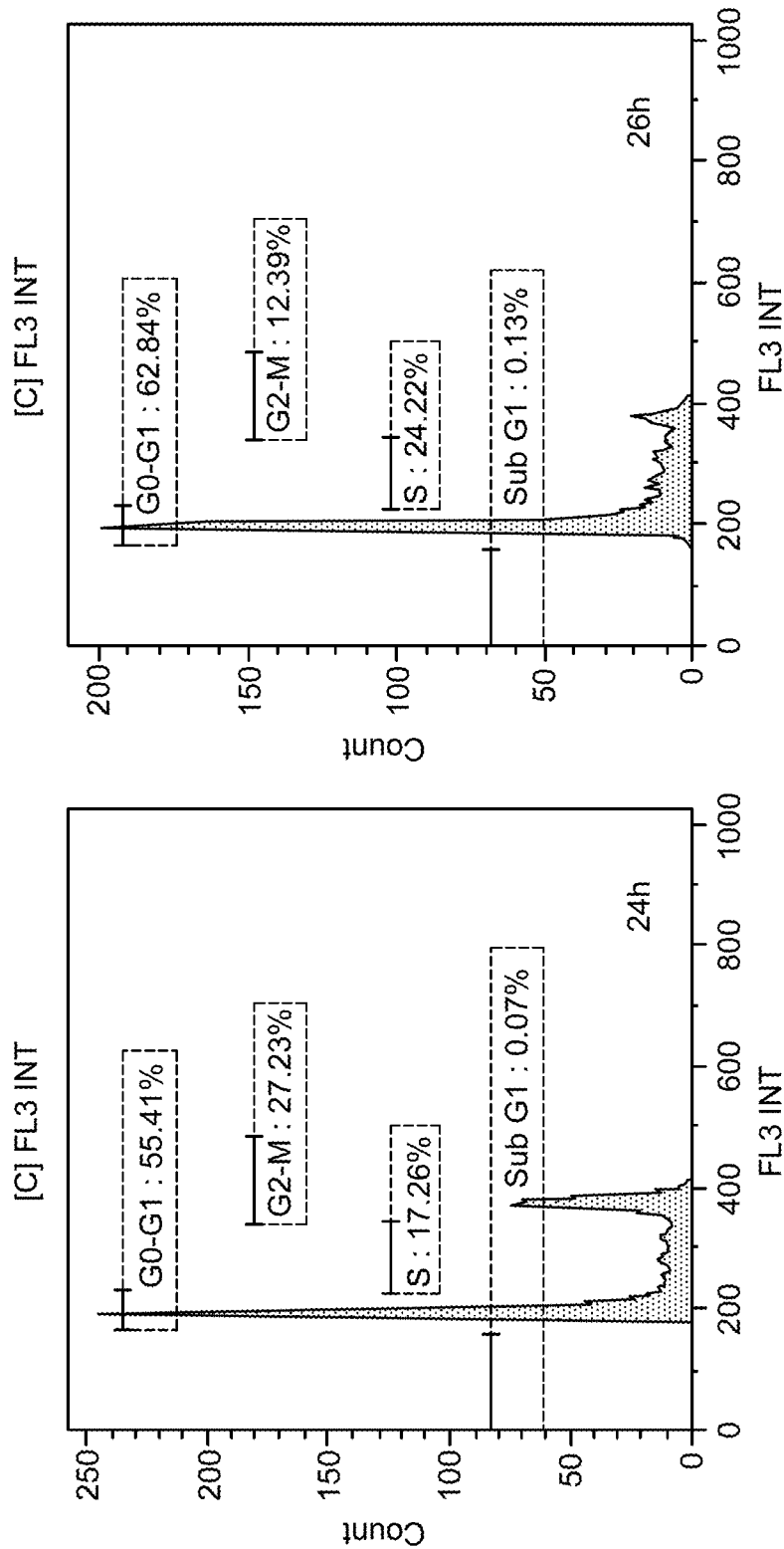
Figure 3A:
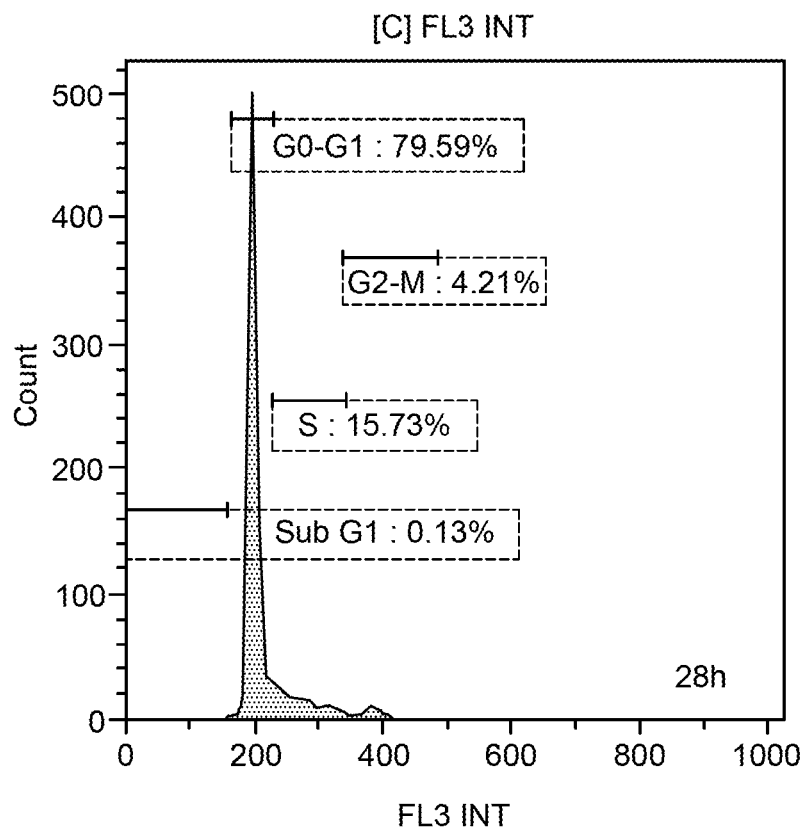
Figure 3B:
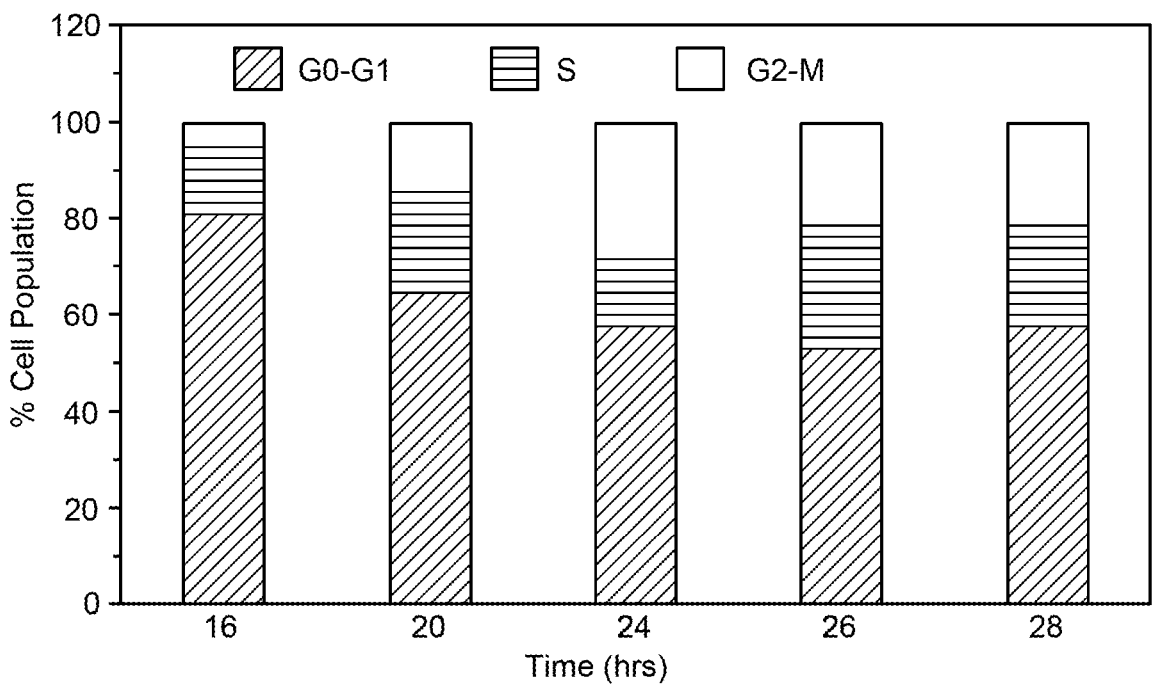
Figure 3C:
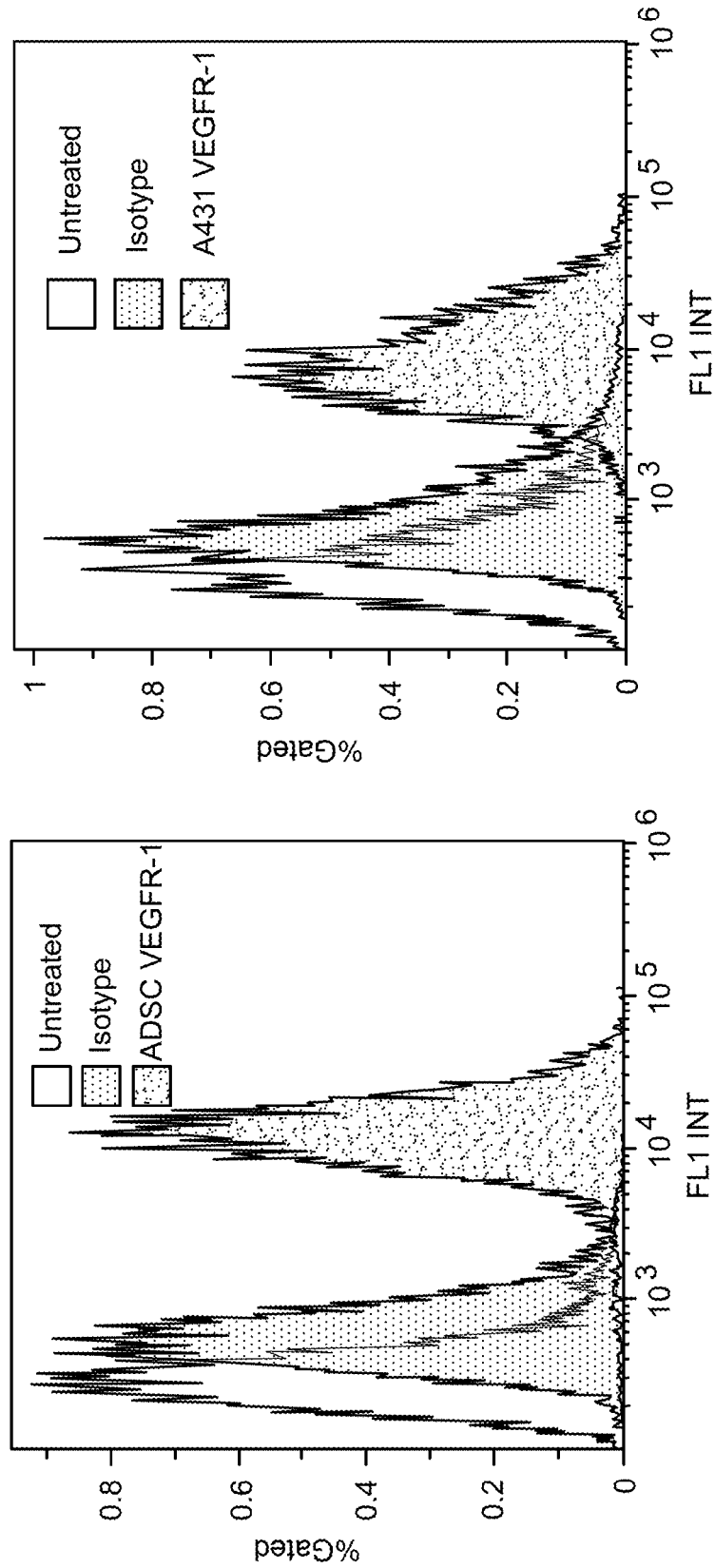
Figure 3C:
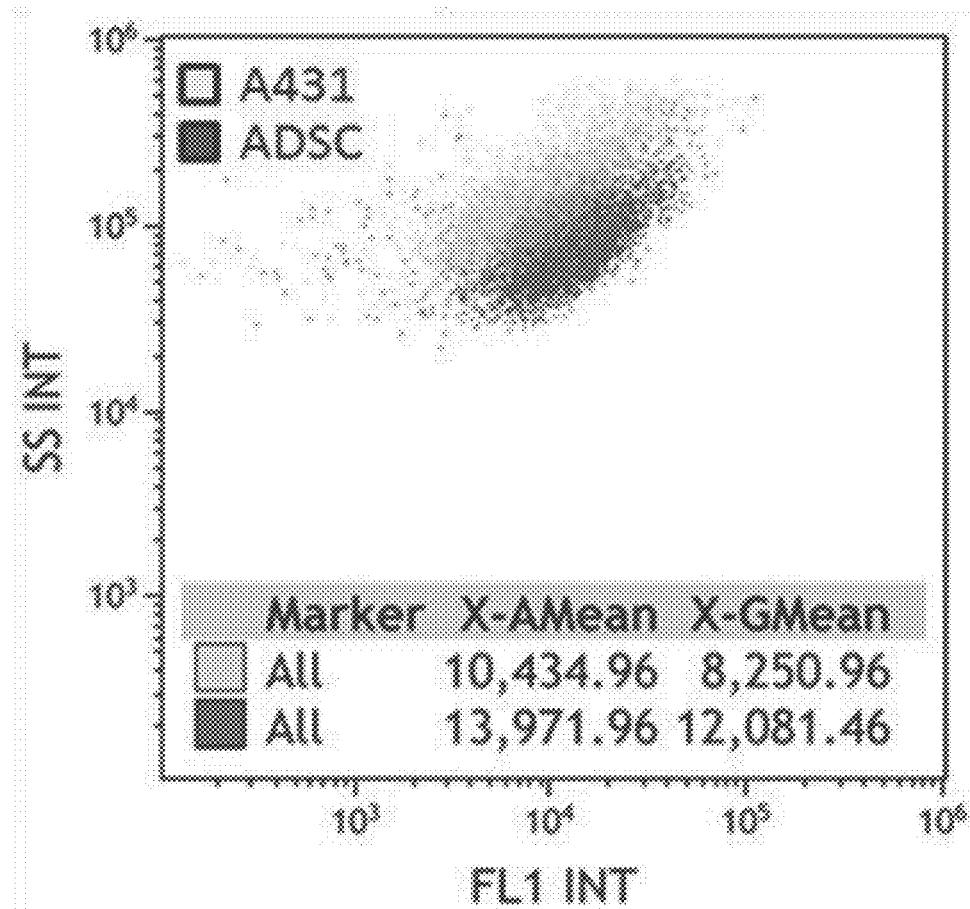

Before cell transfection, we performed a cell cycle analysis to determine the optimum time for transfection of ADSCs since non-viral vectors can mainly transfect dividing cells that are in the mitotic state. For this purpose, we analyzed the cell cycle status of the ADSCs from 16 to 28 hours post-seeding. This study revealed that the optimum time for transfecting ADSCs is 24 hours post-seeding because at this point, significant numbers of ADSCs are in G2-M phase where the nuclear membrane starts dissolving (FIG. 3A-B). Furthermore, we characterized the ADSCs in terms of VEGFR-1 expression to confirm that this receptor is expressed on the surface of ADSCs in abundance. This is important since our targeted DBVs are expected to rely on these receptors for entry into the cells. The results of this study showed a very high expression of VEGFR-1 on the surface of the ADSCs (FIG. 3C). The VEGFR-1 expression level in ADSCs appeared to be even higher than in A431 (human squamous carcinoma) cancer cells which are known to have high expression levels of VEGFR-1[38].

Figure 4A:
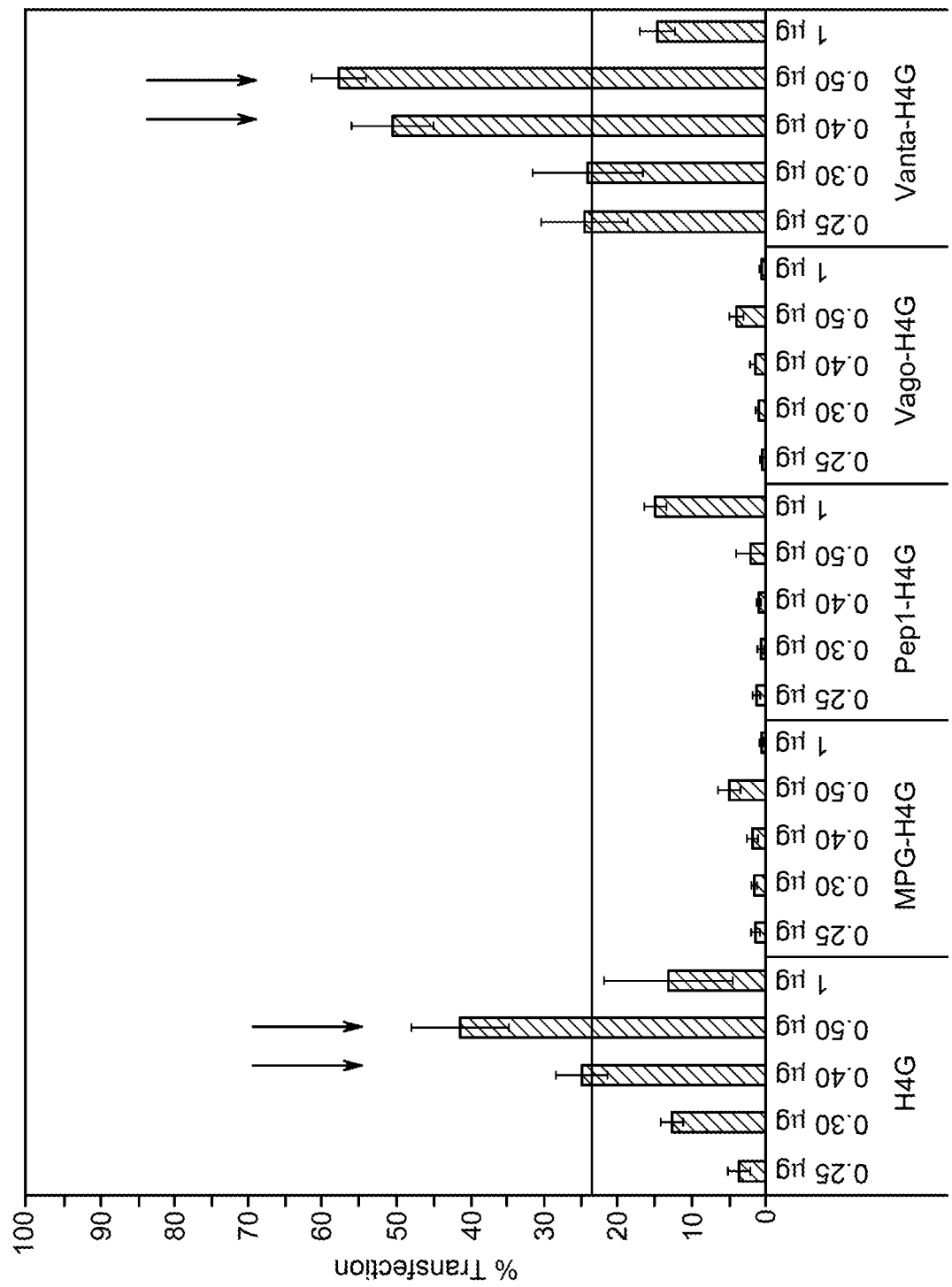
FIGS. 4A-4G are bar graphs showing evaluation of the transfection efficiency and impact on cell proliferation rate of DBVs and commercial vectors.
Figure 4B:
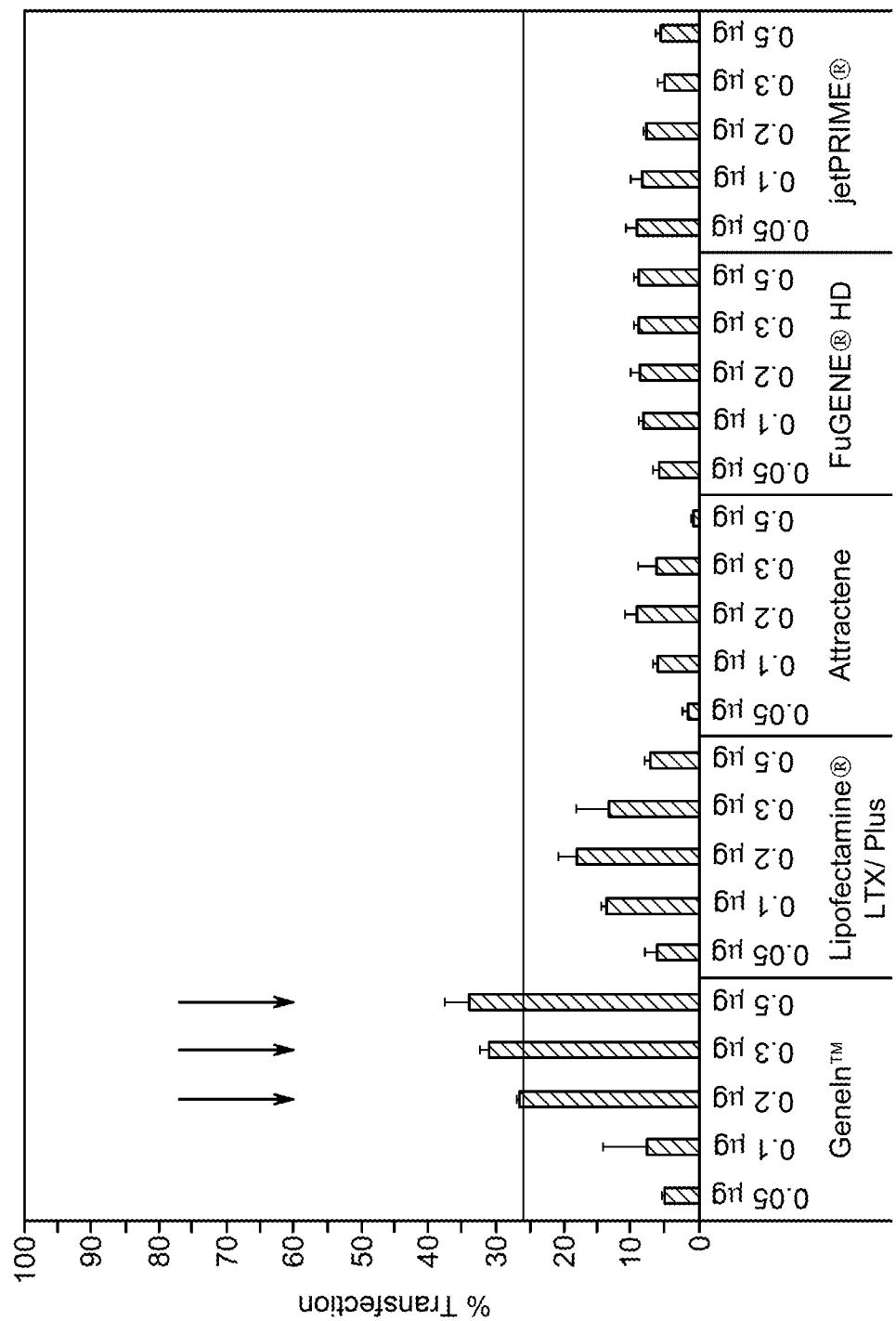
Figure 8A:
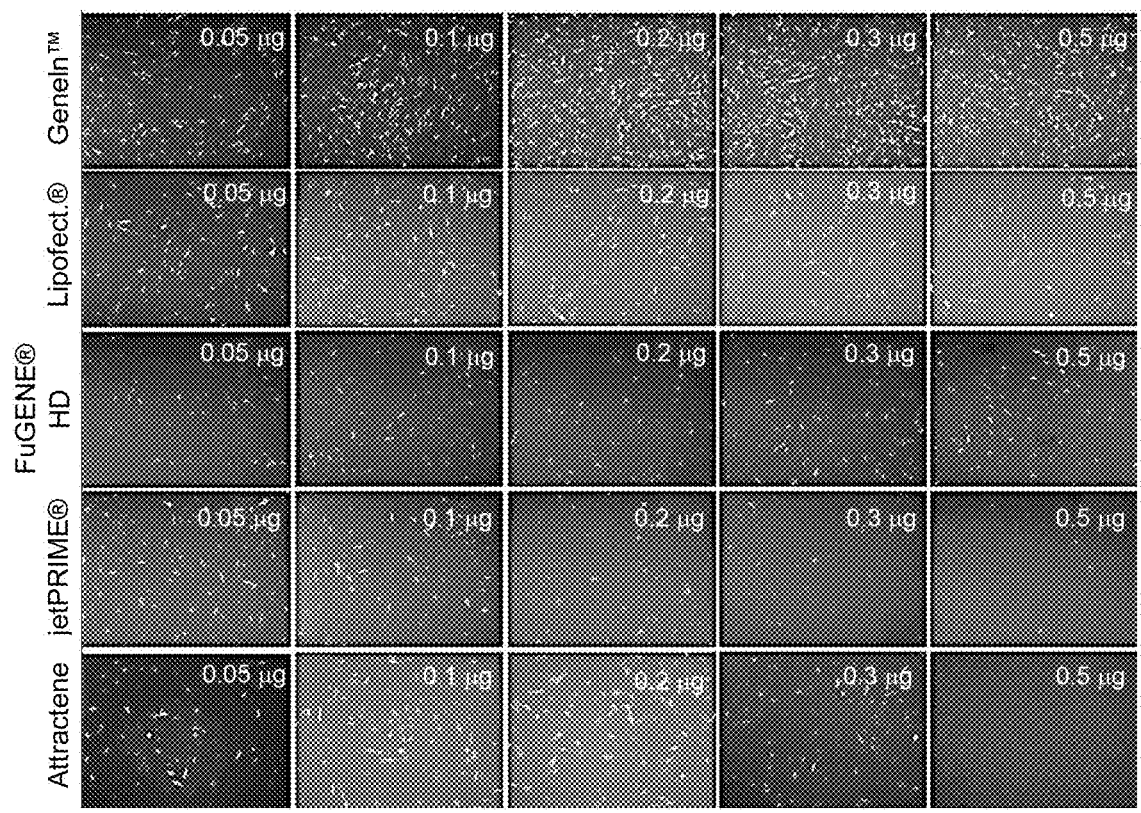
FIGS. 8A and 8B show fluorescent microscopy images of the transfected cells with commercial vectors.
Figure 8B:
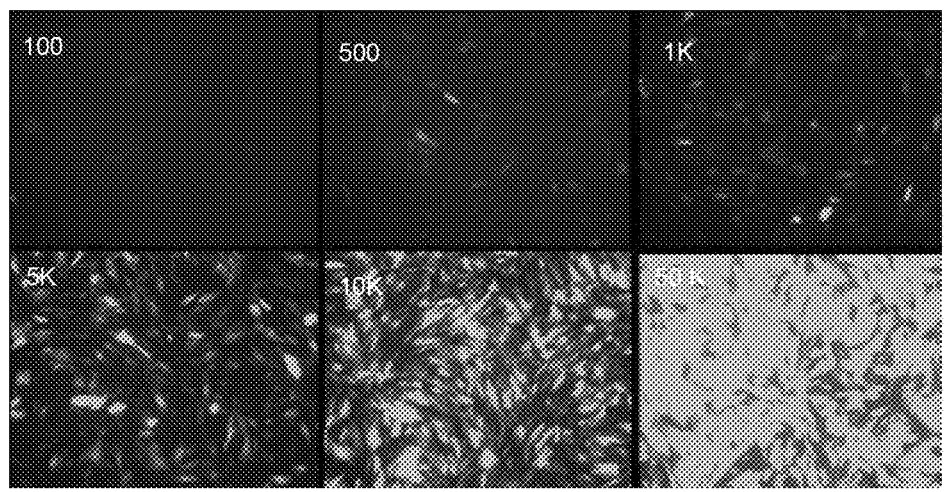
Figure 9:
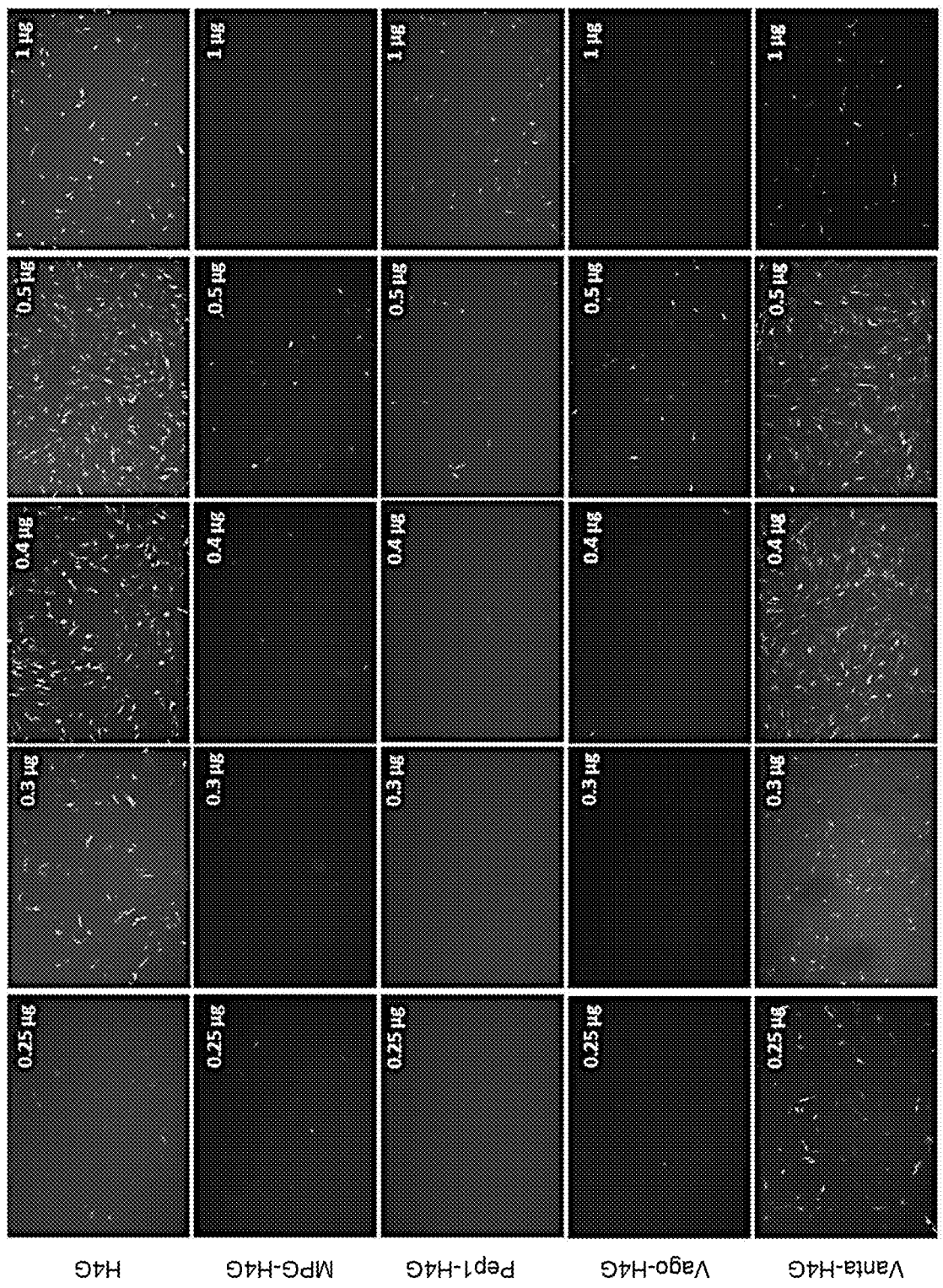
FIG. 9 shows fluorescent microscopy images of the transfected cells with DBVs using different amounts of pEGFP.

Evaluation of Transfection Efficiency, Cell Proliferation Rate, Morphology and Membrane Integrity Learning from the studies mentioned above, we initiated the ADSC transfection studies. Therefore, we used the DBVs (N:P 5) to transfect ADSCs with pEGFP twenty-four hours post-cell seeding. As controls, we also transfected the ADSCs with commercial non-viral and viral vectors to help us better understand the efficiencies of current available vector technologies. Using fluorescent microscopy, we first qualitatively evaluated the transfection rates of the different vectors and noticed there were noticeable differences among the vectors' efficiencies (FIGS. 8A, 8B and 9). This prompted us to use flow cytometry in order to quantify the percentage of transfected cells in each group. For practical purposes and to assist in identifying the most efficient vector, we drew a line at 25% efficiency. This means that the constructs that could transfect ADSCs at rates higher than 25% were considered efficient. It is noteworthy that ADSCs are primary cells and are considered hard to transfect; unlike, easy to transfect cells such as HEK293 or HeLa (FIG. 10). The results of this study demonstrated that the H4G and Vanta-H4G vectors carrying 0.4 and 0.5 µg pEGFP were among the most efficient DBVs with Vanta-H4G surpassing 50% transfection efficiency (FIG. 4A). A complementary cell transfection study using U87 glioblastoma, which does not express the VEGFR-1 receptor[39], confirmed the ability of Vanta-H4G to transfect VEGFR-1 positive ADSCs but not U87 cells (FIG. 11). Among the non-viral commercial vectors, GeneIn™ carrying 0.2, 0.3 and 0.5 µg of pEGFP was the most efficient (FIG. 4B).

One curious observation was that we did not see significant cell transfection rates with the Pep1-H4G and MPG-H4G. Muller et al. (2012), have previously emphasized that not only does the type of cell line determine the cell penetration efficacy of the Pep1 and MPG peptides, but also the chemical nature of the peptides' C-terminus[16]. This means that either the ADSC is not a suitable cell model for transfection by Pep1 and MPG, or the proposed sequences may not have been designed in proper order. If the former is true, then the MPG-H4G and Pep1-H4G vectors should be able to effectively transfect other mammalian cell lines. To examine this hypothesis, we selected Pep1-H4G carrying 0.5 µg pEGFP as an example along with a model fast growing cancer cell line such as SKOV-3 (ovarian cancer). Interestingly, the results showed that Pep1-H4G could transfect SKOV-3 cells up to 35% (FIG. 12). This rate of transfection efficiency is far more than what we observed in ADSCs (i.e., <5%) (FIG. 4A). This shows that the cell type played a significant role in limiting the efficiency of Pep1-H4G and MPG-H4G. To examine whether the positing of Pep1 and MPG at the C-terminus would make a difference, we genetically engineered H4G-Pep1 and H4G-MPG. Unfortunately, due to the co-expression and co-purification of prematurely terminated H4G-Pep1 and H4G-MPG peptide sequences, we could not obtain pure products in order to test the latter hypothesis. Nonetheless, our data shows that ADSCs may not be easily transfected with vectors that are decorated with Pep1 and MPG cell penetrating peptides (CPPs) and perhaps other types of CPPs could produce better results.

Another interesting observation was the inability of the Vago-H4G to efficiently transfect ADSCs. We believe that this could be due to the presence of the three lysine residues in the Vago sequence, especially presence of one at the N-terminus and one at the C-terminus. Cationic charged lysine residues could interact with pDNA inhibiting the protrusion of the VEGFR-1 agonist peptide from the surface of the nanoparticles rendering them unavailable for receptor binding. Considering that a non-cationic high affinity VEGFR-1 agonist is not developed yet, this would be an interesting venue to pursue in order to design the next generation of VEGFR-1 targeted DBVs for stem cell transfection.

Figure 4C:
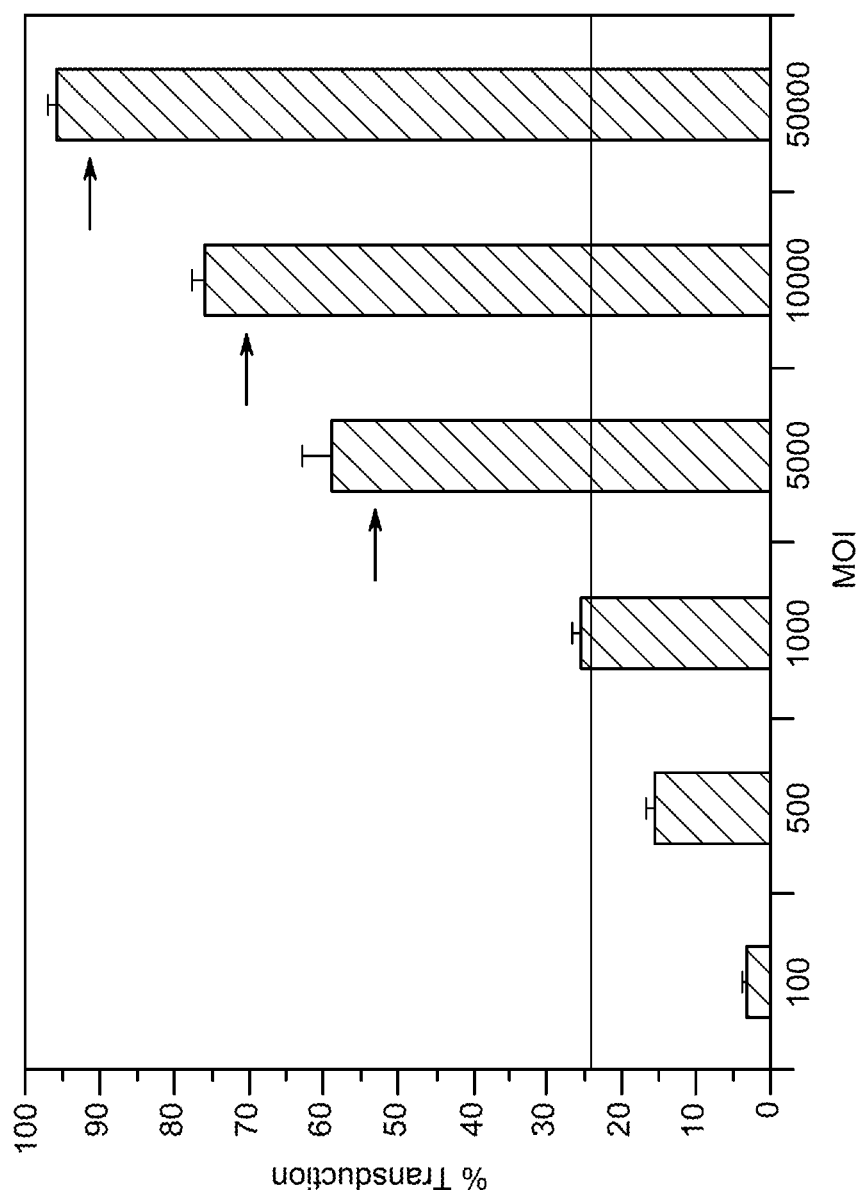

Another unexpected observation was the need to use Ad-GFP at extremely high MOIs (>5K) in order to transfect ADSCs beyond 50% (FIG. 4C). Adenoviral vectors are known to be very efficient in transfecting mammalian cells and can render beyond 50% efficiency at MOIs as low as 50[40]. The fact that such high numbers of adenoviral particles are needed to achieve a high transfection efficiency indicates that the coxsackie adenovirus receptor (CAR) is not expressed in abundance on the surface of ADSCs. Consequently, the downside of using adenoviral vectors at such high MOIs to transfect stem cells is not only the elevated costs, but also the presence of large amounts of viral proteins inside the stem cells which could induce immune response after reintroduction into a patient's body.

Figure 4D:
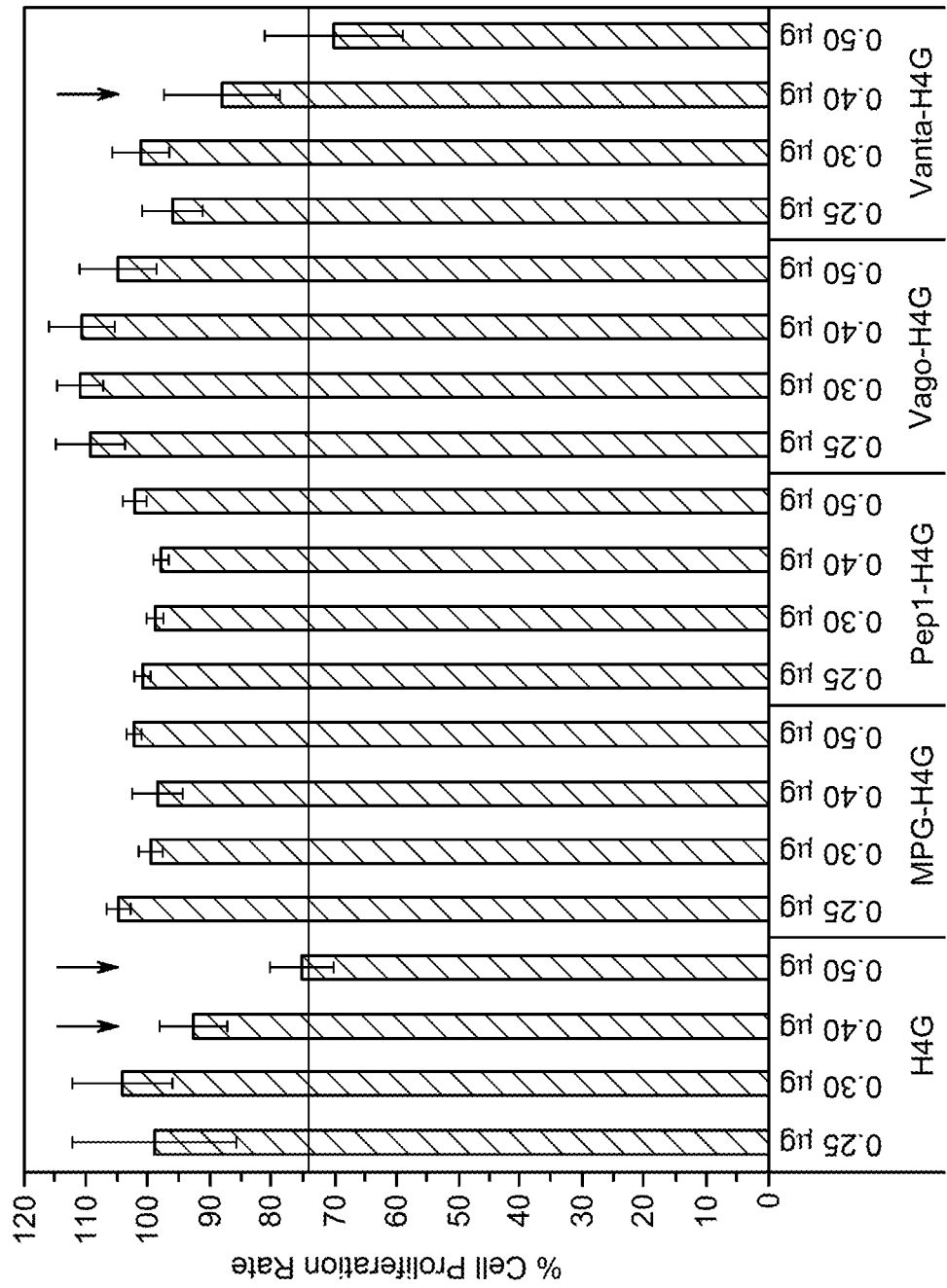
Figure 4E:
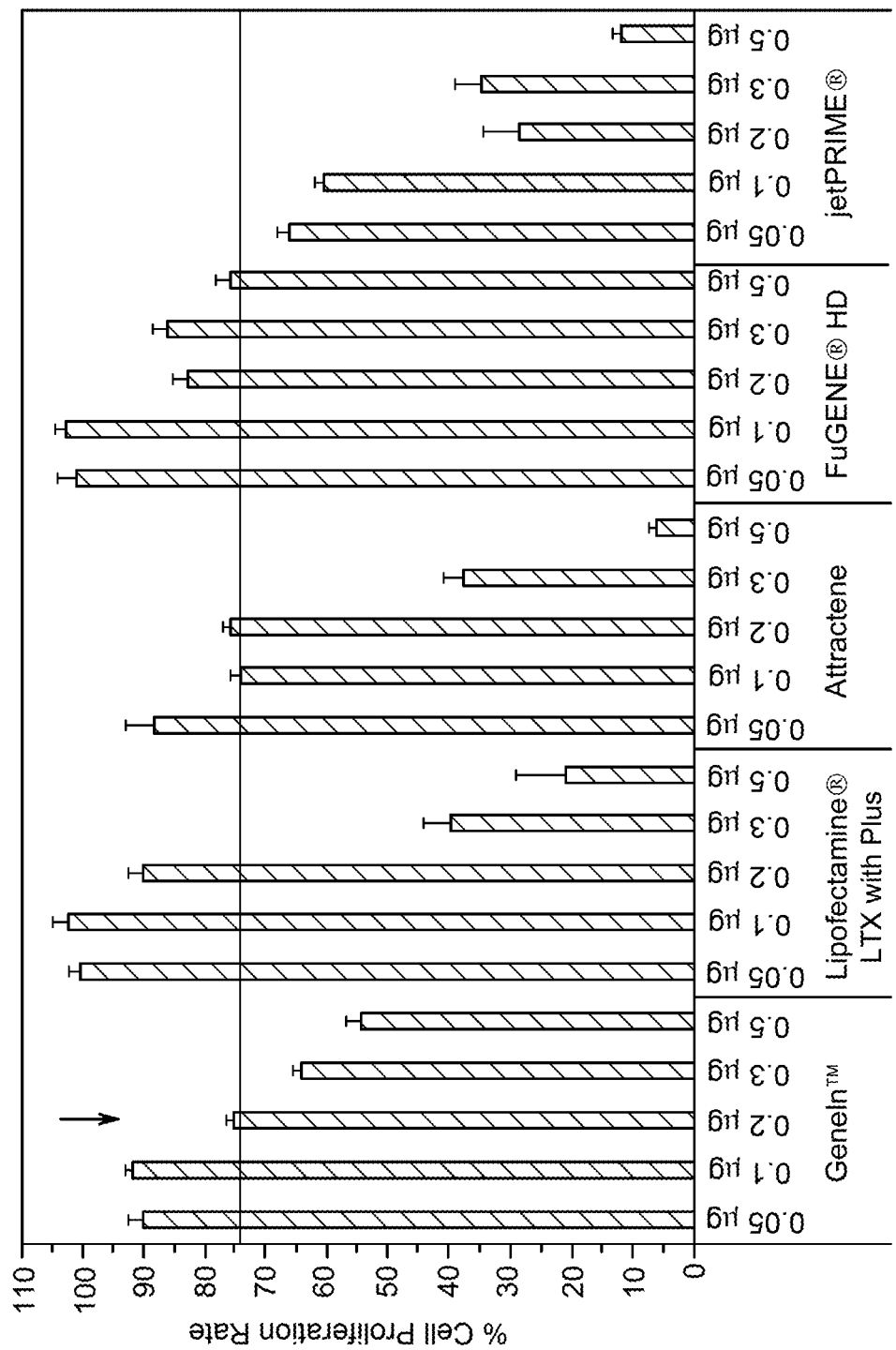
Figure 4F:
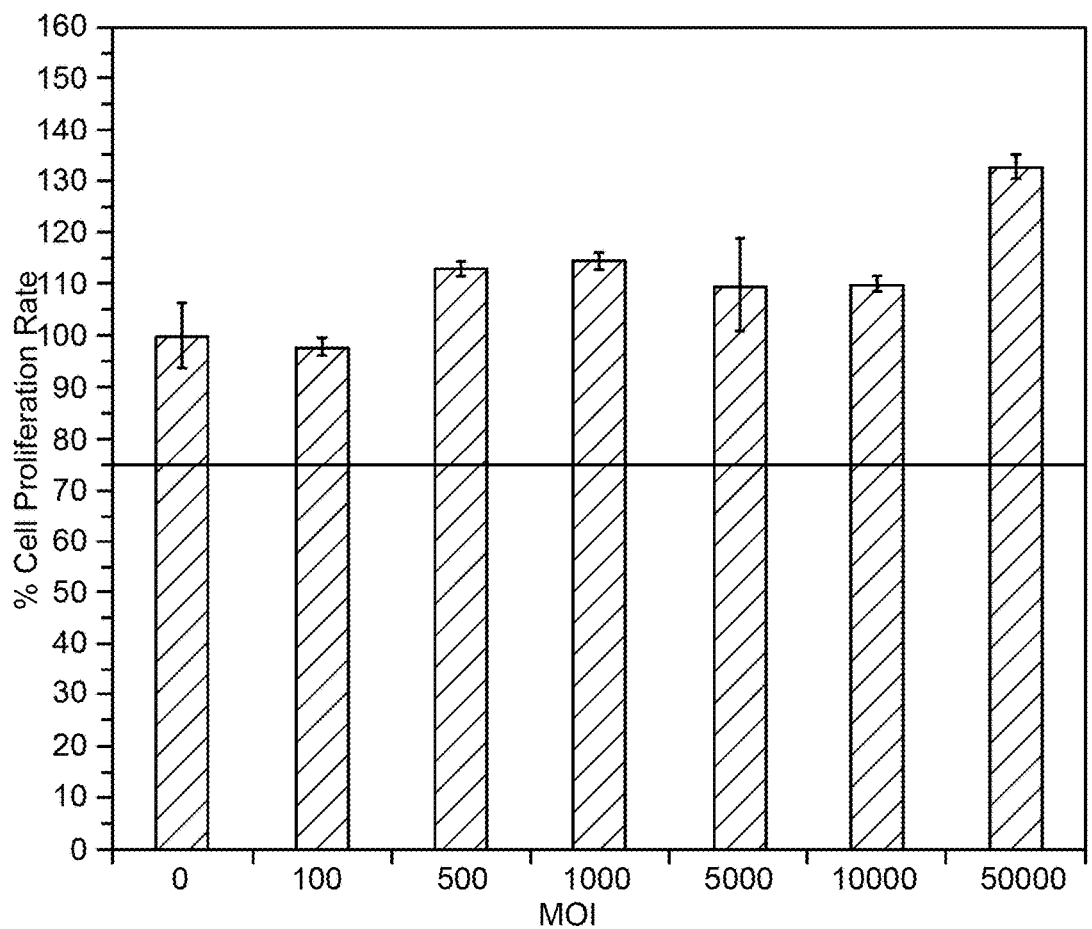

In the next step, we evaluated the impact of the vectors on ADSC proliferation rate. Considering that the formazan based assays such as MTT, MTS, and WST-1 possess potential for side reactions and ambiguities[41], we only eliminated the vectors from the pool that had more than a 25% negative impact on cell proliferation rate. We set this level of tolerance for screening purposes as well as to narrow down the field for more in-depth toxicity studies as later described. The cell proliferation rate study showed that only H4G (0.4 and 0.5 µg pEGFP) and Vanta-H4G (0.4 µg pEGFP) had more than 25% efficiencies and acceptable negative impacts on ADSC proliferation rate (i.e., <25%). Geneln™, carrying 0.2 µg of pEGFP, appeared to be the only viable vector that met our strict efficiency/toxicity guideline for transfecting ADSCs (FIGS. 4D and E). The adenoviral vector rather than showing negative impact on cell proliferation rates at high MOIs, it actually induced cell proliferation (FIG. 4F). This could be explained by the fact that toxic substances in low concentrations occasionally stimulate cellular metabolic activity. In order to protect themselves from such toxicities, cells upregulate their enzymatic activities at the initial stages. Cells will start to die when the concentration of toxic substances, in this case AD-GFP, exceeds their level of tolerance.

Figure 4G:
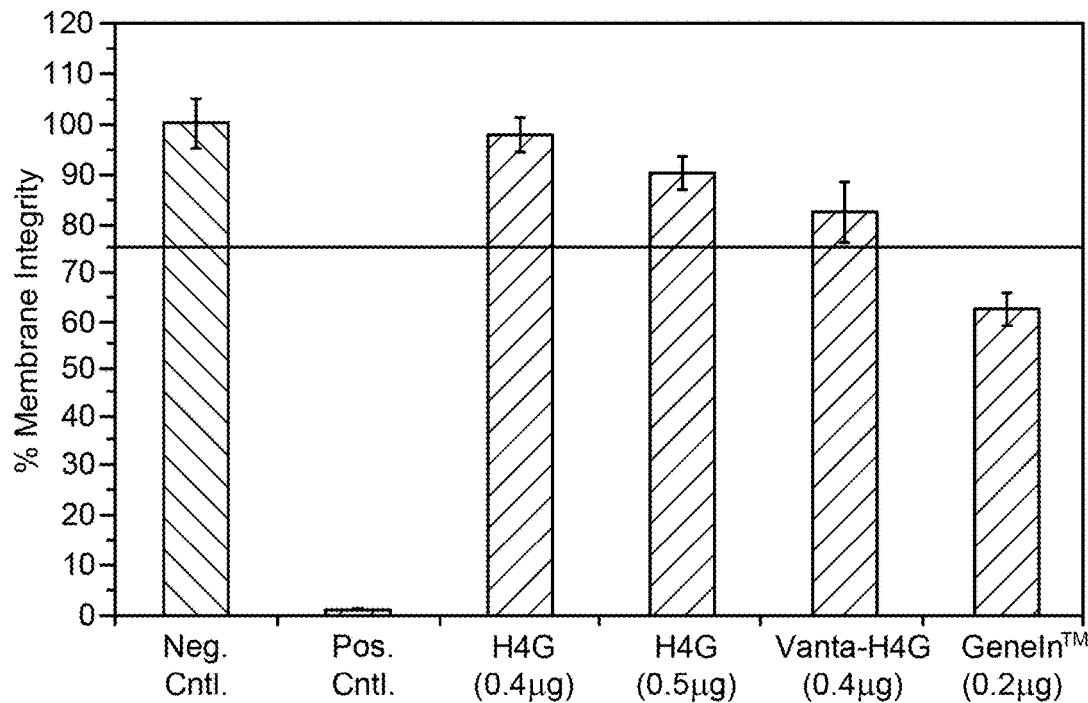

We further characterized the screened and selected vectors from the studies mentioned above in terms of their impact on the cell membrane integrity during transfection. Considering the associated errors with the method and the ability of the cells to recover from the assault, again we set our level of tolerance at 25% negative impact on cell membrane integrity for screening purposes. Given that the non-targeted, positively charged H4G and Geneln™ vectors enter the cells through binding and temporarily disrupting the cell membranes, it is important to investigate whether the cellular entry process results in significant damage to the membrane integrity. Here, we performed an LDH release assay which showed both H4G and Vanta-H4G having minimal impact on the ADSCs membrane integrity (FIG. 4G). This minimal disturbance could be attributed to the low surface positive charge associated with nanoparticles formed through complexation of pEGFP with either H4G or Vanta-H4G. The substantial release of LDH enzyme after transfection of the cells with Geneln™ was somewhat expected as it bears a significantly high surface positive charge (FIG. 2F).

Figure 13:
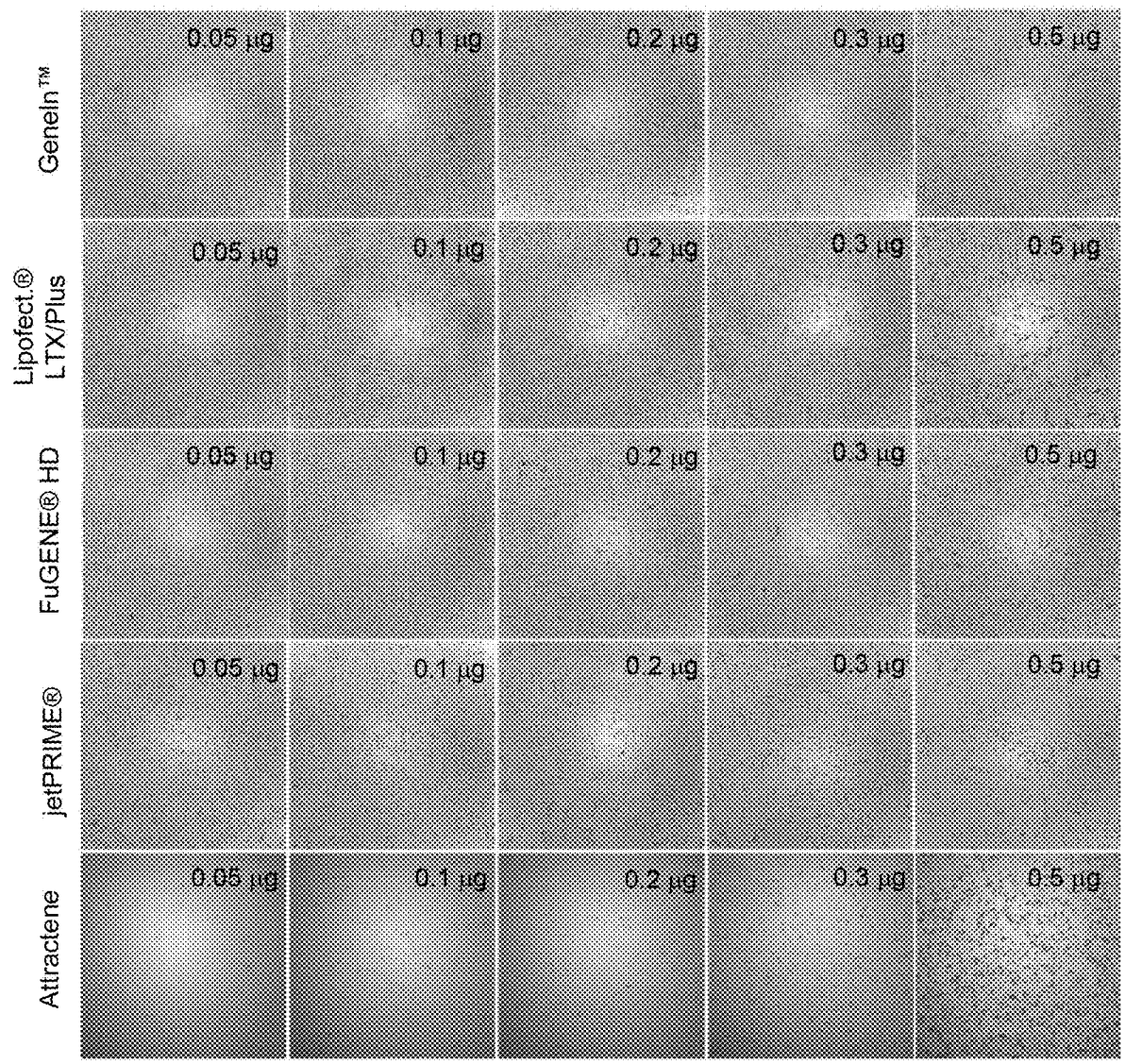
FIG. 13 shows light microscopy images of the transfected cells with commercial vectors carrying different amounts of pEGFP (μg) showing different levels of toxicities.
Figure 14:
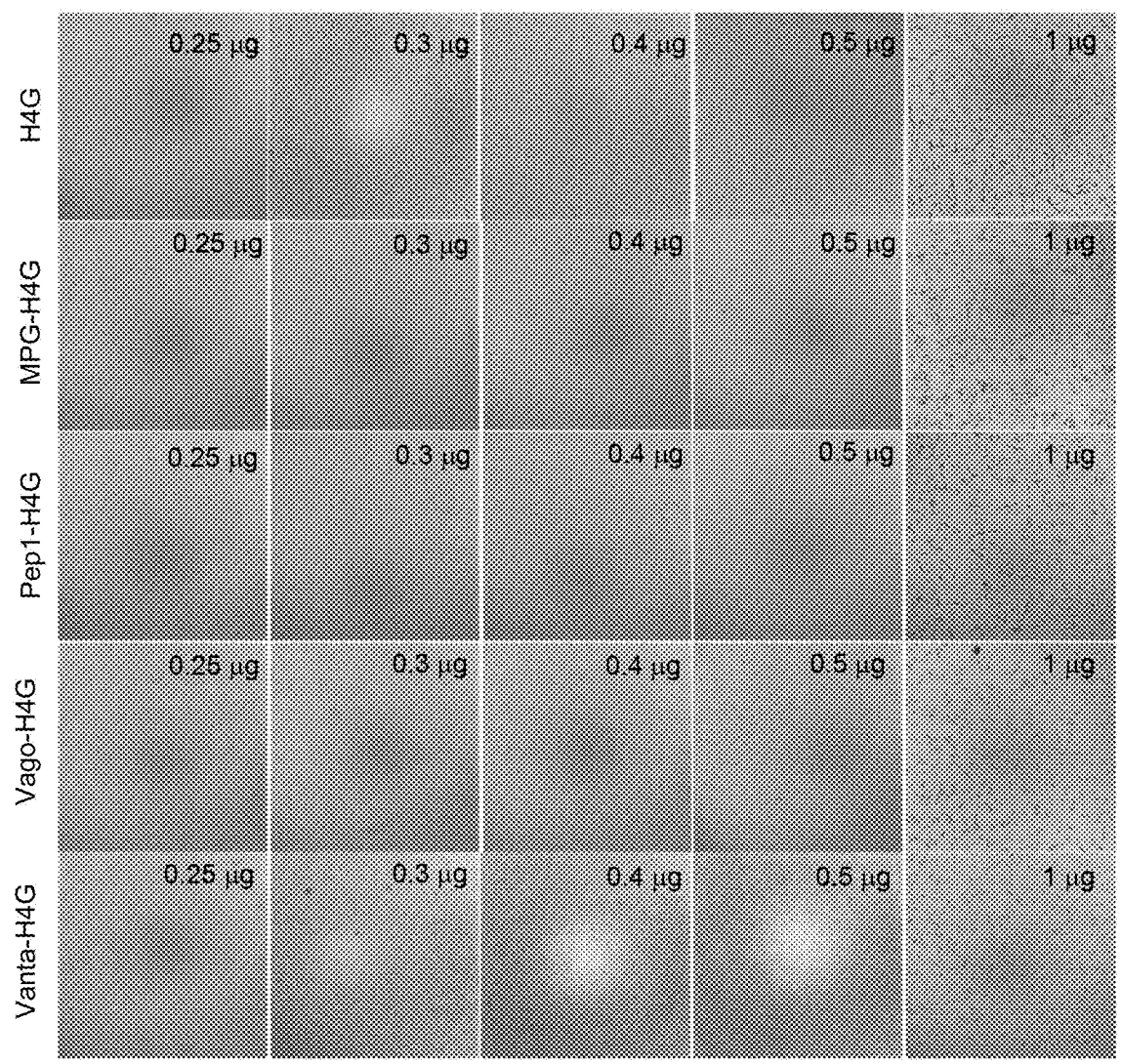
FIG. 14 shows light microscopy images of the transfected cells with DBVs carrying different amounts of pEGFP (μg) showing different levels of toxicities.

At this stage, we also carefully examined the morphology of the ADSCs by a light microscope to ensure that the selected vectors did not induce significant changes to the cells' morphology. The observed pictures clearly show the deleterious effects of certain vector concentrations on the ADSCs, resulting in shrinkage and lysis of the cells. The cell morphology study also confirmed that our selected vectors did not alter the morphology of ADSCs as witnessed by the maintenance of their spindle-like shapes (FIGS. 13 and 14).

Figure 5A:
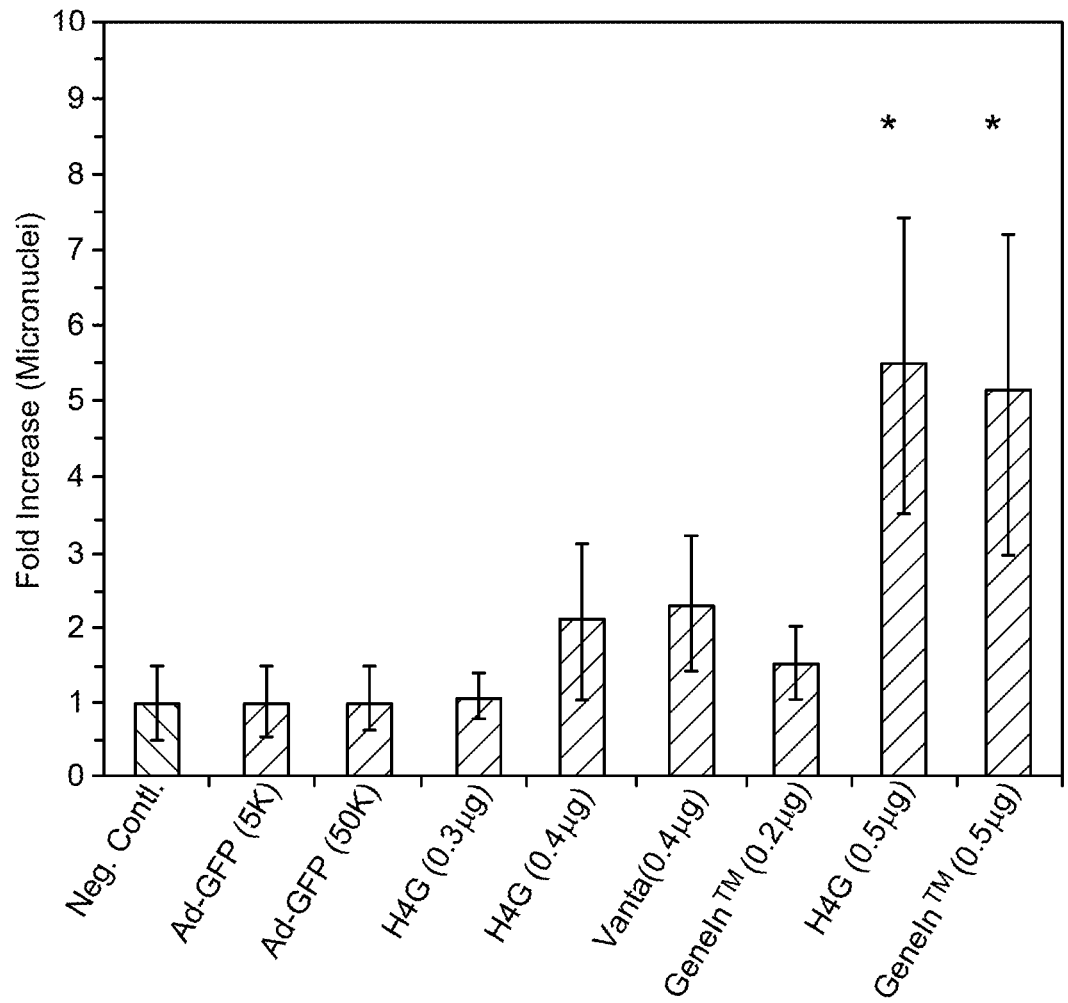
FIGS. 5A-5B.

Evaluation of Vectors' Impact on Micronuclei Formation (Genotoxicity) and Gene Dysregulation In addition to the tests that evaluate the somatic damages to stem cells during and post transfection such as LDH release and cell proliferation assays, it is also critically important to look at the potential aberrations to the genome of the stem cells. In recent years, the need for the evaluation of genotoxicity of gene delivery systems has been highlighted in several published articles[42, 43, 44]. Furthermore, US Food and Drug Administration and International Conference on Harmonization in a published online record (drugs/guidances/ucm074931.pdf), recommend researchers and industries to report a geno-safety profile of pharmaceutical formulation ingredients including nanocarriers[45]. Characterizing micronuclei formation requires an in vitro assay that uses the generation of nuclear blebs and micronuclei in the cytoplasm of interphase cells as an approximation of the cell's genetic instability upon exposure to the reagents. Here, we adapted a flow cytometry based method that could help quantitatively measure the micronuclei formation in transfected cells. From the efficiency/toxicity studies shown above, we identified that the H4G (0.4 and 0.5 µg pDNA) and Vanta-H4G (0.4 µg pDNA) are the most suitable vectors for ADSC transfection. To examine their genotoxicity, ADSCs were transfected with these vectors and the percentages of micronuclei formation were determined. For the negative control, we used the H4G vector carrying 0.3 µg pDNA and as the positive control, we used Geneln™ carrying 0.5 µg of pDNA. Ad-GFP (MOI: 5K and 50K), which bears a negative surface charge and transfects ADSCs via CAR, was also used as negative controls. The selection of the vector controls was based on the data presented in FIG. 4 which shows high toxicity for Geneln™ (0.5 µg pDNA) and low toxicity for H4G (0.3 µg pDNA) and Ad-GFP. Bryce et al. (2007), have previously established that a genotoxic substance would increase the percentage of micronuclei by at least three folds higher than the untreated control group[22]. Based on this guideline, the results of this study showed that H4G (0.5 µg pDNA) and Geneln™ (0.5 µg pDNA) produced significantly higher numbers of micronuclei in transfected ADSCs. Therefore, both vectors were considered genotoxic (*t-test, p<0.05), while all other vectors were non-genotoxic (p>0.05) (FIG. 5A). The result of this study helped us eliminate the H4G (0.5 µg) from the selected vectors despite the fact that the LDH release assay, WST-1 assay, and cell morphology studies had shown that it was acceptable. It was also very interesting to see that the Geneln™ carrying 0.2 µg pDNA did not show any significant genotoxicity despite the previous observations that showed it had some somatic toxicity.

Figure 5B:
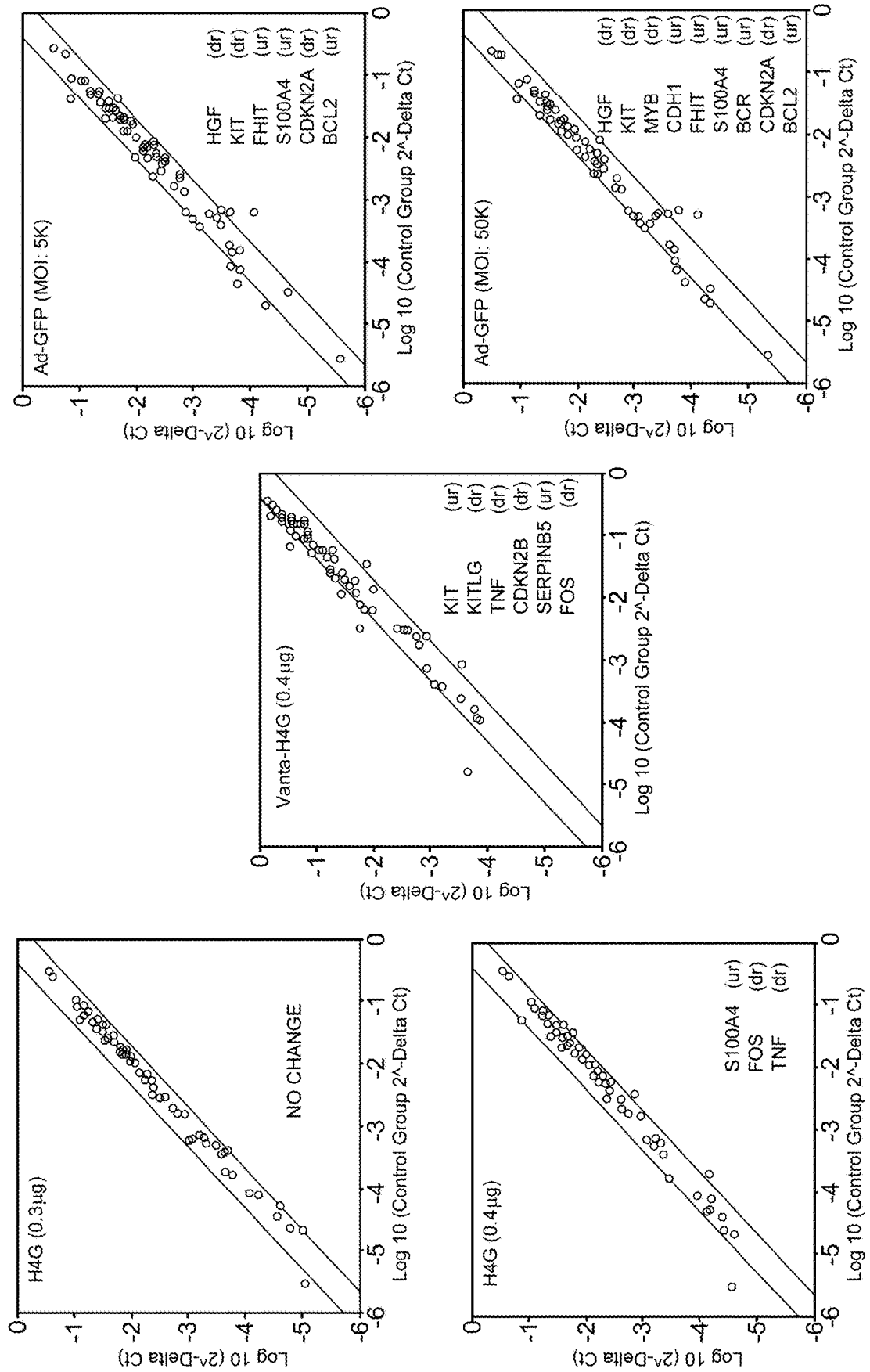

We further examined the effect of DBVs on up/down regulation of genes in ADSCs. Ideally, it is preferred not to observe any significant dysregulation of the host's endogenous genes. Post transfection, we sorted out the strong GFP-positive cells, reseeded, and performed a PCR microarray assay to examine the extent of gene dysregulation in transfected cells. As shown in FIG. 5B, we did not observe any significant change in the genetic pathways of the cells that were transfected with the H4G vector carrying 0.3 µg of pDNA. ADSCs that were transfected with H4G (0.4 µg pDNA) showed dysregulation in three genes out of the eighty four tested. Interestingly, in this group, the S100A4 tumor suppressor gene was upregulated whereas the FOS/TNF gene pathway was downregulated. The FOS gene is a transcription factor, whose expression is most often positively correlated with TNF expression. It has been reported that the up-regulation of the FOS/TNF pathway could increase the probability of mesenchymal stem cell transformation towards malignancy[46]. Considering that there is no negative report on downregulation of FOS/TNF pathway, it may be safe to conclude that such downregulation may reduce the probability of malignant transformation. Similar to the cells in the H4G treated group, cells that were transfected with Vanta-H4G (0.4 µg pDNA), also exhibited down-regulation of the FOS/TNF pathway. Additionally, it was observed that another signaling pathway; i.e., KITLG/

KIT, was up-regulated in this group. Both VEGF/VEGFR and KITLG/KIT signaling pathways play an essential role in stem cell hematopoiesis and new blood vessel formation[47, 48]. Reports also indicate that these pathways share multiple gene cross-talks during signal transduction[48, 49] Since the Vanta-H4G complex competes with VEGF in media for VEGFR-1 binding, the ADSC turns on the alternative KITLG/KIT pathway to adapt to the change. The upregulation of the KITLG/KIT pathway is genetic level evidence supporting the cellular entry of the Vanta-H4G/pDNA nanoparticles through VEGFR binding. The PCR microarray data also showed that few genes were dysregulated within the adenovirus-transduced groups and there is a direct correlation between the MOI and number of dysregulated genes. Furthermore, it was noticeable that in addition to the upregulated BCL2 gene (anti-apoptotic), the genes that promote cell division and growth were down-regulated (HGF, KIT, MYB). The combination of these changes point to potential toxicity of the Ad-GFP to stem cells at such high MOIs. This observation provides genetic level evidence in support of our discussion for FIG. 4F. Overall, the results of genotoxicity assay and microarray analysis shows that none of the selected vectors through the screening process had a significant detrimental effect on the genome of the transfected stem cells validating our approach.

Evaluation of Vectors' Impact on Stem Cell Differentiation

Figure 6A:
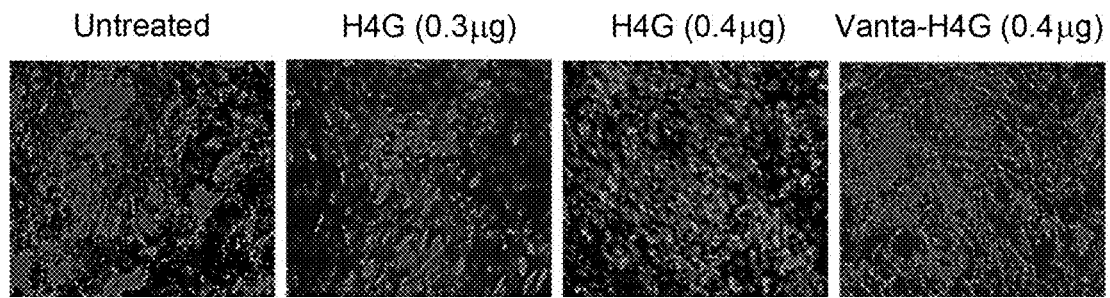
FIGS. 6A-6B: ADSC differentiation into adipocyte.
Figure 6B:
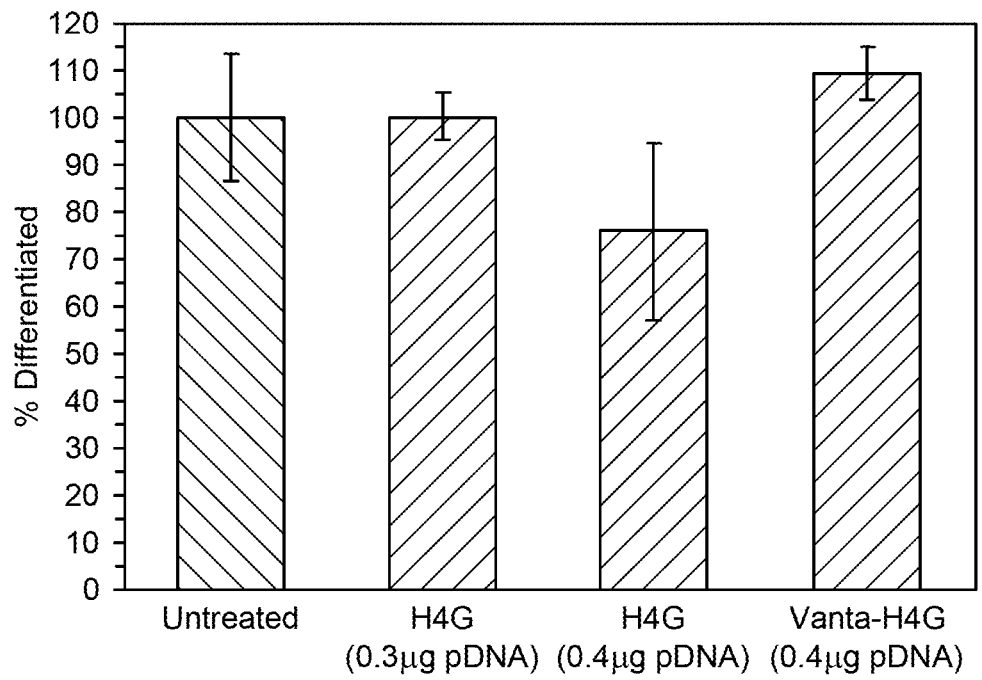

After learning that the H4G (0.3 and 0.4 µg pDNA) and Vanta-H4G (0.4 µg pDNA) groups were not genotoxic, we examined whether they, by any means, negatively affected the ADSCs potential for differentiation. This is important because the objective for the significant number of stem cell engineering studies is to ultimately differentiate them into a tissue. For this purpose, we first transfected the ADSCs with the above mentioned vectors using pEGFP, sorted out the ADSCs that were strongly positive in GFP expression, and then reseeded for differentiation. Here, we sorted the strong GFP-positive cells because these cells received the maximum number of the vector/pDNA nanocomplexes; thereby, demonstrating a higher probability of negative effects. The results of this study showed that none of the vectors negatively affected the ADSCs and the transfected cells could differentiate into adipocytes similar to that of the untreated cells (t-test, p>0.05) (FIG. 6). These observations demonstrate that the developed DBVs could indeed be used for efficient and safe genetic modification of ADSCs without any negative effect on their differentiation into the desired tissue.

Conclusions

The goal of this research was to develop a vector that is not only efficient in stem cell transfection, but also has the ability to maintain such efficiencies without inducing somatic or genetic toxicity. Overall, the efficiency and toxicity data show that among the developed DBVs, the VEGFR-1 targeted Vanta-H4G is not only the most efficient vector for ADSC transfection (~50% efficiency), but also one without any significant negative impact on physical integrity, metabolic activity, genetic composition, and cell differentiation. Considering that the adenoviral vector which is also a targeted vector, could efficiently transfect stem cells with minimal short-term toxicity, it may be safe to conclude that the best approach towards transfecting stem cells efficiently and safely is through receptor targeting rather than entry through a cellular membrane. The developed Vanta-H4G could potentially be used to transfect any mammalian cell line that overexpresses VEGFR-1.

In Example 1, the terms "vector" or "fusion vector" are used interchangeably with "fusion polypeptide".

EXAMPLE 2

Figure 15:
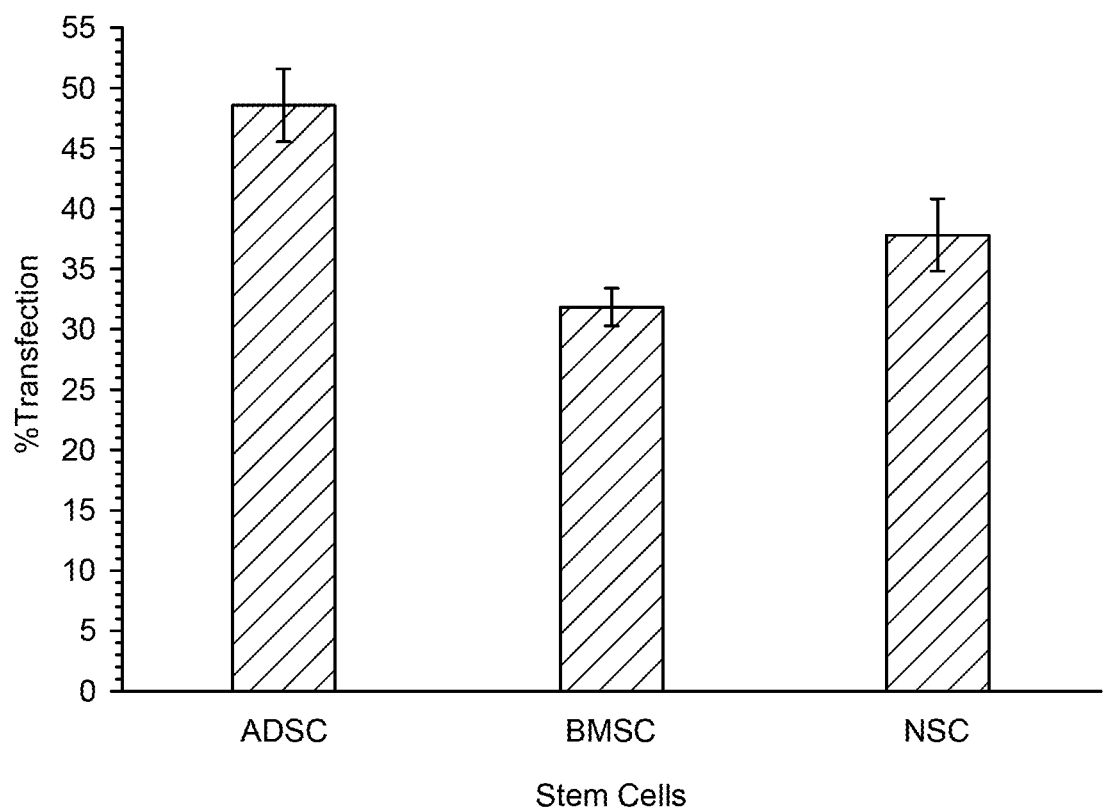
FIG. 15 shows a bar chart that quantitatively demonstrates the percentage of transfected cells using Vanta-H4G. Transfection of ADSCs, bone marrow-derived stem cells (BMSCs) and neural stem cells (NSCs) by using Vanta-H4G with 0.4 μg of pEGFP. The results show that Vanta-H4G can transfect all three cell lines with high efficiency. The data are presented as mean±s.d. (n=3).

We seeded ADSCs, BMSCs, and NSCs in 96-well plates and transfected them with Vanta-H4G in complexation with 0.4 µg of pEGFP. The results of this study showed that Vanta-H4G can transfect all three cell lines with high efficiency confirming its broad application in stem cell engineering (FIG. 15).

Transfection of ADSCs, BMSCs and NSCs by using Vanta-H4G in complexation with 0.4 µg of pEGFP. This figure shows that Vanta-H4G can transfect all three cell lines with high transfection efficiency, ranging from, e.g., about 30% to about 50% (such as about 30%, about 37%, about 50%, etc.).

We also examined the efficiency of "Lipofectamine Stem" and "Lipofectamine 3000" (ThermoFisher Scientific) for transfecting stem cells.

Transfection of ADSCs by Lipofectamine Stem

Following the vendor's protocol, ADSCs were seeded at the density of 6000 cells per well (n=3) in a 96-well plate. 100 ng pEGFP was complexed with 0.4 µl Reagent in Opti-MEM media. Cells were transfected and observed under fluorescent microscope 48 hours post transfection. The results of this study showed that Lipofectamine Stem could not transfect stem cells efficiently. Based on the fluorescent microscopy images, the transfection efficiency was estimated to be below 5% and was not analyzed further due to its very low efficiency.

Transfection of ADSCs by Lipofectamine 3000

Figure 16A:
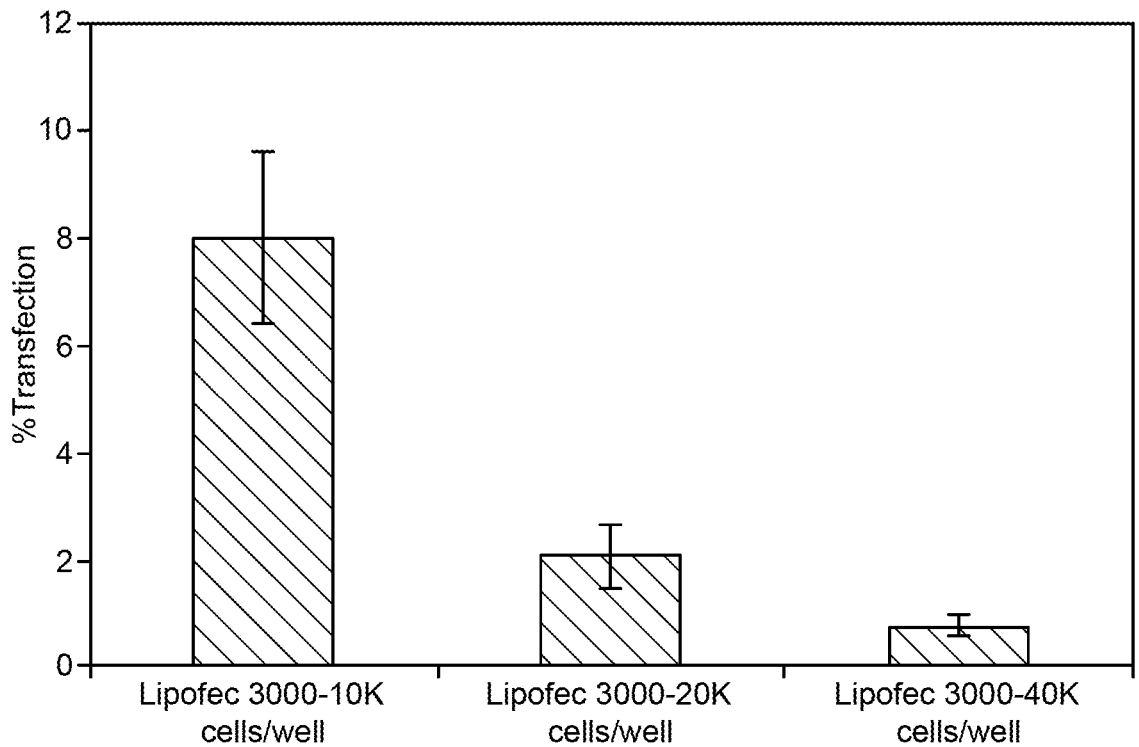
FIGS. 16A-16B show the transfection efficiency and cell viability of ADSC cells transfected with 100 ng pEGFP using Lipofectamine 3000.
Figure 16B:
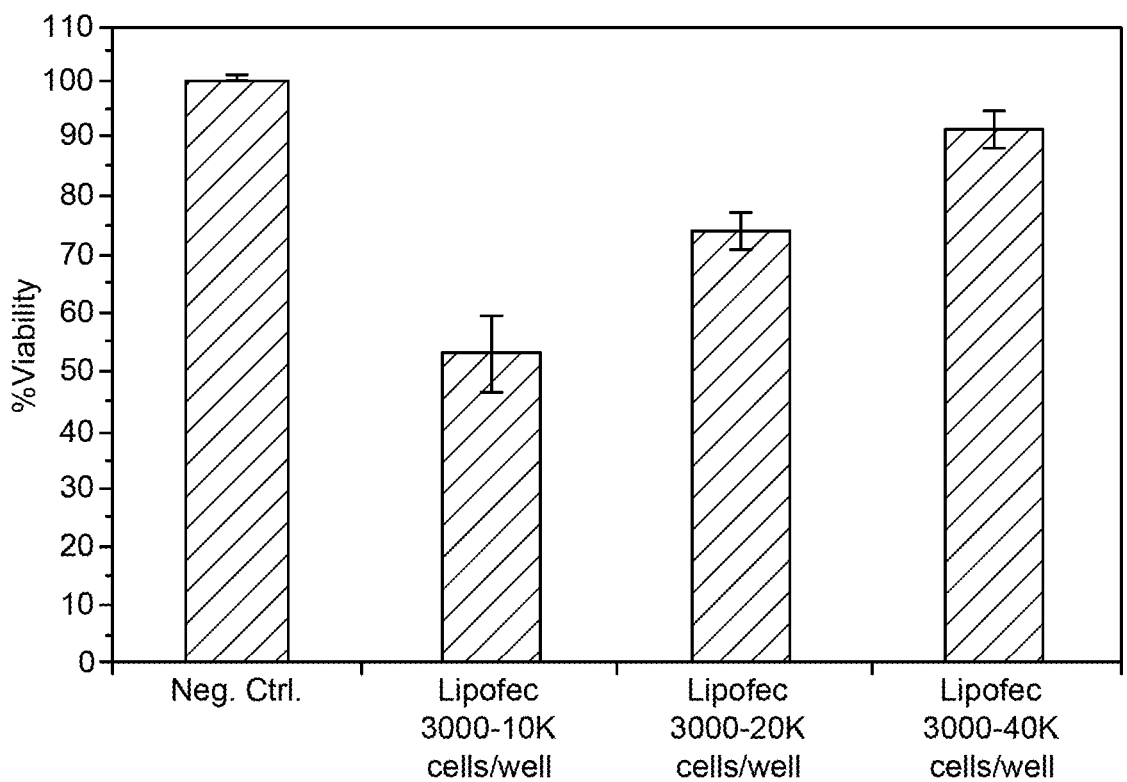

Lipofectamine 3000 was purchased from ThermoFisher Scientific. Following vendor's protocol, the following numbers of ADSCs were seeded in a 96-well plate: 10,000/well; 20,000/well; and 40,000/well. Based on the vendor's recommendation, 100ng of plasmid DNA (pEGFP) was complexed with Lipofectamine 3000 and used to transfect ADSCs. The percentages of transfected ADSCs as well as cell viability were determined by flow cytometry. As shown in FIGS. 16A-16B, the highest rate of transfection efficiency was observed when 10,000 cells were seeded in a 96-well plate and transfected with 100 ng of pEGFP. The transfection efficiency ranged from about 0.8% to about 8%. These results show that Lipofectamine 3000 is not only inefficient but also toxic and not a suitable vector for stem cell transfection.

Recently, the leading commercial non-viral vectors have been shown to be genotoxic. Nomani A., Chen X. and Hatefi A., Evaluation of genotoxicity and mutagenic effects of vector/DNA nanocomplexes in transfected mesenchymal stem cells by flow cytometry, Acta Biomaterialia 74 (2018) 236-246.

EXAMPLE 3

Genetic Engineering and Production of Recombinant Vectors

We use standard genetic engineering techniques similar to our previous reports in order to clone, express, and purify the DBVs 18, 19, 20. In brief, the genes encoding IGFR-H4G, FGFR-H4G, EGFR-H4G, PDGFR-H4G, INTEGRIN-H4G with 6×-histidine tag (SEQ ID NO: 249) at the c-terminus, were designed and are then chemically synthesized. The corresponding amino acid sequences of the vectors are shown in Table 1. The genes are restriction digested by NdeI and XhoI enzymes and cloned into a pET21b bacterial expression vector (Novagen®, EMD Millipore, Mass., US). The fidelity of each gene sequence to the original design is verified by DNA sequencing.

To express the vectors, the expression plasmids are transformed into the LOBSTR BL21(DE3) *E. coli* expression strain (Kerafast Inc., MA, US). The protein expression protocol is optimized for the production of highly cationic vectors in *E. coli* as described previously by our group[21]. In brief, one colony is picked from the LB agar plate and inoculated overnight in a 5 ml Miller's LB media supplemented with 100 µg/mL carbenicillin (Sigma-Aldrich, MO, US). The next day, the starter culture is transferred into 500 mL terrific broth (TB) supplemented with 100 µg/mL carbenicillin. The culture is incubated at 37° C. under vigorous shaking until the $OD_{600}$ reached 0.4-0.6. To induce protein expression, isopropyl β-D-1-thiogalactopyranoside (IPTG, Teknova, Calif., US) is added to the culture at the final concentration of 1 mM. After 2.5-4 hours of induction, the *E. Coli* pellet is collected by centrifugation at 5000 g, weighed and stored in −80° C. freezer.

To purify the peptides, a method based on Ni-NTA immobilized metal affinity chromatography (QIAGEN, Md., US) is developed. A lysis buffer is formulated beforehand, containing 8 M urea, 2 M NaCl, 100 mM $NaH_2PO_4$, 10 mM Tris, 1% (v/v) Triton X-100, and 10 mM imidazole. The bacterial pellet is lysed by the lysis buffer (5 mL buffer per 1 gram pellet) for one hour at room temperature under vigorous stirring. Then, the supernatant is collected by centrifuging the slurry for one hour, at 20,000 rpm, 4° C. Meanwhile, the Ni-NTA resin is washed with 10 mL distilled/deionized water and preconditioned with 2 mL of lysis buffer. Afterwards, the supernatant is mixed with the preconditioned Ni-NTA resin and incubated on ice with gentle shaking. After one hour of incubation, the mixture is diluted with 3 times lysis buffer and passed through a 10-mL polypropylene filter column (Bio-Rad Inc., US) by vacuum driven filtration. The column is washed by 100 mL of lysis buffer followed by 50 mL wash buffer (5 M Urea, 1.5 M NaCl, 100 mM $NaH_2PO_4$, 10 mM Tris and 40 mM imidazole). Finally, the purified vector is eluted by 5 mL of elution buffer (3 M Urea, 0.5 M NaCl, 100 mM $NaH_2PO_4$, 10 mM Tris and 300 mM imidazole) and collected in 500 µL fractions. The concentration of the peptide within each fraction is measured by the Nanodrop 2000 spectrophotometer (Thermo Fisher Scientific, US). The purity of each peptide is determined by SDS-PAGE analysis.

Peptide Desalting and Preparation of Stock Solution

To desalt, a disposable PD-10 desalting column with Sephadex G-25 resin (GE Healthcare's Life Sciences, MA, US) is preconditioned with 15 mL of 10 mM L-Glu/L-Arg buffer (pH 5.8-6.0). Then, each purified peptide fraction is loaded onto the column and eluted with additional 5 mL of buffer driven by gravity. The concentration of each peptide is measured by Nanodrop 2000 spectrophotometer (Thermo Fisher Scientific, US) using the molecular weight and corresponding extinction coefficient as calculated by the ProtParam tool from the ExPASy Bioinformatics Resource Portal. The conductivity of the peptide solution is determined by Laser Doppler Velocimetry using Malvern Nano-ZS Zetasizer (Malvern Instruments, UK).

Nanoparticle Formation and Particle Size, Charge and Shape Analysis

The DNA/peptides nanoparticles are formed by the Flash Mixing method[19]. In brief, the required amount of each peptide to condense 1 µg of pEGFP plasmid DNA (pDNA) at various N:P ratios is calculated beforehand. Then, pEGFP is diluted to a volume of 50 µL using distilled/deionized water. Concurrently, predetermined amount of each peptide is diluted to 50 µL volume using distilled/deionized water and placed in another microfuge tube. The peptide solution is added to the pDNA solution rapidly and flash mixed. After 5-10 minutes of incubation, the nanoparticle size is measured by Dynamic Light Scattering and surface charge by Laser Doppler Velocimetry using Malvern Nano-ZS Zetasizer (Malvern Instruments, UK). To make nanoparticles with the commercial transfection reagents including GeneIn™ (MTI-GlobalStem, MD, US), Lipofectamine® LTX with Plus (Thermo Fisher Scientific, MA, US), Attractene (QIAGEN, Md., US), FuGENE® HD (Promega Corporation, WI, US) and jetPRIME® (Polyplus-transfection, France), we follow the corresponding manufacturers' protocols. Once nanoparticles are formed, the surface charges are measured in 5 mM NaCl solution. The data are presented as mean±s.d. (n=3). Each mean is the average of 15 measurements while n represents the number of independent batches prepared for the measurements.

To study the morphology of the nanoparticles, transmission electron microscopy (TEM) is utilized[19]. First, nanoparticles are formed and then one drop of the mixture is loaded onto a carbon type B coated copper grid. As soon as the sample dry on the surface, the solution of 1% sodium phosphotungstate is added to stain the nanoparticles. The detailed images are recorded by 1200EX electron microscope (JEOL, US).

ADSC, BMSC, NSC Characterization

The ADSCs, BMSCs (Lonza, N.J., US) and NSCs (ATCC, VA, US) were cultured in their corresponding growth medium which contains the basal media and the necessary supplements for proliferation of human mesenchymal and neural stem cells.

ADSCs, BMSCs and NSCs were characterized for cell cycle and VEGFR-1, IG1-R-1, EGFR, and FG1-R-2 expression by flow cytometry. The cell cycle study was performed using propidium iodide (PI) DNA staining protocol. In brief, cells were seeded in 96-well plates at the density of 6000 cells per well. After 16, 20, 24, 26, 28 hours of incubation with growth medium at 37° C. and 5% $CO_2$, cells were detached through trypsinization. Cells were then fixed by 70% cold ethanol. After 1 hour, cells were collected by centrifugation, re-suspended in PBS and treated with 0.5 mg/mL Rnase A. Finally, cells were stained by PI (10 µg/mL) for 1 hour. The cell cycle distribution was determined by flow cytometry (Beckman Coulter GALLIOS Cytometer, CA, US).

To determine the level of VEGFR-1 expression, ADSCs were detached by Accutase® Cell Detachment Solution (Innovative Cell Technologies, CA, US). Cells were fixed by 4% formaldehyde solution in PBS and then permeabilized by 0.1% Tween 20/PBS solution. Cells were washed and re-suspended in the staining buffer (0.3M glycine and 10% normal goat serum in PBS solution). 2 µL of Anti-VEGFR-1 rabbit monoclonal antibody conjugated with Alexa Fluor® 488 (abcam, MA, US) was added to each sample. Rabbit monoclonal IgG conjugated with Alexa Fluor® 488 (abcam, MA, US) was used as isotype control. Samples were incubated overnight at 4° C. and then washed extensively with PBS. The expression level of VEGFR-1 was determined by flow cytometry (Beckman Coulter GALLIOS Cytometer, CA, US). The unstained sample was also included as a negative control.

To examine the potential application of the developed vector in transfecting bone marrow-derived stem cells (BMSCs) and neural stem cells (NSCs), we characterized these cell lines in terms of VEGFR-1 expression. In addition, we evaluated the expression levels of other growth factor receptors such as insulin-growth factor receptor-1 (IG1-R-1), epidermal growth factor receptor (EGFR) and basic fibroblast growth factor receptor (FGFR-2). Using fluorescently labeled antibodies against these receptors, we labeled the cells and analyzed the expression of receptors by flow cytometry. For this experiment, stem cells were incubated with Anti-VEGFR-1, Anti-IGFR-1, Anti-EGFR, and Anti-FGFR-2 monoclonal antibodies conjugated with Alexa Fluor® 488. Monoclonal IgG conjugated with Alexa Fluor® 488 was used as isotype control. The expression level of each receptor was determined by flow cytometry. The unstained sample was used as negative control. The results of this experiment showed that almost all ADSCs, BMSCs and NSCs express VEGFR-1, FGFR-2, EGFR, and IGFR-1 receptors. Although at different densities, these receptors are expressed in high copy numbers on the surfaces of these cell lines.

Evaluation of Cell Transfection Efficiency

The day before transfection, ADSCs and BMSCs and NSCs are seeded in 96-well tissue culture plates at the densities of 6000, 6000 and 25,000 cells per well, respectively. In a microfuge tube, nanoparticles are prepared at various N:P ratios as described above in a total volume of 50 µL and incubated for 5-10 minutes at room temperature. Each tube is further supplemented with 200 µL of basal media (without serum), 1 µM dexamethasone (Sigma-Aldrich, MO, US) and 1×ITS Liquid Media. A 100×ITS solution includes 1.0 mg/mL recombinant human insulin, 0.55 mg/mL human transferrin and 0.5 µg/mL sodium selenite (Sigma-Aldrich, MO, US Next, the old media in each well is removed and replaced with the 250 µL nanoparticle mixture. Twenty-four hours post transfection, the media in each well is replaced with 200 µL full growth media and the cells are allowed to grow for another twenty-four hours. The green fluorescent protein (GFP) expression is visualized and qualitatively evaluated by a fluorescent microscope (Olympus, Fla., US). To quantify GFP expression and percent transfection, cells are trypsinized and analyzed by flow cytometry (Beckman Coulter CytoFLEX Cytometer, CA, US). The ratio of GFP positive cells to untransfected cells is calculated by Kaluza flow analysis software (Beckman Coulter, Calif., US). The data are presented as mean±s.d. (n=3).

Evaluation of Vectors' Impact on Cell Proliferation Rate, Membrane Integrity and Morphology The impact of each vector on ADSC, BMSC and NSC proliferation rates is evaluated by the WST-1 cell proliferation assay. Cells are seeded in the 96-well plates. After twenty four hours of incubation, cells are transfected with vectors as described above. Forty eight hours post-transfection, the old media is replaced with 100 µL of fresh media containing 10 µL WST-1 reagent (1:10 dilution). After one hour of incubation at 37° C./5% CO2, the absorbance of each well is measured by Infinite® M200 PRO NanoQuant microplate reader (Tecan, Switzerland) at 440 nm/600 nm. The absorbance of each treatment is normalized to the negative control (untreated cells) to measure the percentage of cell viability.

To evaluate the impact of each vector on cell membrane integrity, a lactate dehydrogenase (LDH) release assay (Roche, Ind., US) is performed using manufacturer's kit and protocol. In brief, cells were seeded and transfected as described above. Cells are incubated in stem cell basal media for 48 hours post transfection since the LDH reagent is not compatible with serum. Media in each well is removed and centrifuged at 250 g for 5 minutes to pellet the debris. The supernatants are collected into a 96-well plate with 100 µL per well. Next, 100 µL LDH reagent is added into each well and incubated for 30 minutes at room temperature. The absorbance at wavelengths of 490 nm and 600 nm is measured using Infinite® M200 PRO NanoQuant (Tecan, Switzerland) microplate reader. The media, without contacting any cells, serves as the background control. The media from the untransfected cells is used as the negative control (spontaneous LDH release). The media from the cells incubated with the 2% Triton X-100 serves as the positive control (maximum LDH release). After subtracting the background control, the percentage of impact on membrane integrity is calculated as follows: % membrane integrity= (Positive-Treatment)/(Positive-Negative)×100. The data are presented as mean±s.d. (n=3).

The morphology of stem cells before and after transfection is studied by using phase-contrast microscopy (Olympus, Fla., US).

Evaluation of Vectors' Impact on Micronuclei Formation (Genotoxicity)

To quantify the percentage of micronuclei formation, cells are seeded and transfected as described above. Twenty four hours post-transfection (equivalent to 1-1.5 doubling time), cells are harvested and stained using an In Vitro Micro-Flow® Kit (Litron Lab., NY). The staining is performed according to the manufacturer's protocol with several modifications. Briefly, cells are detached, transferred into a microfuge tube, and centrifuged for 6 min at 300 g. The supernatant is removed and the pellet is placed on ice for 20 min. Next, cells are resuspended in 50 µL of ethidium monoazide (EMA) solvent (Dye A). EMA is a DNA staining fluorescent dye that cannot pass through the cell membrane of live cells. As a result, it can only stain the late apoptotic or dead cells helping to distinguish them from live cells. After 30 min of incubation with EMA, cells are washed by the Kit's wash buffer, lysed by lysis buffer, and treated with RNase enzyme. Cells are then exposed to SYTOX green fluorescent dye that stains all nuclei and micronuclei. The lysis and SYTOX green staining process is performed at 37° C. while samples were protected from light. After staining, samples are analyzed by CytoFlex Flow Cytometer (Beckman Coulter, Brea, Calif.) using an optimized acquisition protocol according to the guideline of In Vitro Microflow® Kit. The detailed information about the gating protocol can be found elsewhere[22]. Briefly, the process starts by gating all events from side scatter vs. forward scatter plots and continues with the second plot in which the doublet nuclei are discriminated and excluded by FITC width vs. FITC area plot. Next, the SYTOX Green positive events are selected. This excludes other interfering events, such as smaller fluorescent particles, green fluorescent protein aggregates, and stained plasmids or nanoparticles. In general, micronuclei are defined as events showing $\frac{1}{10}$ to $\frac{1}{100}$ of the mean intensity of SYTOX Green fluorescence found in nuclei of viable (i.e. EMA-negative) cells. The gating protocols are kept unchanged during the analysis and for each sample, at least 1000 EMA negative nuclei events are counted. Accordingly, % MN=Number of MN/Number of viable nuclei×100. The data are presented as mean±s.d. (n=4).

Determination of Vectors' Impact on Gene Regulation (Microarray Analysis)

The effects of vectors on the expression of 84 genes associated with cell growth regulation are analyzed by using the Human Genes RT² Profiler™ PCR Array (Qiagen, Md., US). The names of the tested genes are as follows: SERPINB5, MYCN, ABL1, AKT1, APC, ATM, BAX, BCL2, BCL2L1, BCR, BRCA1, BRCA2, CASP8, CCND1, CDH1, CDK4, CDKN1A, CDKN2A, CDKN2B, CDKN3, CTNNB1, E2F1, EGF, ELK1, ERBB2, ESR1, ETS1, FHIT, FOS, FOXD3, HGF, HIC1, HRAS, IGF2R, JAK2, JUN, JUNB, JUND, KIT, KITLG, KRAS, MCL1, MDM2, MEN1, MET, MGMT, MLH1, MOS, MYB, MYC, NF1, NF2, NFKB1, NFKBIA, NRAS, PIK3C2A, PIK3CA, PML, PRKCA, RAF1, RARA, RASSF1, RB1, REL, RET, ROS1, RUNX1, RUNX3, S100A4, SH3PXD2A, SMAD4, SRC, STAT3, STK11, TGFB1, TNF, TP53, TP73, TSC1, VHL, WT1, WWOX, XRCC1, ZHX2. Stem cells are seeded in the 96-well plates and then transfected with selected DBVs. Four hours post transduction, the media is removed and replaced with full growth media. Forty eight hours after, cells are collected and the GFP positive cells are separated from the general population by the Moflo XDP Cell Sorter (Beckman Coulter, Calif., US). The GFP positive cells are reseeded in a 6-well plate at the density of 45,000 cells per well and allowed to fully recover from the process until they reach 80% confluency (4 to 8 days). The mRNAs of transfected and untransfected cells are extracted by RNeasy Mini Kit (Qiagen, Md., US). The genome DNA is eliminated by the RNase-Free DNase Set (Qiagen, Md., US) during the RNA isolation process. The concentration and purity of mRNA are evaluated by measuring the absorbance at wavelength 260 nm and 280 nm. Concurrently, an agarose gel (1%) electrophoresis is performed to examine the mRNA integrity. Then, 0.5 µg of mRNA is reverse transcribed into complementary DNA (cDNA) by RT$^2$ First Strand Kit (Qiagen, Md., US). The cDNA of each sample with RT$^2$ SYBR Green ROX PCR Master mix (Qiagen, Md., US) is loaded onto the PCR array. The real-time PCR reactions are performed using StepOnePlus™ Real-Time PCR System (Thermo Fisher Scientific, MA, US). The program settings on temperature cycling are followed as instructed by the manufacturer. The raw data and gene profile expression is analyzed by "Double Delta Ct Method" using the manufacturer's online software tool. Here, five housekeeping genes (ACTB, B2M, GAPDH, HPRT1 and RPLP0) are used as controls. All experiments are performed in triplicates while a two-fold change in RNA levels served as the cut-off point (*, $p<0.05$).

Evaluation of Vectors' Impact on ADSC Differentiation

To examine whether the transfection process has a negative impact on stem cell differentiation, the cells are induced to differentiate into adipocytes. Cells are transfected with the developed vectors and after 48 h post-transfection, are harvested and sorted by flow cytometry according to their respective GFP expression. The sorted GFP-positive cells are then reseeded in 96-well plates and incubated at 37° C. with stem cell full media. The media is changed every other day until cells reached maximum confluency. At this point, the stem cells' full growth media is removed and replaced with adipogenesis differentiation media cocktail (Lonza Inc., NJ) containing 1 µM dexamethasone, 0.5 mM isobutyl-methylxanthine (IBMX), 1 µg/ml insulin, and 100 µM indomethacin. The differentiation media is gently replaced every 3 days for 12 days. Next, ADSCs are washed by PBS and stained with AdipoRed™ fluorescent staining reagent (Lonza Inc., NJ). The production of intracellular oil vesicles is visualized by fluorescent microscopy (Olympus Co., USA) and the percentage of differentiated stem cells is quantified by flow cytometry. Untransfected stem cells are subjected to the same differentiation protocol and used as the positive control. The data are presented as mean±s.d. (n=3).

TABLE 1

The amino acid sequences of the designed recombinant vectors for stem cell transfection.

| Name | Cell Targeting Peptide | Cell Penetrating Peptide | DNA Condensing Motif (H4) | Fusogenic Peptide (GALA) |
|---|---|---|---|---|
| H4G | N/A | N/A | (SGRGKQGGKARAK AKTRSSRAGLQFPV GRVHRLLRK)4 (SEQ ID NO: 5) | WEAALAEALAEALA EHLAEALAEALEAL AA (SEQ ID NO: 6) |
| MPG-H4G | N/A | GALFLGFLGAAGSTMG AWSQPKKKRKV (SEQ ID NO: 3) | (SGRGKQGGKARAK AKTRSSRAGLQFPV GRVHRLLRK)4 (SEQ ID NO: 5) | WEAALAEALAEALA EHLAEALAEALEAL AA (SEQ ID NO: 6) |
| Pep1-H4G | N/A | KETWWETWWTEWSQPK KKRKV (SEQ ID NO: 4) | (SGRGKQGGKARAK AKTRSSRAGLQFPV GRVHRLLRK)4 (SEQ ID NO: 5) | WEAALAEALAEALA EHLAEALAEALEAL AA (SEQ ID NO: 6) |
| Vago-H4G | KLTWQELYQKLYKGI (SEQ ID NO: 1) | N/A | (SGRGKQGGKARAK AKTRSSRAGLQFPV GRVHRLLRK)4 (SEQ ID NO: 5) | WEAALAEALAEALA EHLAEALAEALEAL AA (SEQ ID NO: 6) |
| Vanta-H4G | NGYEIEWYSWVTHG MY (SEQ ID NO: 2) | N/A | (SGRGKQGGKARAK AKTRSSRAGLQFPV GRVHRLLRK)4 (SEQ ID NO: 5) | WEAALAEALAEALA EHLAEALAEALEAL AA (SEQ ID NO: 6) |
| IGFR-H4G | LLGDFFRKSKEKIG KEFKRIVQRIKDFL RNLVPRTES (SEQ ID NO: 17) | N/A | (SGRGKQGGKARAK AKTRSSRAGLQFPV GRVHRLLRK)4 (SEQ ID NO: 5) | WEAALAEALAEALA EHLAEALAEALEAL AA (SEQ ID NO: 6) |
| FGFR-H4G | MQLPLAT (SEQ ID NO: 18) | N/A | (SGRGKQGGKARAK AKTRSSRAGLQFPV GRVHRLLRK)4 (SEQ ID NO: 5) | WEAALAEALAEALA EHLAEALAEALEAL AA (SEQ ID NO: 6) |

TABLE 1-continued

The amino acid sequences of the designed recombinant vectors for stem cell transfection.

| Name | Cell Targeting Peptide | Cell Penetrating Peptide | DNA Condensing Motif (H4) | Fusogenic Peptide (GALA) |
|---|---|---|---|---|
| EGFR-H4G | YHWYGYTPQNVI (SEQ ID NO: 19) | N/A | (SGRGKQGGKARAK AKTRSSRAGLQFPV GRVHRLLRK)4 (SEQ ID NO: 5) | WEAALAEALAEALA EHLAEALAEALEAL AA (SEQ ID NO: 6) |
| PDGFR-H4G | IPLPPPSRPFFK (SEQ ID NO: 20) | N/A | (SGRGKQGGKARAK AKTRSSRAGLQFPV GRVHRLLRK)4 (SEQ ID NO: 5) | WEAALAEALAEALA EHLAEALAEALEAL AA (SEQ ID NO: 6) |
| INTEGRIN-H4G | RGDSPASSKP (SEQ ID NO: 21) | N/A | (SGRGKQGGKARAK AKTRSSRAGLQFPV GRVHRLLRK)4 (SEQ ID NO: 5) | WEAALAEALAEALA EHLAEALAEALEAL AA (SEQ ID NO: 6) |

TABLE 2

| Vector | Amino Acid Sequence |
|---|---|
| H4G (SEQ ID NO: 7) | SGRGKQGGKARAKAKTRSSRAGLQFPVGRVHRLLRKSGRGK QGGKARAKAKTRSSRAGLQFPVGRVHRLLRKSGRGKQGGKA RAKAKTRSSRAGLQFPVGRVHRLLRKSGRGKQGGKARAKAK TRSSRAGLQFPVGRVHRLLRKGGGWEAALAEALAEALAEHL AEALAEALEALAA |
| MPG-H4G (SEQ ID NO: 8) | GALFLGFLGAAGSTMGAWSQPKKKRKVSGRGKQGGKARAKA KTRSSRAGLQFPVGRVHRLLRKSGRGKQGGKARAKAKTRSS RAGLQFPVGRVHRLLRKSGRGKQGGKARAKAKTRSSRAGLQ FPVGRVHRLLRKSGRGKQGGKARAKAKTRSSRAGLQFPVGR VHRLLRKGGGWEAALAEALAEALAEHLAEALAEALEALAA |
| Pep1-H4G (SEQ ID NO: 9) | KETWWETWWTEWSQPKKKRKVSGRGKQGGKARAKAKTRSSR AGLQFPVGRVHRLLRKSGRGKQGGKARAKAKTRSSRAGLQF PVGRVHRLLRKSGRGKQGGKARAKAKTRSSRAGLQFPVGRV HRLLRKSGRGKQGGKARAKAKTRSSRAGLQFPVGRVHRLLR KGGGWEAALAEALAEALAEHLAEALAEALEALAA |
| Vago-H4G (SEQ ID NO: 10) | KLTWQELYQLKYKGIGGGSGGGSGGGSGRGKQGGKARAKAK TRSSRAGLQFPVGRVHRLLRKSGRGKQGGKARAKAKTRSSR AGLQFPVGRVHRLLRKSGRGKQGGKARAKAKTRSSRAGLQF PVGRVHRLLRKSGRGKQGGKARAKAKTRSSRAGLQFPVGRV HRLLRKGGGWEAALAEALAEALAEHLAEALAEALEALAA |
| Vanta-H4G (SEQ ID NO: 11) | NGYEIEWYSWVTHGMYGGGSGGGSGGGSGRGKQGGKARAKA KTRSSRAGLQFPVGRVHRLLRKSGRGKQGGKARAKAKTRSS RAGLQFPVGRVHRLLRKSGRGKQGGKARAKAKTRSSRAGLQ FPVGRVHRLLRKSGRGKQGGKARAKAKTRSSRAGLQFPVGR VHRLLRKSGRGKQGGKARAKAKTRSSRAGLQFPVGR VHRLLRKGGGWEAALAEALALEALAEHLAEALAEALEALAA |
| IGFR-H4G (SEQ ID NO: 22) | LLGDFFRKSKEKIGKEFKRIVQRIKDFLRNLVPRTESGGGS GGGSGGGSGRGKQGGKARKAKAKTRSSRAGLQFPVGRVHRL LRKSGRGKQGGKARAKAKTRSSRAGLQFPVGRVHRLLRKGS RGKQGGKARAKAKTRSSRAGLQFPVGRVHRLLRKSGRGKQQ GKARAKAKTRSSRAGLQFPVGRVHRLLRKGGGWEAALAEAL AEALAEHLAEALAEALEALAA |
| FGFR-H4G (SEQ ID NO: 23) | MQLPLATGGGSGGGSGGGSGRGKQGGKARAKAKTRSSRAGL QFPVGRVHRLLRKSGRGKQGGKARAKAKTRSSRAGLQFPVG RVHRLLRKSGRGKQGGKARAKAKTRSSRAGLQFPVGRVHRL LRKSGRGKQGGKARAKAKTRSSRAGLQFPVGRVHRLLRKGG GWEAALAEALAEALAEHLAEALAEALEALAA |
| EGFR-H4G (SEQ ID NO: 24) | YHWYGYTPQNVIGGGSGGGSGGGSGRGKQGGKARAKAKTRS SRAGLQFPVGRVHRLLRKSGRGKQGGKARAKAKTRSSRAGL QFPVGRVHRLLRKSGRGKQGGKARAKAKTRSSRAGLQFPVG RVHRLLRKSGRGKQGGKARAKAKTRSSRAGLQFPVGRVHRL LRKGGGWEAALAEALAEALAEHLAEALAEALEALAA |
| PDGFR-H4G (SEQ ID NO: 25) | IPLPPPSRPFFKGGGSGGGSGGGSGRGKQGGKARAKAKTRS SRAGLQFPVGRVHRLLRKSGRGKQGGKARAKAKTRSSRAGL QFPVGRVHRLLRKSGRGKQGGKARAKAKTRSSRAGLQFPVG RVHRLLRKSGRGKQGGKARAKAKTRSSRAGLQFPVGRVHRL LRKGGGWEAALAEALAEALAEHLAEALAEALEALAA |
| INTEGRIN-H4G (SEQ ID NO: 26) | RGDSPASSKPGGGSGGGSGGGSGRGKQGGKARAKAKTRSSR AGLQFPVGRVHRLLRKSGRGKQGGKARAKAKTRSSRAGLQF PVGRVHRLLRKSGRGKQGGKARAKAKTRSSRAGLQFPVGRV HRLLRKSGRGKQGGKARAKAKTRSSRAGLQFPVGRVHRLLR KGGGWEAALAEALAEALAEHLAEALAEALEALAA |

TABLE 3

| Peptide | Amino Acid Sequence | SEQ ID NO: |
|---|---|---|
| INF-7 | GLFEAIEGFIENGWEGMIDGWYG | SEQ ID NO: 12 |
| KALA | WEAKLAKALAKALAKHLAKALAKALKACEA | SEQ ID NO: 13 |
| RALA | WEARLARALARALARHLARALARALRAGEA | SEQ ID NO: 14 |
| H5WYG | GLFHAIAHFIHGGWHGLIHGWYG | SEQ ID NO: 15 |
| LAGA | WEAALAEAEALALAEKEALALAEAELALAA | SEQ ID NO: 16 |

REFERENCES

1. Shah K. Mesenchymal stem cells engineered for cancer therapy. *Adv Drug Deliv Rev* 2012, 64(8): 739-748.
2. Hamada H, Kobune M, Nakamura K, Kawano Y, Kato K, Honmou O, et al. Mesenchymal stem cells (MSC) as therapeutic cytoreagents for gene therapy. *Cancer Sci* 2005, 96(3): 149-156.
3. Uhl M, Weiler M, Wick W, Jacobs A H, Weller M, Herrlinger U. Migratory neural stem cells for improved thymidine kinase-based gene therapy of malignant gliomas. *Biochem Biophys Res Commun* 2005, 328(1): 125-129.
4. Kucerova L, Altanerova V, Matuskova M, Tyciakova S, Altaner C. Adipose tissue-derived human mesenchymal stem cells mediated prodrug cancer gene therapy. *Cancer Res* 2007, 67(13): 6304-6313.

5. Cavarretta I T, Altanerova V, Matuskova M, Kucerova L, Culig Z, Altaner C. Adipose tissue-derived mesenchymal stem cells expressing prodrug-converting enzyme inhibit human prostate tumor growth. *Mol Ther* 2010, 18(1): 223-231.
6. Noyan F, Diez I A, Hapke M, Klein C, Dewey R A. Induced transgene expression for the treatment of solid tumors by hematopoietic stem cell-based gene therapy. *Cancer Gene Ther* 2012, 19(5): 352-357.
7. Nouri F S, Wang X, Hatefi A. Genetically engineered theranostic mesenchymal stem cells for the evaluation of the anticancer efficacy of enzyme/prodrug systems. *J Control Release* 2015, 200: 179-187.
8. Aboody K S, Najbauer J, Danks M K. Stem and progenitor cell-mediated tumor selective gene therapy. *Gene Ther* 2008, 15(10): 739-752.
9. Thomas C E, Ehrhardt A, Kay M A. Progress and problems with the use of viral vectors for gene therapy. *Nat Rev Genet* 2003, 4(5): 346-358.
10. Kim J A, Cho K, Shin M S, Lee W G, Jung N, Chung C, et al. A novel electroporation method using a capillary and wire-type electrode. *Biosens Bioelectron* 2008, 23(9): 1353-1360.
11. Hubbs A F, Mercer R R, Benkovic S A, Harkema J, Sriram K, Schwegler-Berry D, et al. Nanotoxicology—a pathologist's perspective. *Toxicol Pathol* 2011, 39(2): 301-324.
12. Norppa H, Catalan J, Falck G, Hannukainen K, Siivola K, Savolainen K. Nano-specific genotoxic effects. *J Biomed Nanotechnol* 2011, 7(1): 19.
13. Deshayes S, Morris M C, Divita G, Heitz F. Interactions of amphipathic carrier peptides with membrane components in relation with their ability to deliver therapeutics. *J Pept Sci* 2006, 12(12): 758-765.
14. Deshayes S, Gerbal-Chaloin S, Morris M C, Aldrian-Herrada G, Charnet P, Divita G, et al. On the mechanism of non-endosomial peptide-mediated cellular delivery of nucleic acids. *Biochim Biophys Acta* 2004, 1667(2): 141-147.
15. An J J, Lee Y P, Kim S Y, Lee S H, Lee M J, Jeong M S, et al. Transduced human PEP-1-heat shock protein 27 efficiently protects against brain ischemic insult. *FEBS J* 2008, 275(6): 1296-1308.
16. Muller J, Triebus J, Kretzschmar I, Vollmer R, Boisguerin P. The agony of choice: how to find a suitable CPP for cargo delivery. *J Pept Sci* 2012, 18(5): 293-301.
17. Milletti F. Cell-penetrating peptides: classes, origin, and current landscape. *Drug Discov Today* 2012, 17(15-16): 850-860.
18. Karjoo Z, McCarthy H O, Patel P, Noun F S, Hatefi A. Systematic engineering of uniform, highly efficient, targeted and shielded viral-mimetic nanoparticles. *Small* 2013, 9(16): 2774-2783.
19. Nouri F S, Wang X, Dorrani M, Karjoo Z, Hatefi A. A recombinant biopolymeric platform for reliable evaluation of the activity of pH-responsive amphiphile fusogenic peptides. *Biomacromolecules* 2013, 14(6): 2033-2040.
20. Wang Y, Mangipudi S S, Canine B F, Hatefi A. A designer biomimetic vector with a chimeric architecture for targeted gene transfer. *J Control Release* 2009, 137(1): 46-53.
21. Chen X, Nomani A, Patel N, Hatefi A. Production of low-expressing recombinant cationic biopolymers with high purity. *Protein Expr Purif* 2017, 134: 11-17.
22. Bryce S M, Bemis J C, Avlasevich S L, Dertinger S D. In vitro micronucleus assay scored by flow cytometry provides a comprehensive evaluation of cytogenetic damage and cytotoxicity. *Mutat Res* 2007, 630(1-2): 78-91.
23. Paul R W, Weisser K E, Loomis A, Sloane D L, LaFoe D, Atkinson E M, et al. Gene transfer using a novel fusion protein, GAL4/invasin. *Hum Gene Ther* 1997, 8(10): 1253-1262.
24. McCarthy H O, Wang Y, Mangipudi S S, Hatefi A. Advances with the use of bio-inspired vectors towards creation of artificial viruses. *Expert Opin Drug Deliv* 2010, 7(4): 497-512.
25. Canine B F, Wang Y, Hatefi A. Biosynthesis and characterization of a novel genetically engineered polymer for targeted gene transfer to cancer cells. *J Control Release* 2009, 138(3): 188-196.
26. Canine B F, Wang Y, Ouyang W, Hatefi A. Development of targeted recombinant polymers that can deliver siRNA to the cytoplasm and plasmid DNA to the cell nucleus. *J Control Release* 2011, 151(1): 95-101.
27. Mangipudi S S, Canine B F, Wang Y, Hatefi A. Development of a genetically engineered biomimetic vector for targeted gene transfer to breast cancer cells. *Mol Pharm* 2009, 6(4): 1100-1109.
28. Wang Y, Canine B F, Hatefi A. HSV-TK/GCV cancer suicide gene therapy by a designed recombinant multifunctional vector. *Nanomedicine* 2011, 7(2): 193-200.
29. Wang Y, Mangipudi S S, Canine B F, Hatefi A. A designer biomimetic vector with a chimeric architecture for targeted gene transfer. *J Control Release* 2009, 137: 46-53.
30. Balicki D, Putnam C D, Scaria P V, Beutler E. Structure and function correlation in histone H2A peptide-mediated gene transfer. *Proc Natl Acad Sci USA* 2002, 99(11): 7467-7471.
31. Karjoo Z, McCarthy H O, Patel P, Nouri F S, Hatefi A. Systematic Engineering of Uniform, Highly Efficient, Targeted and Shielded Viral-Mimetic Nanoparticles. *Small* 2013.
32. D'Andrea L D, Iaccarino G, Fattorusso R, Sorriento D, Carannante C, Capasso D, et al. Targeting angiogenesis: structural characterization and biological properties of a de novo engineered VEGF mimicking peptide. *Proc Nall Acad Sci USA* 2005, 102(40): 14215-14220.
33. El-Mousawi M, Tchistiakova L, Yurchenko L, Pietrzynski G, Moreno M, Stanimirovic D, et al. A vascular endothelial growth factor high affinity receptor 1-specific peptide with antiangiogenic activity identified using a phage display peptide library. *J Biol Chem* 2003, 278(47): 46681-46691.
34. Bolanos-Garcia V M, Davies O R. Structural analysis and classification of native proteins from *E. coli* commonly co-purified by immobilised metal affinity chromatography. *Biochim Biophys Acta* 2006, 1760(9): 1304-1313.
35. Nouri F S, Wang X, Chen X, Hatefi A. Reducing the Visibility of the Vector/DNA Nanocomplexes to the Immune System by Elastin-Like *Peptides. Pharm Res* 2015, 32(9): 3018-3028.
36. Shah V, Taratula O, Garbuzenko O B, Patil M L, Savla R, Zhang M, et al. Genotoxicity of Different Nanocarriers: Possible Modifications for the Delivery of Nucleic Acids. *Curr Drug Discov Technol* 2012.
37. Yang J, Yan R, Roy A, Xu D, Poisson J, Zhang Y. The I-TASSER Suite: protein structure and function prediction. *Nat Methods* 2015, 12(1): 7-8.
38. Hamma-Kourbali Y, Starzec A, Vassy R, Martin A, Kraemer M, Perret G, et al. Carboxymethyl benzylamide dextran inhibits angiogenesis and growth of VEGF-overexpressing human epidermoid carcinoma xenograft in nude mice. *Br J Cancer* 2003, 89(1): 215-221.
39. Mesti T, Savarin P, Triba M N, Le Moyec L, Ocvirk J, Banissi C, et al. Metabolic impact of anti-angiogenic agents on U87 glioma cells. *PloS one* 2014, 9(6): e99198.
40. Lim S J, Paeng J C, Kim S J, Kim S Y, Lee H, Moon D H Enhanced expression of adenovirus-mediated sodium iodide symporter gene in MCF-7 breast cancer cells with retinoic acid treatment. *J Nucl Med* 2007, 48(3): 398-404.
41. Jones C F, Grainger D W. In vitro assessments of nanomaterial toxicity. *Adv Drug Deliv Rev* 2009, 61(6): 438-456.
42. Parhamifar L, Andersen H, Wu L, Hall A, Hudzech D, Moghimi S M. Polycation-mediated integrated cell death processes. *Adv Genet* 2014, 88: 353-398.
43. Moghimi S M, Symonds P, Murray J C, Hunter A C, Debska G, Szewczyk A. A two-stage poly(ethylenimine)-mediated cytotoxicity: implications for gene transfer/therapy. *Mol Ther* 2005, 11(6): 990-995.
44. Hunter A C. Molecular hurdles in polyfectin design and mechanistic background to polycation induced cytotoxicity. *Adv Drug Deliv Rev* 2006, 58(14): 1523-1531.
45. Warheit D B, Donner E M. Rationale of genotoxicity testing of nanomaterials: regulatory requirements and appropriateness of available OECD test guidelines. *Nanotoxicology* 2010, 4: 409-413.
46. Wang L, Zhao Y, Liu Y, Akiyama K, Chen C, Qu C, et al. IFN-gamma and TNF-alpha synergistically induce mesenchymal stem cell impairment and tumorigenesis via NFkappaB signaling. *Stem Cells* 2013, 31(7): 1383-1395.
47. Broudy V C. Stem cell factor and hematopoiesis. *Blood* 1997, 90(4): 1345-1364.
48. Matsui J, Wakabayashi T, Asada M, Yoshimatsu K, Okada M. Stem cell factor/c-kit signaling promotes the survival, migration, and capillary tube formation of human umbilical vein endothelial cells. *J Biol Chem* 2004, 279(18): 18600-18607.
49. Litz J, Krystal G W. Imatinib inhibits c-Kit-induced hypoxia-inducible factor-1alpha activity and vascular endothelial growth factor expression in small cell lung cancer cells. *Mol Cancer Ther* 2006, 5(6): 1415-1422.

GENERAL METHODS

Standard methods in molecular biology are described Sambrook, Fritsch and Maniatis (1982 & 1989 2$^{nd}$ Edition, 2001 3$^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, 3$^{rd}$ ed.*, Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

INCORPORATION BY REFERENCE

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims. The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and systems of the present invention, where the term comprises is used with respect to the recited steps or components, it is also contemplated that the methods and systems consist essentially of, or consist of, the recited steps or components. Further, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise.

Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

What is claimed is:

1. A fusion polypeptide, comprising:
   i. a cell surface receptor-binding peptide, wherein the cell surface receptor-binding peptide is a vascular endothelial growth factor receptor (VEGFR)-binding peptide comprising an amino acid sequence at least 90% identical to the amino acid sequence set forth in SEQ ID NO: 1 or SEQ ID NO: 2;
   ii. a nucleic acid-binding polypeptide, wherein the nucleic acid-binding polypeptide comprises 2 to 10 repeats of a histone H2A comprising SEQ ID NO: 248 or SEQ ID NO: 5; and
   iii. an endosomolytic peptide, wherein the endosomolytic peptide is GALA comprising and has an amino acid at least 90% identical to the amino acid sequence set forth in SEQ ID NO: 6.

2. The fusion polypeptide of claim 1, wherein the VEGFR-binding peptide is an antagonist of VEGFR or an agonist of VEGFR.

3. The fusion polypeptide of claim 1, comprising:
   i. a cell surface receptor-binding peptide, wherein the cell surface receptor-binding peptide is a VEGFR-binding peptide comprising SEQ ID NO: 1 or 2,
   ii. a nucleic acid-binding polypeptide, wherein the nucleic acid-binding polypeptide comprises 2 to 10 repeats of a histone H2A comprising SEQ ID NO: 248 or SEQ ID NO: 5; and
   iii. an endosomolytic peptide, wherein the endosomolytic peptide is GALA and has an amino acid that is at least 90% identical to the amino acid sequence set forth in SEQ ID NO: 6.

4. The fusion polypeptide of claim 1, wherein the nucleic acid binding polypeptide comprises 4 repeats of the histone H2A comprising SEQ ID NO: 248 or SEQ ID NO:5.

5. The fusion polypeptide of claim 1, wherein the endosomolytic peptide comprises the amino acid sequence set forth in SEQ ID NO: 6.

6. A system for transfection of a nucleic acid into a stem cell, comprising:
   (a) a nucleic acid;
   (b) a fusion polypeptide comprising:
      (i) a cell surface receptor-binding peptide, wherein the cell surface receptor-binding peptide is a vascular endothelial growth factor receptor (VEGFR)-binding peptide comprising SEQ ID NO: 1 or 2;
      (ii) a nucleic acid-binding polypeptide, wherein the nucleic acid-binding polypeptide comprises 2 to 10 repeats of a histone H2A comprising SEQ ID NO: 248 or SEQ ID NO: 5, and
      (iii) an endosomolytic peptide, wherein the endosomolytic peptide is GALA comprising SEQ ID NO: 6;
   wherein the fusion polypeptide is in an aqueous medium with a conductivity no greater than 10 mS/cm; and
   (c) a combination of dexamethasone, insulin, transferrin, and a selenite; wherein the nucleic acid (N) and the fusion polypeptide (P) have a N:P ratio ranging from about 1:1 to about 15.1.

7. The system of claim 6, wherein the nucleic acid-binding polypeptide comprises 4 repeats of the histone H2A comprising SEQ ID NO: 48.

8. The system of claim 6, wherein the aqueous medium has a conductivity no greater than 2 mS/cm.

9. The system of claim 6, wherein the aqueous medium has a conductivity of about 0.45 mS/cm.

10. The system of claim 6, wherein the system comprises about 0.1 μg/ml to about 0.6 ug/ml dexamethasone, about 5 ug/ml to about 20 ug/ml insulin, about 3 ug/ml to about 10 μg/ml transferrin, and about 0.003 ug/ml to about 0.010 ug/ml selenite.

11. The system of claim 6, wherein the N:P ratio ranges from about 1:1 to about 12:1.

12. The system of claim 6, wherein the N:P ratio is about 5:1.

13. A method of transfecting a nucleic acid into a stem cell in serum free media, the method comprising contacting the stem cell in serum free media with
   (a) a nucleic acid;
   (b) a fusion polypeptide comprising:
      (i) a cell surface receptor-binding peptide, wherein the cell surface receptor-binding peptide is a vascular endothelial growth factor receptor (VEGFR)-binding peptide comprising SEQ ID NO: 1 or 2;
      (ii) a nucleic acid-binding polypeptide, wherein the nucleic acid-binding polypeptide comprises 2 to 10 repeats of a histone H2A comprising SEQ ID NO: 248 or SEQ ID NO: 5, and
      (iii) an endosomolytic peptide, wherein the endosomolytic peptide is GALA comprising SEQ ID NO: 6;
   wherein the fusion polypeptide is in an aqueous medium with a conductivity no greater than 10 mS/cm; and
   (c) a combination of dexamethasone, insulin, transferrin, and a selenite,
      wherein the nucleic acid (N) and the fusion polypeptide (P) have a N:P ratio ranging from about 1:1 to about 15.1.

14. The method of claim 13, wherein the stem cell is an induced pluripotent stem cell, a blood stem cell, an adipose stem cell, a bone marrow mesenchymal stem cell, a mesenchymal stem cell, a neural stem cell, a skin stem cell, an endothelial stem cell, a hepatic stem cell, a pancreatic stem cell, an intestinal epithelium stem cell, or a germ stem cell.

15. The method of claim 13, wherein contacting the stem cell in serum free media with the fusion polypeptide of claim 6 and a combination of dexamethasone, insulin, transferrin, and a selenite occurs in vitro.

16. The system of claim 6, wherein the nucleic acid-binding polypeptide comprises 4 repeats of the histone H2A comprising SEQ ID NO: 5.

17. The system of claim 6, wherein the stem cell is an induced pluripotent stem cell, a blood stem cell, an adipose stem cell, a bone marrow mesenchymal stem cell, a mesenchymal stem cell, a neural stem cell, a skin stem cell, an endothelial stem cell, a hepatic stem cell, a pancreatic stem cell, an intestinal epithelium stem cell, or a germ stem cell.

* * * * *